US005795977A

United States Patent [19]
Ugarkar et al.

[11] Patent Number: 5,795,977
[45] Date of Patent: *Aug. 18, 1998

[54] WATER SOLUBLE ADENOSINE KINASE INHIBITORS

[75] Inventors: Bheemarao G. Ugarkar, Escondido; Mark D. Erion, Del Mar; Jorge E. Gomez Galeno, La Jolla, all of Calif.

[73] Assignee: Metabasis Therapeutics, Inc., San Diego, Calif.

[*] Notice: The term of this patent shall not extend beyond the expiration date of Pat. No. 5,726,308.

[21] Appl. No.: 660,532

[22] Filed: Jun. 7, 1996

Related U.S. Application Data

[63] Continuation-in-part of Ser. No. 473,492, Jun. 7, 1995, which is a continuation-in-part of Ser. No. 812,916, Dec. 23, 1991, abandoned, which is a continuation-in-part of Ser. No. 647,117, Jan. 23, 1991, abandoned, which is a continuation-in-part of Ser. No. 466,979, Jan. 18, 1990, abandoned, which is a continuation-in-part of Ser. No. 408,707, Sep. 18, 1989, abandoned.

[51] Int. Cl.$^6$ ..................... C07H 19/16
[52] U.S. Cl. .................. 536/27.13; 536/27.1; 536/27.2; 536/27.21; 536/27.23; 536/27.6; 536/27.62; 536/27.63; 536/27.7
[58] Field of Search .................. 536/27.1, 27.13, 536/27.2, 27.21, 27.23, 27.6, 27.62, 27.63, 27.7

[56] References Cited

U.S. PATENT DOCUMENTS

| | | | |
|---|---|---|---|
| 4,455,420 | 6/1984 | Kazlaukas | 536/24 |
| 4,904,666 | 2/1990 | Friebe et al. | |

FOREIGN PATENT DOCUMENTS

| | | |
|---|---|---|
| 0 496 617 A | 7/1992 | European Pat. Off. |
| WO 94/17803 | 8/1994 | WIPO |
| WO 94/18215 | 8/1994 | WIPO |

OTHER PUBLICATIONS

Abdalla, G.M. and Sowell, J.W., Sr., *J. Heterocyclic Chem.* 24, 297–301 (1987).
Achtenberg et al., *Biochem. J.*, 235, 13–17 (1986).
Agarwal, K.C., et al, *Biochem. Pharmacol.*, 28, 501–10 (1978).
Amarnath, V. and Madhav, R., *Synth.* 837, 846–51 (Dec. 1974).
Bergstrom, D.E., et al., *J. Med. Chem.*, 27, 285–92 (1984).
Bontemps et al., *Proc. Natl. Acad. Sci. USA*, 80, 2829–33 (1983).
Caldwell and Henderson, *Cancer Chemother. Rep.*, 2, 237–46 (1971).
Carboni, R.A., et al., *J. Am. Chem. Soc.*, 80, 2838–40 (1958).
Chat, I., et al., *J. Med. Chem.*, 18, 161–65 (1975).
Cottam, H.B., et al., *J. Med. Chem.*, 27, 119–27 (1984).
Davies et al., *Biochem. Pharmacol.*, 35, 3021–29 (1986).
Davies et al., *Biochem. Pharmacol.*, 33, 347–55 (1984).
Davoll, J., *J. Chem. Soc.*, 131–38 (1960).
Divekar, A.Y. and Hakala, M.T., *Mol. Pharmacol.*, 7, 663–73 (1971).
Firestein et al., *J. Immunology* 154, 326–34 (1995).
Gerwald, R., *Z. Chem.*, 1, 349 (1961).
Green, *J. Supramol. Structure*, 13:175–182 (1980).
Henderson et al., *Cancer Chemotherapy Rep.* Part 2, 3, 71–85 (1972).
Hinshaw, B.C., et al., *J. Heterocyclic Chem.*, 6, 215–21 (1969).
Ikehara, M., et al., *Tetrahedron*, 26, 5757–63 (1970).
Keil et al., *Life Sciences* 5, 171–76 (1992).
Kobayashi, S., *Chem. Pharm. Bull.*, 21, 941–51 (1973).
Newby et al., *Biochem. J.*, 214, 317–323 (1983).
Noell, C.W., et al., *J. Heterocyclic Chem.*, 1, 34–41 (1964).
Miller et al., *J. Biol. Chem.*, 254, 2346–52 (1979).
Pak et al., *Soc. for Neuroscience Abs.*, 20, 149.2 (1994).
Phillis et al., *Life Sciences*, 53, 497–502 (1993).
Prescott et al., *Nucleosides & Nucleotide*, 8, 297 (1989).
Pudlo, J.S., et al., *J. Med. Chem.*, 33, 1984–92 (1990).
Rosemeyer, H. and Seela, F., *Helv. Chim. Acta*, 71, 1573–85 (1988).
Schrader, in *Regulatory Function of Adenosine*; Berne et al., eds. pp. 133–156 (1983).
Sciotti et al., *J. Cerebral Blood Flow Metab.*, 13, 201–207 (1993).
Seela, F., et al., *Liebigs Ann. Chem.*, 15–19 (1987).
Stout, M.G., et al., *J. Org. Chem.*, 33, 1219–25 (1968).
Synder, J.R. et al., *Carbohydrate Res.*, 163, 169–88 (1987).
Taylor, E.C. and Hendess, R.W., *J. Am. Chem. Soc.* 87, 1995–2003 (1965).
Taylor, E.C., et al., *J. Org. Chem.*, 31, 342–43 (1966).
Tominaga, Y., et al., *J. Heterocyclic Chem.*, 27, 647–60 (1990).
White, *Soc. Neurosci. Abs.*, 20, 308.9 (1994).
Wu, et al., *Cytobios*, 50, 7–12 (1987).
Zhang et al., *J. Pharmacol. Exper. Ther.* 264(3), 1415 (1993).
Zoref-Shani et al., *J. Mol. Cell. Cardiol.*, 20, 23–33 (1988).

*Primary Examiner*—James O. Wilson
*Attorney, Agent, or Firm*—Darby & Darby P.C.

[57] ABSTRACT

This invention relates to adenosine kinase inhibitors and to nucleoside analogs, specifically to water soluble, aryl substituted 4-amino pyrrolo[2,3-d] pyrimidine and pyrazolo[3,4-d] pyrimidine nucleoside analogs having activity as adenosine kinase inhibitors The invention also relates to the preparation and use of these adenosine kinase inhibitors in the treatment of cardiovascular, and cerebrovascular diseases, inflammation and other diseases which can be regulated by increasing the local concentration of adenosine.

21 Claims, 2 Drawing Sheets

WATER SOLUBLE ADENOSINE KINASE INHIBITORS

CROSS-REFERENCE TO RELATED APPLICATIONS

This application is a continuation in part of U.S. patent application Ser. No. 08/473,492, filed Jun. 7, 1995, which is a continuation in part of U.S. patent application Ser. No. 07/812,916, filed Dec. 23, 1991, now abandoned, which is a continuation in part of U.S. patent application Ser. No. 07/647,117, filed Jan. 23, 1991, now abandoned, which is a continuation in part of U.S. patent application Ser. No. 07/466,979, filed Jan. 18, 1990, now abandoned, which is a continuation in part of U.S. application Ser. No. 07/408,707, filed Sep. 18, 1989, now abandoned. The disclosure of these applications are incorporated herein by reference.

BACKGROUND OF THE INVENTION

1. Field of the Invention

This invention relates to adenosine kinase inhibitors and to nucleoside analogs, specifically to water soluble, aryl substituted 4-amino pyrrolo[2,3-d] pyrimidine and pyrazolo [3,4-d] pyrimidine nucleoside analogs having activity as adenosine kinase inhibiters. The invention also relates to the preparation and use of these adenosine kinase inhibitors in the treatment of cardiovascular and cerebrovascular diseases, inflammation and other diseases which can be regulated by increasing the local concentration of adenosine.

2. Description of the Related Art

Adenosine is an endogenously produced molecule that plays a major role in a variety of important cellular processes. It is a vasodilator, can inhibit immune function, enhance activation of mast cells (associated with allergic reactions), inhibit neutrophil oxygen free-radical production, is antiarrhythmic, and is an inhibitory neurotransmitter. Adenosine is phosphorylated to adenosine triphosphate (ATP) which is used by all cells to store energy for use in future energy-utilizing metabolic reactions or mechanical work (e.g. muscle contraction). Extracellular adenosine, frequently produced by breakdown of intracellular ATP pools, evokes a variety of pharmacological responses through activation of extracellular adenosine receptors located on the surface of nearly all cells. For example, adenosine produces a variety of cardiovascular related effects including vasodilation, inhibition of platelet aggregation, and negative inotropic, chronotropic and dromotropic effects on the heart. Adenosine also has effects within the central nervous system (CNS) including inhibition of neurotransmitter release from presynaptic neurons and inhibition of post-synaptic neuron firing in brain and the spinal cord and at sites of inflammation, such as inhibition of neutrophil adhesion to endothelial cells and inhibition of neutrophil oxygen free-radical production.

Compounds that increase extracellular adenosine can be beneficial to living organisms, particularly under certain conditions. For example, compounds that increase adenosine levels have been associated with the treatment of ischemic conditions such as stroke, as well as other conditions benefitted by enhanced adenosine levels, such as inflammation, arthritis, seizures, epilepsy and other neurological conditions. The compounds are also useful for treating pain, as muscle relaxants, and for inducing sleep.

Adenosine kinase is a cytosolic enzyme which catalyzes the phosphorylation of adenosine to AMP. Inhibition of adenosine kinase can potentially reduce the ability of the cell to utilize adenosine, leading to increased adenosine outside of the cell where it is pharmacologically active. However, the regulation of adenosine concentration is complex and involves other adenosine-metabolizing enzymes each with different kinetic properties and mechanisms of regulation. Adenosine can also be deaminated to inosine by adenosine deaminase (ADA) and condensed with L-homocysteine to S-adenosylhomocysteine (SAH) by SAH hydrolase. The role of each of these enzymes in modulating adenosine concentration is dependent on the prevailing physiological conditions, is tissue specific and is not well understood.

A number of nucleosides including pyrrolo[2,3-d] pyrimidine and pyrazolo[3,4-d]pyrimidine analogs have been evaluated for inhibition of adenosine kinase but were reported to have $K_i$'s of greater than 800 nM. Caldwell and Henderson, *Cancer Chemother. Rep.*, 2:237–46 (1971); Miller et al., *J. Biol. Chem.*, 254:2346–52 (1979). A few compounds have been reported as potent inhibitors of adenosine kinase with $K_i$'s of less than 100 nM. These are the purine nucleosides, 5'-amino-5'-deoxyadenosine (Miller et al.) and 1,12-bis(adenosin-$N^6$-yl)dodecane (Prescott et al., *Nucleosides & Nucleotides*, 8:297 (1989)); and the pyrrolopyrimidine nucleosides, 5-iodotubercidin (Henderson et al., *Cancer Chemotherapy Rep. Part 2*, 3:71–85 (1972); Bontemps et al., *Proc. Natl. Acad. Sci. USA*, 80:2829–33 (1983); Davies et al., *Biochem. Pharmacol.*, 35:3021–29 (1986)) and 5'-deoxy-5-iodotubercidin (Davies et al., *Biochem. Pharmacol.*, 33:347–55 (1984) and 35:3021–29 (1986)).

Some of these compounds have been used to evaluate whether adenosine kinase inhibition might lead to increased extracellular adenosine concentrations. In rat cardiomyocytes, inhibition of adenosine deaminase by 2'-deoxycoformycin was reported to have no effect on adenosine release from the cells. In contrast, inhibition of ADA together with adenosine kinase by 5'-amino-5'-deoxyadenosine resulted in a 6-fold increase in adenosine release. Zoref-Shani et al., *J. Mol. Cell. Cardiol.*, 20:23–33 (1988). The effects of the adenosine kinase inhibitor alone were not reported. Similar results were reported in isolated guinea pig hearts; in these studies addition of 5'-amino-5'-deoxyadenosine to the perfusion medium, in the presence of EHNA to inhibit deamination, was reported to result in a 15-fold increase of adenosine release. Schrader in *Regulatory Function of Adenosine*; (Berne et al.) eds. pp. 133–156 (1983). These effects were not apparent in the absence of ADA inhibition, and other studies using isolated rat hearts perfused with 5-iodotubercidin alone, have reported no increase in perfusate adenosine concentration under normoxic conditions Newby et al., *Biochem. J.*, 214:317–323 (1983), or under hypoxic, anoxic or ischemic conditions, Achtenberg et al., *Biochem. J.*, 235:13–17 (1986). In other studies, adenosine release has been measured in neuroblastoma cells in culture and compared with that of a variant deficient in adenosine kinase (AK⁻). The AK cells used in this study were said to release adenosine at an accelerated rate; the concentration of adenosine in the growth medium was reported to be elevated compared to the normal cells. Green, *J. Supramol. Structure*, 13:175–182 (1980). In rat and guinea pig brain slices, adenosine uptake was reportedly inhibited by the adenosine kinase inhibitors, 5-iodotubercidin and 5'-deoxy-5-iodotubercidin. Davis et al., *Biochem. Pharmacol.*, 33:347–55 (1984). However, inhibition of uptake and intracellular trapping via phosphorylation does not necessarily result in increased extracellular adenosine, since the adenosine could enter other metabolic pathways or the percentage of adenosine being phosphorylated could be insignificant compared to the total adenosine removed.

The effects of adenosine and certain inhibitors of adenosine catabolism, including 5-iodotubericidin were evaluated in an experimental model in which dog hearts were subjected to ischemia and reperfusion; 5-iodotubericidin was reported to have inconsistent effects. Wu, et al., *Cytobios*, 50:7-12 (1987).

Although the adenosine kinase inhibitors, 5'-amino-5'-deoxyadenosine and 5-iodotubercidin have been widely used in experimental models, the susceptibility of 5'-amino-5'-deoxyadenosine to deamination, and hence its potentially short half life, and the cytotoxicity of 5-iodotubercidin make their clinical utility limited and may limit interpretations based on these compounds. The known pyrrolo[2,3-d] pyrimidines, 5-iodotubercidin and 5'-deoxy-5-iodotubercidin have been reported to cause pronounced general flaccidity and much-reduced spontaneous locomotor activity in mice, interpreted to be skeletal muscle relaxation; to cause hypothermia in mice; and to decrease blood pressure and heart rate in anesthetized rats. Daves et al., *Biochem. Pharmacol.*, 33:347-55 (1984) and 35:3021-29 (1986); and U.S. Pat. No. 4,455,420). The skeletal muscle effects of these compounds have been poorly documented, while the other effects were considered significant toxicities.

More recent references concerned with the mechanisms and effects of adenosine kinase inhibitors are Keil et al., *Life Sciences* 51:171-76 (1992); Zhang et al., *J.Pharmacol. Exper. Ther.* 264(3): 1415 (1993); Phillis et al., *Life Sciences*, 53: 497-502 (1993); Sciotti et al., *J. Cerebral Blood Flow Metab.*, 13:201-207 (1993); Pak et al., *Soc. for Neuroscience Abs.*, 20:149.2 (1994); White, *Soc. Neurosci. Abs.*, 20:308.9 (1994); and Firestein et al., *J. Immunology* 154:326-34 (1995). These publications in general show that adenosine kinase inhibitors, as a class, have a role in brain functions, and show promise in connection with the treatment of neurological conditions such as seizures. One reference, Phillis et al., indicates that the known adenosine kinase inhibitor 5-iodotubercidin apparently does not protect against ischemic cerebral injury. Keil et al. disclose that adenosine kinase plays a key role in the mediation of nervous system responses to stimulus, particularly pain (antinociception), but notes that the control of endogenous adenosine concentrations by such means is a complex process requiring further study.

Thus, there is a need for selective, potent, and bioavailable adenosine kinase inhibitors with a useful half-life, i.e. compounds which can be exploited to beneficially influence or control endogenous adenosine kinase activity, and therefore, extracellular adenosine levels. The compounds of the invention are suitable adenosine kinase inhibitors having these characteristics.

SUMMARY OF THE INVENTION

The invention is directed to novel nucleoside analogs which comprise a ribofuranosyl or lyxofuranosyl moiety linked to an aryl substituted 4-amino pyrrolo[2,3-d] pyrimidine or pyrazolo[3,4-d] pyrimidine nucleoside. Preferred compounds are 4-arylamino-5-aryl pyrrolo pyrimidines and 3-aryl4-arylamino pyrazolo pyrimidines with at least one aryl further substituted with a group that enhances water solubility. Suitable water solubilizing groups include amino-containing alkyl groups, guanidino and amidino containing groups, or other groups containing a basic nitrogen.

It has been discovered that these compounds are advantageously water soluble, and are highly selective adenosine kinase inhibitors with potencies significantly higher than other known adenosine kinase inhibitors. The compounds are also nontoxic, particularly in connection with liver function.

The invention concerns the compounds themselves, the preparation of these compounds, and the in vitro and in vivo adenosine kinase inhibition activity of these compounds. Another aspect of the invention is directed to the clinical use of the compounds to increase adenosine concentrations in biological systems. For example, in vivo inhibition of adenosine kinase prevents phosphorylation of adenosine resulting in higher local concentrations of endogenous adenosine.

The compounds of the invention possess advantages for pharmaceutical use such as enhanced pharmacological selectivity, efficacy, bioavailability, ease of manufacture, compound stability and ease of formulation for intravenous administration.

The compounds of the invention may be used clinically to treat medical conditions where an increased localized adenosine concentration is beneficial. Accordingly, the invention is directed to the treatment of ischemic conditions such as stroke, as well as other conditions benefitted by enhanced adenosine levels, such as inflammation, arthritis, seizures, epilepsy and other neurological conditions. The compounds are also useful for treating pain, as muscle relaxants, and for inducing sleep.

The invention is also directed to prodrugs and pharmaceutically acceptable salts of the compounds described, and to pharmaceutical compositions suitable for different routes of drug administration and which comprise a therapeutically effective amount of a described compound admixed with a pharmacologically acceptable carrier.

Definitions

The following terms generally have the following meanings.

The term "aryl" refers to aromatic groups, which have at least one ring having a conjugated pi electron system, including for example carbocyclic aryl, heterocyclic aryl and biaryl groups, all of which may be optionally substituted. Carbocyclic aryl groups are groups wherein all the ring atoms on the aromatic ring are carbon atoms, such as phenyl. Also included are optionally substituted phenyl groups, being preferably phenyl or phenyl substituted by one to three substituents, preferably lower alkyl, hydroxy, lower alkoxy, lower alkanoyloxy, halogen, cyano, perhalo lower alkyl, lower acylamino, lower alkoxycarbonyl, amino, alkylamino, carboxamido, and sulfamido.

Heterocyclic aryl groups are groups having from 1 to 3 heteroatoms as ring atoms in the aromatic ring and the remainder of the ring atoms carbon atoms. Suitable heteroatoms include oxygen, sulfur, and nitrogen, and include furanyl, thienyl, pyridyl, pyrrolyl, pyrimidyl, pyrazinyl, imidazolyl, and the like, all optionally substituted.

Optionally substituted furanyl represents 2- or 3-furanyi or 2- or 3-furanyl preferably substituted by lower alkyl or halogen. Optionally substituted pyridyl represents 2-, 3- or 4-pyridyl or 2-, 3- or 4-pyridyl preferably substituted by lower alkyl or halogen. Optionally substituted thienyl represents 2- or 3-thienyl, or 2- or 3-thienyl preferably substituted by lower alkyl or halogen.

The term "biaryl" represents phenyl substituted by carbocyclic aryl or heterocyclic aryl as defined herein, ortho, meta or para to the point of attachment of the phenyl ring, advantageously para; biaryl is also represented as the —$C_6H_4$—Ar substituent where Ar is aryl.

The term "aralkyl" refers to an alkyl group substituted with an aryl group. Suitable aralkyl groups include benzyl, picolyl, and the like, and may be optionally substituted.

The term "lower" referred to herein in connection with organic radicals or compounds respectively defines such with up to and including 7, preferably up to and including 4 and advantageously one or two carbon atoms. Such groups may be straight chain or branched.

The terms (a) "alkyl amino", (b) "arylamino", and (c) "aralkylamino", respectively, refer to the groups —NRR' wherein respectively, (a) R is alkyl and R' is hydrogen, aryl or alkyl; (b) R is aryl and R' is hydrogen or aryl, and (c) R is aralkyl and R' is hydrogen or aralkyl.

The term "acylamino" refers to RC(O)NR'.

The term "carbonyl" refers to —C(O)—.

The term "carboxamide" or "carboxamido" refers to —CONR$_2$ wherein each R' is independently hydrogen, lower alkyl or lower aryl.

The term "alkyl" refers to saturated aliphatic groups including straight-chain, branched chain and cyclic groups, optionally containing one or more heteroatoms.

The term "alkenyl" refers to unsaturated alkyl groups which contain at least one carbon-carbon double bond and includes straight chain, branched chain and cyclic groups, optionally containing one or more heteroatoms.

The term "alkynyl" refers to unsaturated alkyl groups which contain at least one carbon-carbon triple bond and includes straight chain, branched chain and cyclic groups, optionally containing one or more heteroatoms.

The term "amidino" refers to —C(NR$_1$)NR$_2$R$_3$, where R$_1$, R$_2$, and R$_3$ are independently hydrogen, alkyl or aryl groups.

The term "amidoximo" refers to —C(NOH)NH$_2$.

The term "mercapto" refers to SH or a tautomeric form thereof.

The term "alkylene" refers to a divalent straight chain or branched chain saturated aliphatic radical.

The term "sulfonamido" means —SO$_2$NHR where R is hydrogen or lower alkyl.

The term "N-sulfonyl amine" means —NHSO$_2$R where R is fluoro, lower perfluoroalkyl or lower alkyl.

The term "N-acylated sulfonamide" refers to the group —SO$_2$NHCOR where R is lower alkyl or lower perfluoroalkyl.

The term "guanidino" refers to the group —NR$_1$C(NR$_2$)NR$_3$R$_4$ where R$_1$, R$_2$, R$_3$ and R$_4$ are independently hydrogen, alkyl or aryl groups.

The term "aminoguanidino" refers to the group —NR$_1$NR$_2$C(NR$_3$)NR$_4$R$_5$ where R$_1$, R$_2$, R$_3$, R$_4$ and R$_5$ are independently hydrogen, alkyl or aryl groups.

The term "ureido" refers to the group —NR$_1$C(O)NR$_2$R$_3$ where R$_1$, R$_2$ and R$_3$ are independently hydrogen, alkyl or aryl groups.

The term "carboxylic acid" refers to the group —COOH.

The term "acylguanidino" refers to the group —CONR$_1$C(NR$_2$)NR$_3$R$_4$ where R$_1$, R$_2$, R$_3$ and R$_4$ are independently hydrogen, alkyl or aryl groups.

The term "basic nitrogen" generally refers to the nitrogen atom of an alkyl amine and implies a compound whose conjugated acid in aqueous solution has a pKa in the range of 9 to 11.

The term "prodrug" refers to any compound that may have less intrinsic activity than the "drug" but when administered to a biological system generates the "drug" substance either as a result of spontaneous chemical reaction or by enzyme catalyzed or metabolic reaction. Reference is made to various prodrugs such as acyl esters, carbonates, and urethanes, included herein as examples. The groups illustrated are exemplary, not exhaustive and one skilled in the art could prepare other known varieties of prodrugs. Such prodrugs of the compounds of the invention, fall within the scope of the invention.

The term "pharmaceutically acceptable salt" includes salts of compounds described herein derived from the combination of a compound of this invention and an organic or inorganic acid. The compounds of the present invention are useful in both free base and salt form. In practice the use of salt form amounts to use of base form; both forms are within the scope of the present invention.

The term "treatment" includes prophylatic or therapeutic administration of compounds of the invention, for the cure or amelioration of disease or symptoms associated with disease, and includes any benefit obtained or derived from the administration of the described compounds.

A water solubilizing group is a group that increases the solubility of the inhibitor by a factor of at least 10 and preferably of 100 at pH values suitable for intravenous administration (pH 3.5 to 10).

DETAILED DESCRIPTION OF THE INVENTION

Figure 1:
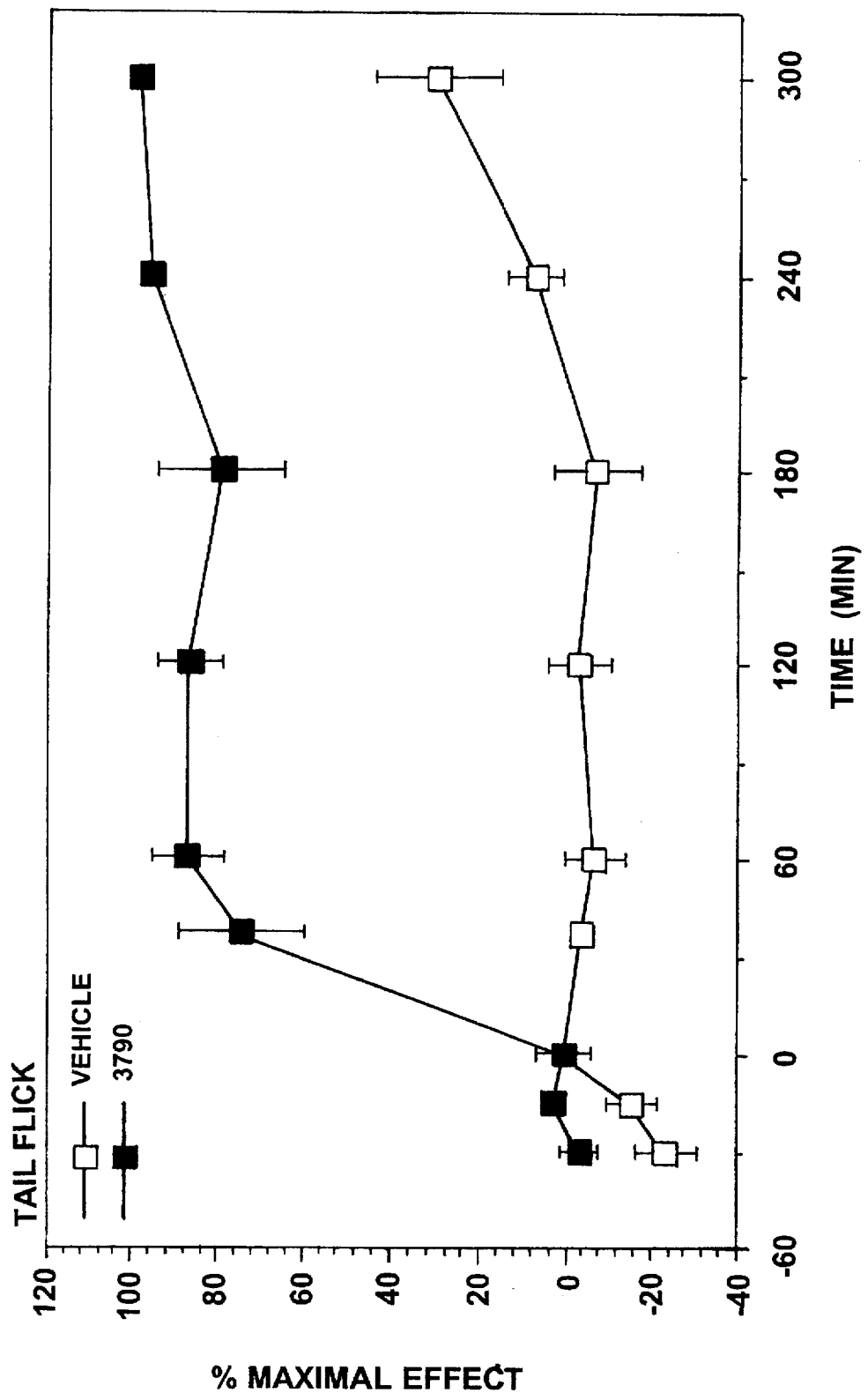
FIG. 1 shows the effects of administering compound #3 to test animals on the animals' responses to the tail flick test.

The invention relates to adenosine kinase inhibitors, and their pharmaceutically acceptable salts, of the general Formula I.

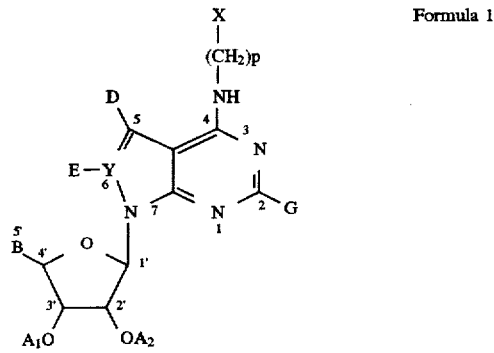

Formula 1 wherein:

A$_1$ and A$_2$ are each hydrogen or acyl, or together form a cyclic carbonate;

B is CH$_3$, alkenyl, or (CH$_2$)$_n$—B', where n is from 1 to 4 and B' is hydrogen, hydroxy, alkyl, alkoxy, amino, azido, halogen, or alkenyl;

D is halogen, alkyl, alkenyl, alkynyl, haloalkyl, cyano, carboxamido, or (CH$_2$)$_q$X where q is from 0 to 3 and each X is independently an aryl group, more preferably an aromatic ring optionally containing a nitrogen, sulfur, or oxygen atom optionally substituted at any position by halogen, alkyl, alkoxy, substituted per halo lower alkyl, sulfonamide, cyano, CONRR' where R and R' are independently hydrogen or lower alkyl, or is a water solubilizing group (CH$_2$)$_r$T where r is from 0 to 3 and T is an alkyl or alkenyl chain of 0 to 16 carbon atoms containing a carboxylic acid and optionally containing one or more nitrogen atoms and optionally one or more oxygen atoms, a 5- or 6-membered nitrogen containing heterocyclic aryl group, N-sulfonylated amino, amidoximo, N-aminoguanidino, amidino, guanidino, acylguanidino, cyclic derivatives of amidines and guanidines, acylated sulfonamide, a 5 or 6 membered alicyclic ring containing a basic nitrogen and optionally one or more oxygen atoms or $CONR_2R_3$ where at least one of $R_2$ and $R_3$ contains an alkyl chain containing one or more basic nitrogen atoms and optionally oxygen or taken together form a 5- or 6-membered ring containing at least one basic nitrogen.

Y is carbon or nitrogen; and E is nothing when Y is nitrogen, and is hydrogen or halogen when Y is carbon; G is hydrogen or halogen; p is from 0 to 3, preferably 0; provided at least one X includes a water solubilizing group as defined above or a nitrogen containing heterocycle.

For convenience, the numbering scheme in Formula 1 is given for pyrrolo pyrimidine compounds (Y=C). It will be understood that the nomenclature and numbering scheme is different for the pyrazolo pyrimidine (Y=N) embodiments of the invention.

The compounds of the invention are potent and water soluble adenosine kinase inhibitors, and are suitably non-toxic.

Preferably, X is a substituted six member ring (phenyl) or a nitrogen-containing heterocyclic aryl. The most preferred substitution is at position 4, and the preferred water solubilizing substituents (T) are an alkyl or alkenyl chain of 1 to 16 carbon atoms containing one or more nitrogen atoms and optionally containing one or more oxygen atoms or a 5 or 6 membered alicyclic ring containing nitrogen or $CONR_2R_3$ where $R_2$ and $R_3$ are as defined above, or guanidino containing groups, or amidino containing groups, or aminoguanidino containing groups or 5- or 6-membered nitrogen containing heterocyclic aryl groups. In theory, substitution of the ring structure as described, for example at the para position of a phenylamino group (i.e. 4-N-(4-substituted phenyl)amino) provides enhanced water solubility which in turn makes the compounds advantageous for administration to an animal.

Also preferred are embodiments where G, $A_1$ and A2 are hydrogen, B is $CH_2OH$, $CH_2NH_2$ and most preferably $CH_3$. D is preferably aryl (q=0), most preferably phenyl or phenyl substituted with $(CH_2)_rT$, where r is from 0 to 3 and T is as defined above. E is preferably hydrogen when Y=C.

Another aspect of the invention covers compounds with water solubilizing groups T such as sulfonic acid, carboxylic acid, squaric acid derivatives, 5-tetrazolyl and other bioisosteric replacements of a carboxylic acid group such as, but not limited to, those described in Carini et al., J. Med. Chem. 34, 2525 (1991) and references cited therein.

In another embodiment, preferred compounds are diaryls, meaning compounds of Formula 1 where D is $(CH_2)_qX$, both X groups are independently an optionally substituted carbocyclic or heterocyclic aryl, preferably with 5 or 6 atoms in the ring. At least one X group includes water solubilizing groups or substituents, as defined above.

Prodrugs of these compounds are within the scope of this invention. Prodrugs may be prepared by esterification of the hydroxyl groups on the ribofuranose or lyxofuranose ring. Specially preferred will be the ester derivatives that further improve the water solubility properties of the resulting prodrug. The compounds of the invention also contain asymmetric carbon atoms and can exist as stereoisomers, i.e. enantiomers and diastereomers. Individual stereoisomers and mixtures thereof are within the scope of the invention.

Thus, the 5'-modified 1-β-D-ribofuranosyl isomer is preferred; however the lyxofuranosyl form of these compounds (Formula 1) are within the scope of the invention.

Synthesis of Adenosine Kinase Inhibitors

The compounds of the invention can be made by several methods and for convenience can be grouped as pyrrolo or pyrazolo pyrimidines. Exemplary synthetic routes are given below.

Synthesis of Pyrrolo Pyrimidines

The pyrrolo pyrimidines of this invention have been synthesized by preparation of aryl-functionalized nucleosides, which at different stages are manipulated in order to incorporate water solubilizing groups as illustrated in the examples. As it will be clear to one skilled in the art, a number of sequences is available for the required functional group manipulations and the examples below are only an illustration of the manner in which such transformations can be carried out.

EXAMPLE 1

Preferred Synthesis of Pyrrolo Pyrimidines

Water soluble diaryl pyrrolo[2,3-d]pyrimidine nucleosides of the invention can be made according to the routes outlined in Schemes 1 and 2. The heterocycle, 5-aryl4-arylaminopyrrolo[2,3-d]pyrimidine (Scheme 1) is made starting from a substituted phenacyl chloride or bromide by reaction with potassium phthalimide in a solvent such as N,N-dimethylformamide or acetonitrile at ambient temperature. The resulting phenacylphthalimide (3) is condensed with malononitrile in the presence of sodium methoxide to provide the 2-amino-3-cyano-4-arylpyrrole intermediate (4). Refluxing (4) with triethyl orthoformate leads to intermediate (5).

Water solubilizing groups can be incorporated at this point by reaction of (5) with an aniline which contains a desired water solubilizing group, as in Example 2B. Alternatively, the aniline may be substituted with a group that is amenable to modification, as in Example 2C. Intermediates obtained in this manner can be manipulated at later stages by well known methods. (e.g. Example 4). The desired 5-substituted-5-deoxy ribose analogs are prepared by tosylation of a suitably protected ribose, displacement of the tosylate by appropriate nucleophiles, such as hydride or azido, and subsequent deblocking (Scheme 4). Snyder, J: Serianni, A; Carbohydrate Research 163:169(1987).

SCHEME 1

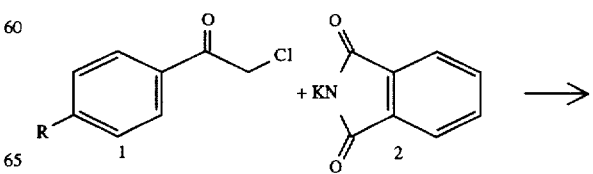

-continued
SCHEME 1

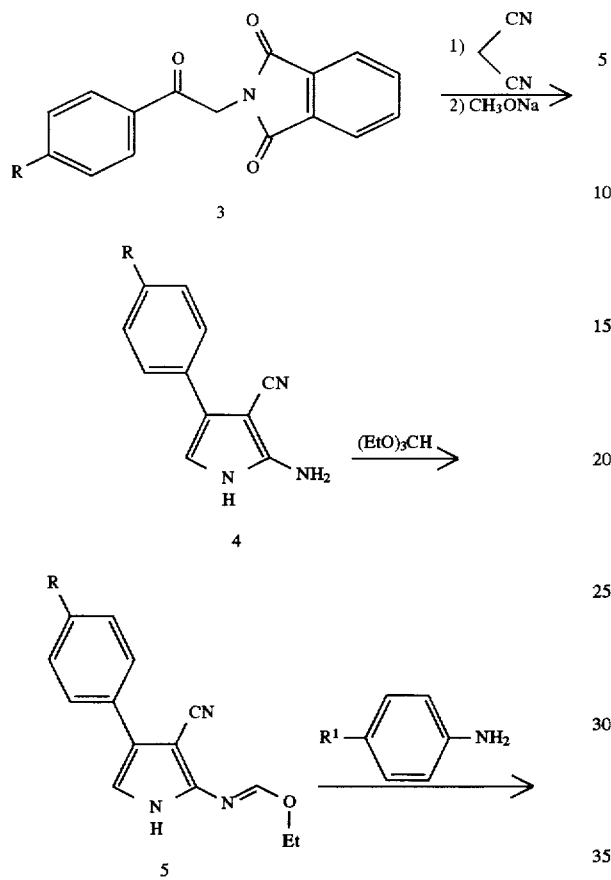

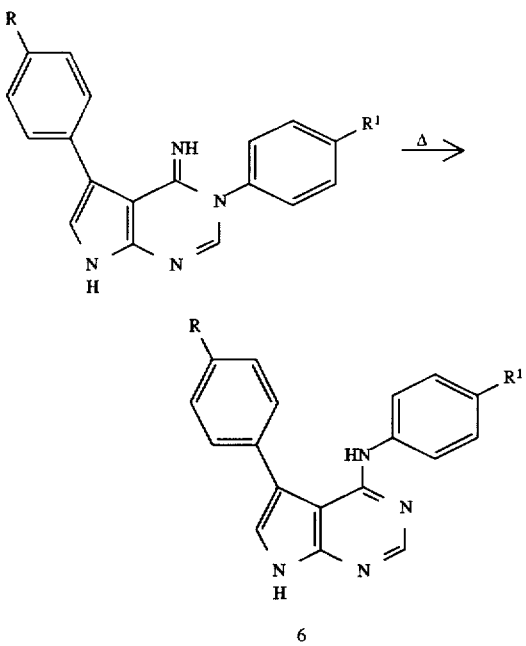

The required 1-alpha-chloro-5-deoxy-5-modified-2,3-isopropylidene-D-ribofuranose (7) is generated by reacting a sugar such as (8) with CCl₄ and HMPT at 0° C. in toluene. Wilcox, C: Otaski, R; Tetrahedron Lett, 27:1011(1986) (Scheme 2). Reaction of (7) with the heterocycle (6) in the presence of KOH and a phase transfer catalyst such as TDA-1 at ambient temperature results in the formation of a protected

SCHEME 2

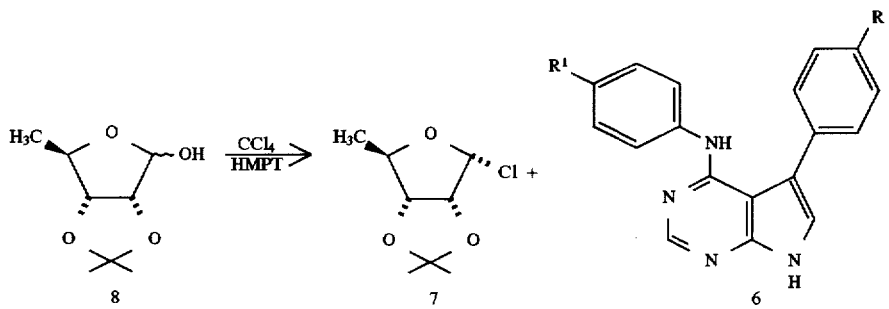

-continued
SCHEME 2

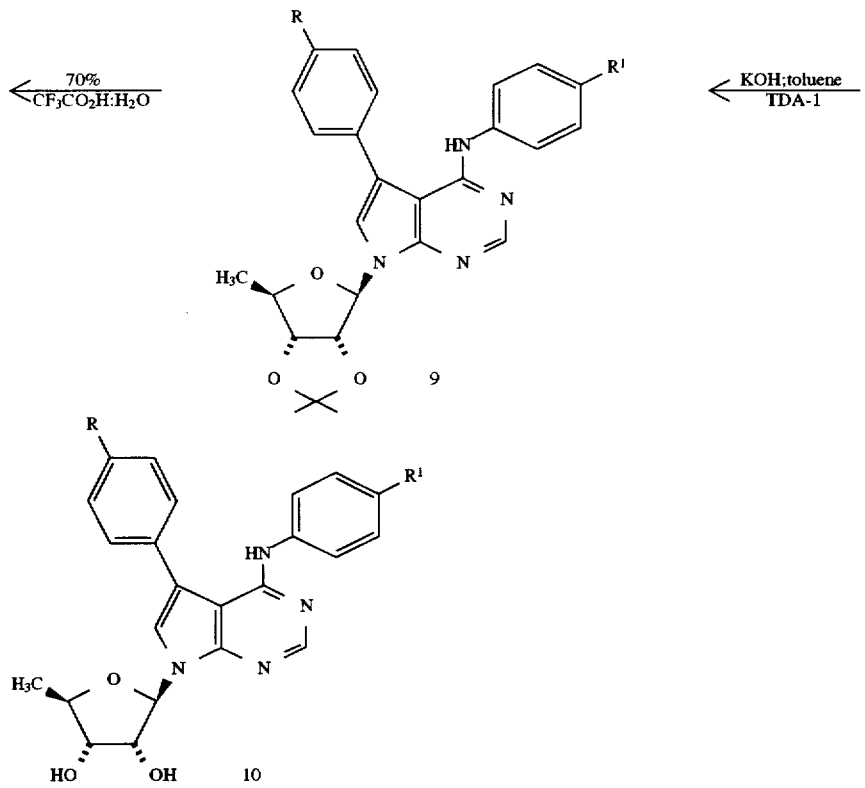

nucleoside (9) Rosemeyer, H; Seela, F; Helvetica Chimica Acta, 71, 1573(1988). Deprotection under acidic conditions leads to the target compound (10).

The following compounds were made by this route.
1) 4-N-(4-(N,N-Dimethylaminomethyl)phenyl)amino-5-phenyl-7-(5-deoxy-β-D-ribofuranosyl)pyrrolo[2,3-d]pyrimidine.
2) 4-N-(4-(2-Hydroxyethyl)phenyl)amino-5-phenyl-7-(5-deoxy-β-D-ribofuranosyl)pyrrolo[2,3-d]pyrimidine.

Other dialkylamino substituted adenosine kinase inhibitors were synthesized by reacting 4-(4-(2-hydroxyethyl)phenyl)amino-5-phenyl-7-(5-deoxy-2,3-O-isopropylidene-1-β-D-ribofuranosyl)pyrrolo[2,3-d]pyrimidine with methyl triphenoxyphosphonium iodide to provide 4-N-(2-iodoethylphenyl)amino-5-phenyl-7-(5-deoxy-β-D-ribofuranosyl)pyrrolo[2,3-d]pyrimidine. Displacement of the iodide with appropriate amines followed by acetonide group removal led to the final product compounds:

3) 4-N-[4-(2-(4-morpholino)ethyl)phenyl]amino-5-phenyl-7-(5-deoxy-β-D-ribofuranosyl)pyrrolo[2,3-d]pyrimidine.
4) 4-N-[4-(2-(1-piperazino)ethyl)phenyl]amino-5-phenyl-7-(5-deoxy-β-D-ribofuranosyl)pyrrolo[2,3-d]pyrimidine.
5) 4-N-[4-(2-(2-N,N-diethylaminoethyleneamino)ethyl)phenyl]amino-5-phenyl-7-(5-deoxy-β-D-ribofuranosyl)pyrrolo[2,3-d]pyrimidine.
6) 4-N-[4-(2-N,N-diethylaminoethyl)phenyl]amino-5-phenyl-7-(5-deoxy-β-D-ribofuranosyl)pyrrolo[2,3-d]pyrimidine.
7) 4-N-[4-(2-N,N-dimethylaminoethyl)phenyl]amino-5-phenyl-7-(5-deoxy-β-D-ribofuranosyl)pyrrolo[2,3-d]pyrimidine.

Synthesis of 4-N-(4-(2-aminoethyl)phenyl)amino-5-phenyl-7-(5-deoxy-β-D-ribofuranosyl)pyrrolo[2,3-d] pyrimidine was achieved by subjecting the intermediate 4-N-(4-(2-hydroxyethyl)phenyl)amino-5-phenyl-7-(5-deoxy-2,3-O-isopropylidene-β-D-ribofuranosyl)pyrrolo[2,3-d]pyrimidine to a Mitsunobu amination reaction using triphenyl phosphine, diisopropyl diazodicarboxylate and phthalimide. The resulting phthalimido derivative was treated with hydrazine hydrate followed by deblocking with 70% trifluoroacetic acid to yield the final product.

EXAMPLE 2

Diaryl Pyrrolopyrimidine Nucleosides
A. 2-Amino-3-cyano-4-phenylpyrrole, (4).

To a solution of phenacyl chloride (1) (500 g, 3.23 mol) in dry N,N-dimethylformamide(600 mL) was added potassium phthalimide, (2) (600 g, 3.23 mol) in small portions (Scheme 1). The resulting mixture was stirred at ambient temperature overnight. To this was added malononitrile (256 g, 3.88M) in one lot followed by a 25 wt % solution of sodium methoxide in methanol (744 mL, 3.2 mol). The resulting mixture was stirred at room temperature overnight. Ice-water (10.0 L) was added to the reaction mixture and stirring was continued at room temperature overnight. The precipitate formed was collected by filtration and washed with cold water (4.0 L). The off-white solid was stirred in toluene (3.0 L) and filtered. The solid was washed with toluene (300 mL) and dried under vacuum at 60° C. overnight. Yield 298.56 g. m.p. 172°–174° C.

B. 4-N-(4-N,N-Dimethylaminomethylphenyl)amino-5-phenylpyrrolo[2,3-d]pyrimidine (6).

A mixture of (4) (3.66 g, 20 mmol) and triethyl orthoformate (25 mL) was refluxed for 1 h. The triethyl orthoformate was distilled off under reduced pressure until the pot temperature reached 88° C. To the cooled reaction mixture hexane (100 mL) was added under vigorous stirring. The contents of the vessel were cooled to 0° C. and the off white solid formed was collected by filtration and washed with hexane (2×50 mL) and dried under suction. Final drying was done in a high vacuum oven. Yield of the 2-ethoxymethylene-3-cyano-4-phenylpyrrole (5) was 3.68 g. (m.p. 208°–209° C.)

The above material (3.67 g) was dissolved in dry N,N-dimethylformamide and 4-N,N-dimethylaminomethylaniline (5.2 g 35 mmol) was added, and the reaction mixture was heated to reflux for 1 h. Water (20 mL) was added and refluxing was continued overnight. Upon cooling to 0° C. the title compound precipitated as a brown solid which was collected by filtration and dried under vacuum. The product was crystallized from boiling ethyl acetate to provide the title compound (6). Yield 5.0 g. m.p. 208°–209° C.

C. 4-N-(4-Hydroxyethylphenylamino)-5-phenyl-pyrrolo [2,3-d]pyrimidine

This compound was made by a procedure similar to the one given for (6) except that 4-N,N-dimethylaminomethylaniline was replaced with 4-hydroxyethylaniline. m.p. 178°–179° C.

D. 4-N-(4-Carbethoxymethylphenyl)amino-5-phenylpyrrolo[2,3-d]pyrimidine

This compound was made by a procedure similar to the one described for 4-N-(4-N,N-dimethylaminomethylphenyl)amino-5-phenylpyrrolo[2,3-d] pyrimidine (6) except that 4-N,N-dimethylaminomethylaniline was replaced with ethyl 4-aminophenylacetate. m.p. 180°–183° C.

E. 4-N-(4-(2-(1-piperazino-4-t-butoxycarbonyl)ethyl) phenyl)amino-5-phenylpyrrolo[2,3-d]pyrimidine This compound was prepared in two steps from 4-N-(4-(2-hydroxyethyl)phenyl)amino-5-phenylpyrrolo[2,3-d] pyrimidine: Iodination with methyl triphenoxyphosphonium iodide, followed by reaction of the iododerivative obtained with 1-t-butoxycarbonylpiperazine in refluxing dioxane to afford the title compound. HNMR (200 MHz; DMSO-$d_6$): 8.32 (1H, s), 7.2–7.6 (8H, m), 7.13 (2H, d, J=8.5 Hz), 3.29 (4H, m), 2.36 (4H, m), 1.38 (9H, s)

EXAMPLE 3

Glycosylation of Pyrrolopyrimidine Heterocycles

The procedure described here for the glycosylation of 4-N-(4-N,N-dimethylaminomethyl)phenyl)amino-5-phenylpyrrolo[2,3-d]pyrimidine (6) typifies a general method of glycosylation for many pyrrolopyrimidine heterocycles.

Into a 250 mL three neck flask fitted with a thermometer, an addition funnel and a mechanical stirrer, was taken a mixture of toluene (15.0 mL), 5-deoxy-2,3-isopropylidene-D-ribofuranose (1.7 g, 10 mmol) and carbon tetrachloride (1.2 mL). The reaction mixture was cooled to −12° C. by immersing the flask into a dry ice-acetone mixture. To it was added dropwise through the addition funnel hexamethylphosphorous triamide (2.2 ml) over a period of 10 min. After the addition was completed the mixture was stirred at −10° C. for 15 min and the contents were transferred to a separatory funnel, extracted with ice cold water (1×25 mL), and the organic layer was dried over magnesium sulfate. The drying agent was removed by filtration and the filtrate was added directly to an already stirring mixture of the heterocycle (6) (1.7 g, 5 mmol), KOH (0.6 g), and TDA-1 in toluene at room temperature. Completion of the reaction was evidenced by the absence of the heterocycle on t.l.c. ($SiO_2$, 9:1 dichloromethane-methanol). The reaction mixture was transferred to a separatory funnel and extracted with water (1×25 mL). The organic layer was evaporated and the residue was purified by flash chromatography over $SiO_2$ using 19:1 methylene chloride-methanol as eluting solvent. The fast moving spot was collected and identified to be 4-N-(N,N-dimethylaminomethylphenyl)amino-5-phenyl-7-(5-deoxy-2,3-isopropylidene-β-D-ribofuranosyl)pyrrolo(2, 3-d)pyrimidine (9). This product was dissolved in 70% trifluoroacetic acid and stirred at room temperature for two hours. Volatiles were evaporated under reduced pressure and the residue was coevaporated with water (2×20 mL) and with ethanol (1×20 mL). The resulting product was dissolved in water (25 mL) and neutralized with saturated sodium bicarbonate solution. The mixture was extracted with ethyl acetate (5×25 mL). Organic layers were combined, dried and evaporated. The semi solid residue was crystallized from boiling ethyl acetate to give compound #1. Yield 400 mg. m.p. 108°–109° C.

EXAMPLE 4

Alternative Synthesis of Pyrrolo Pyrimidines

Compounds of the invention can also be made according to the methods described in Browne et al., Ser. No. 08/812, 916, which is incorporated by reference.

Briefly, reaction of 4-chloro-5-iodo-7-(5-deoxy-1-β-D-ribofuranosyl) pyrrolo[2,3-d]pyrimidine (11) with an amine in refluxing ethanol leads to the formation of a 4-(N-substituted)amino-5-iodo-7-(5-deoxy-1-β-D-ribofuranosyl) pyrrolo[2,3-d]pyrimidine (12). This iodo compound is treated with an aryl boronic acid in the presence of a palladium catalyst to generate the targeted 4-(N-substituted) amino-5-aryl-7-(5-deoxy- 1-β-D-ribofuranosyl)pyrrolo[2,3-d]pyrimidine, which is purified by chromatography and/or recrystallization from a suitable solvent.

For example, the synthesis of 8) 4-N-(4-N-trifluoromethanesulfonylaminophenyl)amino-5-phenyl-7-(5-deoxy-1-β-D-ribofuranosyl) pyrrolo(2,3-d)pyrimidine (16)

(Scheme 3) illustrates several aspects of the above procedure. The formation of a 4-N substituted amine is exemplified by the preparation of 4-N-(4-N-acetylaminophenyl) amino-5-iodo-7-(5-deoxy-2,3-O-isopropylidene-1-β-D-ribofuranosyl)pyrrolo(2,3-d)pyrimidine (Example 5H). The incorporation of an aryl group is illustrated in Example 5I by the preparation of 4-N-(4-N-acetylaminophenyl)amino-5-phenyl-7-(5-deoxy2,3-O-isopropylidene-1-β-D-ribofuranosyl) pyrrolo(2,3-d)pyrimidine. The latter has a functional group (N-acetyl) which can be modified in order to enhance the water solubility of the target molecule by a three step sequence: (I) deacetylation under strongly basic conditions, (ii) reaction of the resulting aniline with trifluoromethane sulfonic anhydride in dichloromethane at −78° C., in order to incorporate the water solubilizing group and, (iii) removal of the isopropylidene protecting group under acidic conditions.

Another example of a functional group modification leading to enhanced solubility properties is the preparation of 4-N-(4-guanidinophenyl)amino-5-phenyl-7-(5-deoxy-1-β-D-ribofuranosyl)pyrrolo(2,3-d)pyrimidine by reaction of 4-N-(4-aminophenyl)amino-5-phenyl-7-(5-deoxy-2,3-O-isopropylidene-1-β-D-ribofuranosyl)pyrrolo(2,3-d) pyrimidine (Scheme 3,14) with aminoiminomethane sulfonic acid followed by deprotection of the diol under acidic conditions.

SCHEME 3

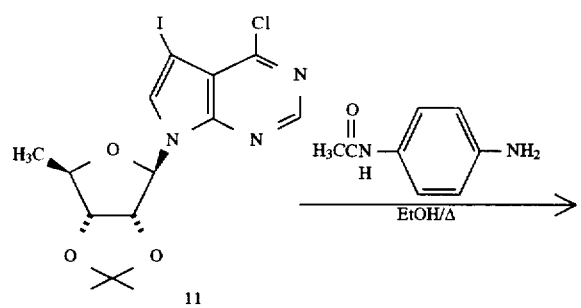

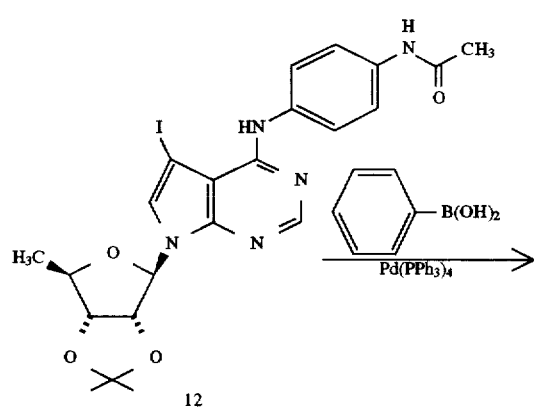

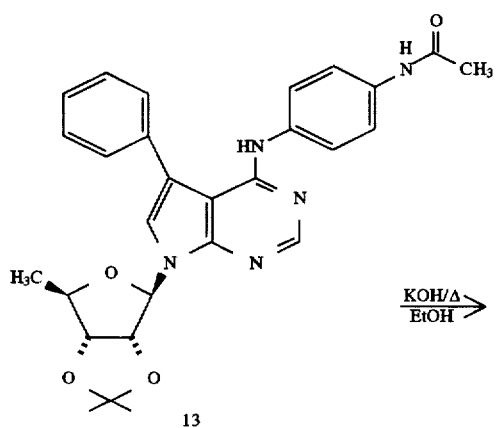

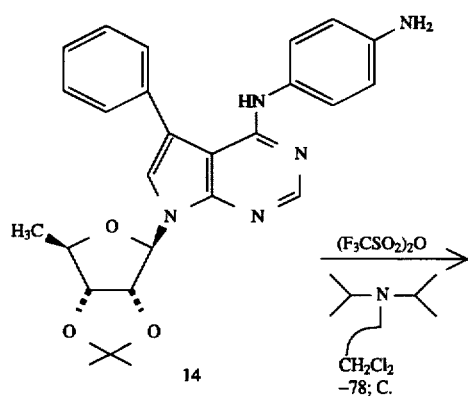

-continued
SCHEME 3

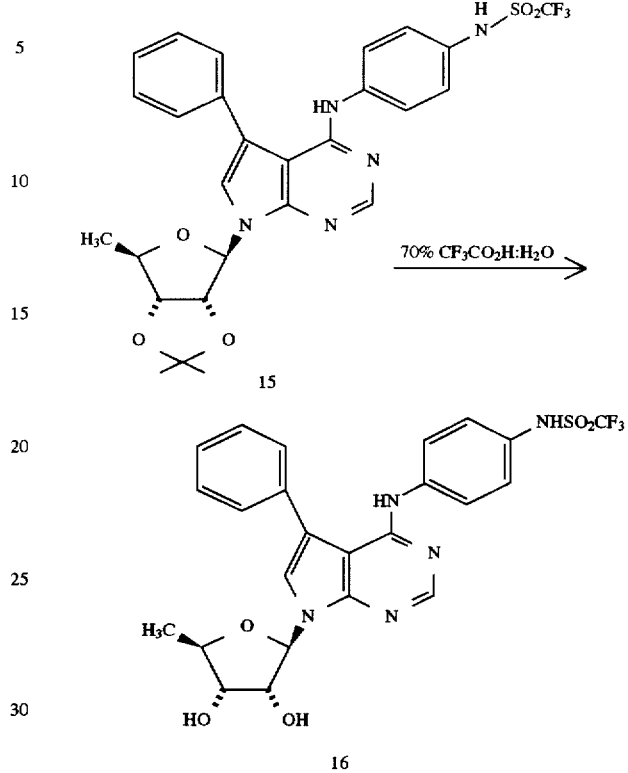

In another instance, a nitrile group can be converted to an amidine or an amidoxime group by procedures which are well established in the literature (Gabrielson et al., J. Med. Chem. 35, 3231(1992), Alig et al, J.Med.Chem 35, 4393 (1992), or Stanek et al J. Med. Chem. 36, 2168 (1993); J. Med. Chem. 36, 46 (1993)), as indicated by the conversion of 4-N-(4-cyanophenyl)amino-5-phenyl-7-(5-deoxy-2,3-O-isopropylidene-1-β-D-ribofuranosyl) pyrrolo(2,3-d) pyrimidine into 4-N-(4-amidinophenyl)amino-5-phenyl-7-(5-deoxy-1-β-D-ribofuranosyl)pyrrolo(2,3-d)pyrimidine or 4-N-(4-amidoximephenyl)amino-5-phenyl-7-(5-deoxy-1-β-D-ribofuranosyl)pyrrolo( 2,3-d)pyrimidine or 4-N-(4-amidoximephenylamino-5-phenyl-7-(5-deoxy-1-β-D-ribofuranosyl)pyrrolo(2,3-d)pyrimidine (Example 5.O).

Guanidino derivatives can be prepared from the corresponding amino or hydroxy compounds by application of methods described in the literature such as, but not limited to, the procedures described by Miller and Bischoff (Synthesis 778 (1986)), Dodd and Kozikowski (Tetrahedron Lett. 35, 977 (1994)), Beatty and Magrath (J. Chem. Soc. 12 (1965)), Larson et al (Int J. Pept. Protein Res. 9, 182(1977)), Brand and Brand (Org. Synth. 22, 59 (1942)), Ichikawa (Tetrahedron Lett 29, 4957(1988)), Katritzky et al (Synth. Commun. 25, 1173 (1995)), Ariga and Anslyn (J.Org. Chem. 57, 417(1992)) or Palát et al (Collect. Czech. Chem. Commun. 57, 1127 (1992)).

Acylguanidines can be prepared by methods described in the literature such as, but not limited to, the methods described by, Bock et al (J. Med. Chem. 29, 1540 (1986)) and references cited therein.

Similarly, L-lyxofuranosyl analogs can be synthesized by the above procedures where the ribofuranose intermediate is replaced with an appropriately protected L-lyxofuranose, as illustrated for the synthesis of 4-N-(4-(2-(1-piperazino)

ethyl)phenyl)amino-5-phenyl-7-(1-α-L-lyxofuranosyl) pyrrolo[2,3-d]pyrimidine (12). The following L-lyxofuranosyl analogs can be synthesized by obvious modifications of this procedure.

9) 4-N-(4-(N,N-dimethylaminomethyl)phenyl)amino-5-phenyl-7-α-L-lyxofuranosylpyrrolo[2,3-d]pyrimidine.
10) 4-N-(4-(2-hydroxyethyl)phenyl)amino-5-phenyl-7-α-L-lyxofuranosylpyrrolo[2,3-d]pyrimidine.
11) 4-N-[4-(4-morpholinoethyl)phenyl]amino-5-phenyl-7-α-L-lyxofuranosylpyrrolo[2,3-d]pyrimidine.
12) 4-N-[4-(1-piperazinoethyl)phenyl]amino-5-phenyl-7-α-L-lyxofuranosylpyrrolo[2,3-d]pyrimidine.
13) 4-N-[4-(2-N,N-diethylaminoethyleneaminoethyl) phenyl]amino-5-phenyl-7-α-L-lyxofuranosylpyrrolo[2,3-d]pyrimidine.
14) 4-N-[4-(2-N,N-diethylaminoethyl)phenyl]amino-5-phenyl-7-α-L-lyxofuranosylpyrrolo[2,3-d]pyrimidine.
15) 4-N-[4-(2-N,N-dimethylaminoethyl)phenyl]amino-5-phenyl-7-α-L-lyxofuranosylpyrrolo[2,3-d]pyrimidine.
16) 4-N-(4-(2-aminoethyl)phenyl)amino-5-phenyl-7-α-L-lyxofuranosylpyrrolo[2,3-d]pyrimidine.
17) 4-N-[4-(N-trifluoromethanesulfonylamino)phenyl] amino-5-phenyl-7-α-L-lyxofuranosylpyrrolo[2,3-d] pyrimidine.

EXAMPLE 5

Preparation of Representative Compounds

Preparation of the following representative compounds is described:

18) 4-N-[4-(2-tert-butyldimethylsilyloxyethyl)phenyl] amino-5-phenyl-pyrrolo[2,3-d]pyrimidine
19) 4-N-[4-(2-tert-butyldimethylsilyloxyethyl)phenyl] amino-5-phenyl-7-(5-deoxy-2,3-O-isopropylidene-β-D-ribofuranosyl)pyrrolo[2,3-d]pyrimidine
20) 4-N-[4-(2-hydroxyethyl)phenyl]amino-5-phenyl-7-(5-deoxy-β-D-ribofuranosyl)pyrrolo[2,3-d]pyrimidine
21) 4-N-[4-(2-hydroxyethyl)phenylamino-5-phenyl-7-(5-deoxy-2,3-isopropylidene-β-D-ribofuranosyl)pyrrolo[2,3-d]pyrimidine
22) 4-N-[4-(2-aminoethyl)phenyl]amino-5-phenyl-7-(5-deoxy-β-D-ribofuranosyl)pyrrolo[2,3-d]pyrimidine
23) 4-N-[4-(2-iodoethyl)phenyl]amino-5-phenyl-7-(5-deoxy-2,3-isopropylidene-β-D-ribofuranosyl)pyrrolo[2,3-d]pyrimidine
24) 4-N-[4-(2-(4-morpholino)ethyl)phenyl]amino-5-phenyl-7-(5-deoxy-β-D-ribofuranosyl)pyrrolo[2,3-d] pyrimidine.
25) 4-N-[4-(2-(1-piperazino)ethyl)phenyl]amino-5-phenyl-7-(5-deoxy-β-D-ribofuranosyl)pyrrolo[2,3-d]pyrimidine. m.p. 168°–170° C.
26) 4-N-[4-(2-(2-N,N-diethylamino)ethyl)phenyl]amino-5-phenyl-7-(5-deoxy-β-D-ribofuranosyl)pyrrolo[2,3-d] pyrimidine. m.p. 97°–99° C.
27) 4-N-[4-(2-(N,N-diethylaminoethyleneamino)ethyl) phenyl]amino-5-phenyl-7-(5-deoxy-β-D-ribofuranosyl) pyrrolo[2,3-d]pyrimidine hydrochloride m.p. 110°–12° C.
28) 4-N-[4-(2-(N,N-dimethylamino)ethyl)phenyl]amino-5-phenyl-7-(5-deoxy-β-D-ribofuranosyl)pyrrolo[2,3-d] pyrimidine. m.p. 145°–146° C.
29) 4-N-[4-(N-acetylamino)phenyl]amino-5-iodo-7-(1-β-D-5-deoxy-2,3-O-isopropylideneribose)pyrrolo[2,3-d] pyrimidine
30) 4-N-[4-(N-acetylamino)phenyl]amino-5-phenyl-7-(1-β-D-5-deoxy-2,3-O-isopropylideneribose)pyrrolo[2,3-d] pyrimidine
31) 4-N-(3-hydroxymethylphenyl)amino-5-phenyl-7-(5-deoxy-1-β-D-ribofuranosyl)-pyrrolo(2,3-d)pyrimidine
32) 4-N-(4-aminophenyl)amino-5-phenyl-7-(5-deoxy-1-β-D-2,3-O-isopropylideneribose)pyrrolo[2,3-d]pyrimidine
33) 4-N-[4-(N-trifluoromethanesulfonylamino)phenyl] amino-5-phenyl-7-(5-deoxy-1-β-D-ribose)pyrrolo[2,3-d] pyrimidine
34) 4-N-(4-cyanophenyl)amino-5-iodo-7(2,3-O-isopropylidene-5-deoxy-1-β-D-ribofuranosyl)pyrrolo[2,3-d]pyrimidine
35) 4-N-(4-cyanophenyl)amino-5-phenyl-7-(2,3-O-isopropylidene-5-deoxy-1-β-D-ribofuranosyl)pyrrolo[2,3-d]pyrimidine
36) 4-N-(4-amidoximephenyl)amino-5-phenyl-7-(2,3-O-isopropylidene-5-deoxy-1-β-D-ribofuranosyl)pyrrolo[2,3-d]pyrimidine
37) 4-N-(4-amidoximephenyl)amino-5-phenyl-7-(5-deoxy-1-β-D-ribofuranosylpyrrolo[2,3-d]pyrimidine hydrochloride
38) 4-N-(4-amidinophenyl)amino-5-phenyl-7-(2,3-O-isopropylidene-5-deoxy-1-β-D-ribofuranosyl)pyrrolo[2,3-d]pyrimidine
39) 4-N -(4-amidinophenyl)amino-5-phenyl-7-(5-deoxy-1-β-ribofuranosyl)pyrrolo[2,3-d]pyrimidine
40) 4-N-[4-(N-acetylaminosulfonyl)phenyl]amino-5-phenyl-7-(5-deoxy-1-β-D-ribofuranosyl)pyrrolo[2,3-d] pyrimidine
41) 4-N-(2-pyridylmethylamino)-5-iodo-7-(5-deoxy-1-β-D-ribofuranosyl)pyrrolo[2,3-d]pyrimidine A. Preparation of 4-N-[4-(2-tert-butyldimethylsilyloxyethyl)phenyl]amino-5-phenyl-pyrrolo[2,3-d] pyrimidine (18)

To a suspension of 4-N-(2-hydroxyethylphenyl)amino-5-phenyl-pyrrolo[2,3-d]pyrimidine (3.1 g, 9.4 mmol) and imidazole (1.27 g, 2 mmol) in dichloromethane (200 mL) was added a solution of tert-butyldimethylsilyl chloride (1.55 g, 10.3 mmol) in small portions over a 10 min period. The reaction mixture was stirred until there was no starting material seen on t.l.c. (SiO$_2$, 4:1 ethyl acetate-hexane). The reaction mixture was filtered and the solid was washed with methylene chloride (2×10 mL). The combined filtrate and washings were evaporated and chromatographed over SiO$_2$ using 4:1 ethyl acetate-hexane. Yield 3.3 g. m.p. 162°–165° C. Rf=0.5 in the above solvent.

B. Preparation of 4-N-[4-(2-tert-butyldimethylsilyloxyethyl)phenyl]amino-5-phenyl-7-(5-deoxy-2,3-O-isopropylidene-β-D-ribofuranosyl)pyrrolo[2,3-d]pyrimidine (19)

The above heterocycle was glycosylated with 5-deoxy-2,3-O-isopropylidene-D-ribose (7) by the procedure described earlier for the synthesis of (1), as in Example 1. The product was obtained as a glassy solid. H-NMR, DMSO-d$_6$:, 6.3 (d,1H, C$_1$, —H anomeric), 7.1–7.8 (M,10H, aromatics), 8.41 (S, 1H, C-2H) 2.7 and 3.75 (2t, 4H, CH$_2$—CH$_2$—O-side chain), and other sugar protons. Rf=0.75, silica, 4:1 Ethyl acetate:hexane.

C. Preparation of 4-N-[4-(2-hydroxyethylphenyl)]amino-5-phenyl-7-(5-deoxy-β-D-ribofuranosyl)pyrrolo[2,3-d] pyrimidine (20)

This compound was prepared by treating the above compound with 70% trifluoroacetic acid in water at room temperature and working up the reaction by the procedure described for the synthesis of (1). m.p. 221°–223° C. Rf=0.45 SiO$_2$, 9:1 CH$_2$Cl$_2$-methanol.

D. Preparation of 4-N-[4-(2-hydroxyethyl)phenyl]amino-5-phenyl-7-(5-deoxy-2,3-isopropylidene-β-D-ribofuranosyl) pyrrolo[2,3-d]pyrimidine (21).

To a solution of 4-N-[4-(2-tert-butyldimethylsilyloxyethyl)phenyl]amino-5-phenyl-7-(5- deoxy-β-D-ribofuranosyl)pyrrolo[2,3-d]pyrimidine (2.1 g) in dry THF (75 mL) was added 1M solution of tetrabutylammonium fluoride (5.0 mL) at 0° C. The reaction mixture was stirred at room temperature overnight. Solvent evaporated and residue was purified by chromatography over SiO$_2$ using 4:1 ethyl acetate-hexane. The product was obtained as a glassy solid. Rf=0.7 in the above solvent system.

E. Preparation of 4-N-[4-(2-aminoethyl)phenyl]amino-5-phenyl-7-(5-deoxy-β-D-ribofuranosyl)pyrrolo[2,3-d]pyrimidine (22)

To a stirred solution of a compound of 4-N-(2-hydroxyethylphenyl)amino-5-phenyl-7-(5-deoxy-2,3-isopropylidene-β-D-ribofuranosyl)pyrrolo[2,3-d]pyrimidine (Example 5C), (242 mg), phthalimide (110 mg) and triphenylphosphine (196 mg) in dry tetrahydrofuran (7.0 mL) diisopropyldiazodicarboxylate (0.16 mL) was added and stirred for 16 hours. Completion of the reaction was evidenced by the absence of the starting material on the t.l.c. Volatiles were evaporated and the residue was purified by chromatography on a SiO$_2$ gel column. The product thus obtained was dissolved in ethanol (10 mL) containing hydrazine (0.2 mL of 97%) and refluxed for 3 hours. The reaction mixture was cooled and filtered and the filtrate was evaporated to obtain a semi solid which was deblocked with methanol (5 mL) and 1N aq. HCl (5 mL) under refluxing conditions for 20 min. The reaction mixture was cooled and treated with 2N NaOH solution to adjust the pH to 8. The reaction mixture was extracted repeatedly with ethyl acetate (4×25 mL). The combined organic layers was dried over magnesium sulfate and evaporated to obtain an off white solid which was crystallized from boiling ethanol. Yield 115 mg, m.p. 192°–193° C.

F. Preparation of 4-N-[4-(2-iodoethyl)phenyl]amino-5-phenyl-7-(5-deoxy-2,3-isopropylidene-β-D-ribofuranosyl)pyrrolo[2,3-d]pyrimidine (23)

To a solution of 4-(2-hydroxyethylphenyl)amino-5-phenyl-7-(5-deoxy-2,3-isopropylidene-β-D-ribofuranosyl)pyrrolo[2,3-d]pyrimidine (1.0 g, 2.1 mmol) in methylene chloride (37 mL) methyl triphenoxyphosphonium iodide (2.05 g, 4.7 mmol) was added and stirred at room temperature. After two hours completion of the reaction was evidenced by t.l.c. (SiO$_2$, 2:1 hexane-ethyl acetate). The reaction was quenched with methanol (200 μL), extracted with 0.5M solution of sodium thiosulfate (20 mL) and with water (20 mL). The organic layer was dried over sodium sulfate and evaporated to obtain an oily residue which was purified by chromatography over SiO$_2$ using 4:1 hexane-ethyl acetate as eluting solvent to obtain the title compound as a glassy solid. Yield 1.4 g. T.I.C. SiO$_2$, 2:1 hexane-ethyl acetate, Rf=0.25.

G. Preparation of 4-N-[4-(2-(4-morpholino)ethyl)phenyl]amino-5-phenyl-7-(5-deoxy-β-D-ribofuranosyl)pyrrolo[2,3-d]pyrimidine (24)

A mixture of the above iodo compound of Example 5F (76 mg, 0.18 mmol), morpholine (0.1 mL) and dioxane (5 mL) was refluxed overnight. Volatiles were removed under high vacuum and the residue was chromatographed over silica gel using 19:1 hexane-ethyl acetate. The intermediate thus obtained was subjected to deblocking by gently refluxing it with methanol (2.0 mL) and 0.5N HCl solution (5.0 mL) for 30 min. The reaction mixture was cooled and the pH was adjusted to ~8 by adding 1M KHCO$_3$ solution. The precipitate was collected by filtration, washed with water, and dried in air. The product was crystallized from boiling ethyl acetate. Yield 30 mg. m.p. 95°–100° C.

The following compounds were also synthesized as described above:

25) 4-N-[4-(2-(1-piperazino)ethyl)phenyl]amino-5-phenyl-7-(5-deoxy-β-D-ribofuranosyl)pyrrolo[2,3-d]pyrimidine. m.p. 168°–170° C.

26) 4-N-[4-(2-(2-N,N-diethylamino)ethyl)phenyl]amino-5-phenyl-7-(5-deoxy-β-D-ribofuranosyl)pyrrolo[2,3-d]pyrimidine. m.p. 97°–99° C.

27) 4-N-[4-(2-(N,N-diethylaminoethyleneamino)ethyl)phenyl]amino-5-phenyl-7-(5-deoxy-β-D-ribofuranosyl)pyrrolo[2,3-d]pyrimidine hydrochloride m.p. 110°–112° C.

28) 4-N-[2-(N,N-dimethylamino)ethylphenyl]amino-5-phenyl-7-(5-deoxy-β-D-ribofuranosyl)pyrrolo[2,3-d]pyrimidine. m.p. 145°–146° C.

184) 4-N-(4-carbethoxymethylphenyl)amino-5-phenyl-7-(5-deoxy-2,3-isopropylidene-1-β-D-ribofuranosyl)pyrrolo[2,3-d]pyrimidine.

4-N-(4-carbethoxymethylphenyl)amino-5-phenylpyrrolo(2,3-d)pyrimidine (Example 2D) was glycosylated with 5-deoxy-2,3-isopropylidene-D-ribofuranose by a procedure similar to the one described for (9). The product was purified by chromatography to obtain a glassy material with no sharp melting point. Rf=0.55 (SiO$_2$, 2:1 hexane:ethyl acetate).

185) 4-N-(4-Carbethoxymethylphenyl)amino-5-phenyl-7-(5-deoxy-1-β-D-ribofuranosyl)pyrrolo[2,3-d]pyrimidine A solution of 4-N-(4-Carbethoxymethylphenyl)amino-5-phenyl-7-(5-deoxy-2,3-isopropylidene-1-β-D-ribofuranosyl)pyrrolo[2,3-d]pyrimidine) in methanol containing 0.1N HCl was refluxed for 45 minutes. Methanol was evaporated and pH of the reaction mixture was adjusted to 7.5 using saturated NaHCO3 solution. The precipitate was collected by filtration, washed with water and dried in air. Crystallization of the solid from aqueous methanol (1:1) gave the title compound. m.p. 135°–136° C. Rf=0.6 (SiO$_2$, 9:1 CH$_2$Cl$_2$-Methanol).

186) 4-N-(4-Carboxymethylphenyl)amino-5-phenyl-7-(5-deoxy-1-β-D-ribofuranosyl)pyrrolo[2,3-d]pyrimidine.

The above compound [4-N-(4-Carbethoxymethylphenyl)amino-5-phenyl-7-(5-deoxy-1-β-D-ribofuranosyl)pyrrolo[2,3-d]pyrimidine] was gently refluxed with aqueous KOH solution for three hours. The reaction mixture was cooled and neutralized with conc. HCl. The solid was collected by filtration, washed with water and dried to obtain an off white product. m.p. 205°–207° C. Rf=0.2 (SiO2, 6:1 CH2Cl2:Methanol).

187) 4-N-(4-Carbethoxyphenyl)amino-5-phenyl-7-(5-deoxy-1-β-D-ribofuranosyl)pyrrolo[2,3-d]pyrimidine.

This compound was synthesized in two steps as follows. Step 1 Preparation of 4-N-(4-Carbethoxyphenyl)amino-5-iodo-7-(5-deoxy-2,3-isopropylidene-1-β-D-ribofuranosyl)pyrrolo[2,3-d]pyrimidine (188).

To a solution of 4-chloro-5-iodo-7-(5-deoxy-2,3-isopropylidene-1-β-D-ribofuranosyl)pyrrolo[2,3-d]pyrimidine (435 mg), ethyl 4-aminobenzoate(1.65) in dry DMF (10 mL) potassium t-butoxide in t-butanol (4 mL of 1 M solution) was added and stirred at ambient temperature for one hour. Completion of the reaction was confirmed by tlc (SiO$_2$, 2:1 hexane:ethyl acetate). Volatiles were evaporated and the residue was extracted with ethyl acetate (3×30 mL). Organic layers were combined, dried over anhydrous MgSO$_4$, and evaporated. The residue was purified by chromatography to obtain the title compound as an off white solid. Yield 350 mg. m.p. 158°–162° C. Rf=0.5 (SiO$_2$, 2:1 hexane:ethyl acetate).

Step 2. The above compound (188) was subjected to phenylation by a procedure similar to the one described for Example I, below, using phenyl boronic acid and palladium tetrakis triphenylphosphine as the catalyst. The resulting intermediate was then deblocked under acidic condition as described for other examples. m.p. 163°–164° C. Rf=0.5 (SiO$_2$, 9:1 CH$_2$Cl$_2$—CH$_3$OH).

189) Preparation of 4-N-[4-(1-piperazinocarbonylmethylphenyl)amino-5-phenyl-7-(5-deoxy-1-β-D-ribofuranosyl)pyrrolo(2,3-d)pyrimidine To a solution of 4-N-(4-carboxymethylphenyl)amino-5-phenyl-7-(5-deoxy-1-β-D-ribofuranosyl)pyrrolo(2,3-d) pyrimidine (200 mg), 1-t-butyloxycarbonylpiperizine (61.4 mg), ethyl-(3-dimethylamino)propyl carbodiimide hydrochloride (96 mg), 1-hydroxybenzotriazole (54 mg) in acetonitrile (5 mL) diisopropylethylamine (290 mL) was added and stirred at room temperature for 16 hours. Volatiles were evaporated under reduced pressure, residue dissolved in ethyl acetate (20 mL) and washed with 0.5N aqueous HCl solution. The organic layer was dried over anhydrous MgSO$_4$ and evaporated under reduced pressure. The residue was chromatographed over silica gel using 4:1 hexane-ethyl acetate as the eluting solvent. Fractions containing the product were pooled and evaporated to obtain an off white glassy residue that was further subjected to deblocking condition using methanolic HCl as mentioned in earlier cases. The final product was purified by chromatography to obtain the title compound as an off white solid. Yield 120 mg. m.p. 135°–135° C. Rf=0.25. (SiO$_2$, 6:1 CH$_2$Cl$_2$:methanol).

265) 4-N[4-(2-Sulfonyloxyethyl)phenylamino]-5-phenyl-7-(5-deoxy-1-β-D-ribofuranosyl)pyrrolo[2,3-d]pyrimidine A mixture of 4-N-[4-(2-iodoethyl)phenylamino]-5-phenyl-7-(5-deoxy-2,3-O-isopropylidene-1-β-D-ribofuranosyl)pyrrolo[2,3-d]pyrimidine (1.055 g) and Na$_2$SO$_3$ (669 mg) in 150 mL of 1:1 ethanol:water was heated to reflux for 84 h. The solvents were removed under reduced pressure and the excess water was azeotroped with ethanol. The volatiles were evaporated, and the residue was triturated with methanol:dichloromethane (1:1) and filtered. The filtrate was evaporated to give an off-white solid. Trituration with ether gave a white solid. A solution of 150 mg of this product was heated to reflux in 15 mL of 1N HCl for 2 hours. The solvent was evaporated, and the product was crystallized from methanol/ether and purified by preparative HPLC (YMC RP-18 column, 25×250 mm, 1=283 nm, 50:50 to 100:0 (methanol: (95:5:1, water:methanol:acetic acid)) over 15 min at 6 mL/min followed by 100% methanol over 10 min at 6 mL/min; Rt=20.0 min) to obtain a white solid, m.p. 209°–212° C.

H. Preparation of 4-N-(4-N-acetylaminophenyl)amino-5-iodo-7-(1-β-D-5-deoxy-2,3-O-isopropylideneribose)pyrrolo[2,3-d]pyrimidine (29)

A mixture of 848 mg (1.87 mmol) of 4-chloro-5-iodo-7-(5-deoxy-2,3-O-isopropylidene-1-β-D-ribofuranosyl) pyrrolo[2,3-d]pyrimidine and 580 mg (3.86 mmol) of 4-aminoacetanilide in 50 mL of ethanol was heated to reflux for 15 h. The solvent was evaporated under reduced pressure and the residue dissolved in ethyl acetate and washed with water and saturated aqueous sodium chloride solution. Dried over magnesium sulfate and evaporated under reduced pressure. Chromatography on silica gel using 4% methanol in dichloromethane afforded 610 mg (57%) of the title compound.

HNMR (200 MHZ, DMSO-d$_6$): 9.93 (s,1H), 8.33 (s,1H) 8.17 (s, 1H), 7.81 (s, 1H), 7.60 (AB quartet, 4H), 6.17 (d, J=3.1 Hz, 1H), 2.03 (s, 3H), 1.51 (s, 3H), 1.30 (s, 3H), 1.26 (d, J=6.5 Hz, 3H).

The following compound was prepared using the above mentioned procedure:

190) 4-N-(4-fluorophenyl)amino-5-iodo-7-(5-deoxy-2,3-O-isopropylidene-1-β-D-ribofuranosyl)pyrrolo[2,3-d] pyrimidine, m.p. 160°–162° C.

I. Preparation of 4-N-(4-N-acetylaminophenyl)amino-5-phenyl-7-(1-β-D-5-deoxy-2,3-O-isopropylideneribose) pyrrolo[2,3-d]pyrimidine (30)

A solution of 560 mg (0.99 mmol) of 4-N-(4-N-acetylaminophenyl)amino-5-iodo-7-(1-β-D-5-deoxy-2,3-O-isopropylideneribose)pyrrolo[2,3-d]pyrimidine, 626 mg (5.13 mmol) of phenylboric acid and 240 mg (0.21 mmol) of palladium tetrakistriphenylphosphine in 9 mL of diglyme was treated with 6 mL of saturated aqueous sodium carbonate solution and heated at 100° C. for 5 h. The mixture was cooled to room temperature, filtered through a celite pad and partitioned between ethyl acetate and water. The organic layer was washed with water and saturated sodium chloride solution, dried over magnesium sulfate and evaporated under reduced pressure at 50° C. Chromatography on silica gel eluting with 3% methanol in dichloromethane afforded 507 mg of the title product.

HNMR (200 MHZ, DMSO-d$_6$): 9.87 (s, 1H), 8.38 (s, 1H), 6.28 (d, J=3.0 Hz), 2.00 (s, 3H), 1.54 (s, 3H), 1.31 (s, 3H), 1.29 (d, J=7.2 Hz).

The following compound was made by the above two step procedure, by substituting 3-hydroxymethylaniline for 4-aminoacetanilide in the first step.

31) 4-N-(3-hydroxymethylphenyl)amino-5-phenyl-7-(5-deoxy-1-β-D-ribofuranosyl)-pyrrolo(2,3-d)pyrimidine. m.p. 192°–193° C.

The following compounds were prepared by reacting 4-N-(4-fluorophenyl)amino-5-iodo-7-(5-deoxy-2,3-O-isopropylidene-1-β-D-ribofuranosyl)pyrrolo[2,3-d] pyrimidine (190) with appropriately substituted phenylboronic acids by the preceding procedure.

191) 4-N-(4-fluorophenyl)amino-5-(4-carboxyphenyl)-7-(5-deoxy-2,3-O-isopropylidene-1-β-D-ribofuranosyl) pyrrolo[2,3-d]pyrimidine. Rf=0.5 (silica, dichloromethane/methanol 90/10).

192) 4-N-(4-fluorophenyl)amino-5-(4-hydroxymethylphenyl)-7-(5-deoxy-2,3-O-isopropylidene-1-β-D-rilbofuranosyl)pyrrolo[2,3-d] pyrimidine, Rf=0.2 (silica, hexanes/ethyl acetate 70/30). 4-hydroxymethylbenzeneboronic acid used for the synthesis of this compound was made by a literature procedure described by B. I. Alo, et al., J. Org. Chem., 56, 3763 (1991) for similar boronic acids.

193) 4-N-(4-fluorophenyl)amino-5-(3-aminophenyl)-7-(5-deoxy-2,3-O-isopropylidene-1-β-D-ribofuranosyl) pyrrolo[2,3-d]pyrimidine, Rf=0.2 (silica, hexanes/ethyl acetate 70/30).

194) 4-N-(4-fluorophenyl)amino-5-(4-formylphenyl)-7-(5-deoxy-2,3-O-isopropylidene-1-β-D-ribofuranosyl) pyrrolo[2,3-d]pyrimidine, Rf=0.5 (silica, hexanes/ethyl acetate 70/30).

J. Preparation of 4-N-(4-aminophenyl)amino-5-phenyl-7-(5-deoxy-2,3-O-isopropylidene-1-β-D-ribofuranosyl) pyrrolo[2,3-d]pyrimidine (32)

A solution of 440 mg (0.85 mmol) of 4-(4-acetylaminophenyl)amino-5-phenyl-7-(-5-deoxy-2,3-O-isopropylidenene-1-β-D-ribofuranosyl)pyrrolo[2,3-d] pyrimidine and 912 mg of KOH in 50 mL of ethanol was heated to reflux for a period of 140 h. The mixture was cooled to room temperature and partitioned between water and methylene chloride. The organic layer was washed with water and saturated sodium chloride solution, dried over MgSO$_4$ and evaporated under reduced pressure. Obtained 301 mg (72% crude yield) of a white foam which was used without further purification in the following step.

HNMR (200 MHZ, DMSO-d$_6$): 8.28 (s, 1H), 7.13 (d, J=8.7 Hz, 2H) 6.50 (d, J=8.7 Hz, 2H) 6.25 (d, J=3.0 Hz,1H), 1.53 (s, 3H) 1.31 (s, 3H), 1.29 (d, J=7.5 Hz, 3H).

K. Preparation of 4-N-|4-(N-trifluoromethanesulfonylamino)phenyl|amino-5-phenyl-7-(5-deoxy-1-β-D-ribofuranosyl)pyrrolo|2,3-d|pyrimidine (33).

To a mixture of 190 mg (0.39 mmol) of 4-N-(4-aminophenyl)amino-5-phenyl-7-(5-deoxy-2,3-O-isopropylidene-1-β-D-ribofuranosyl)pyrrolo|2,3-d| pyrimidine in 20 mL of dichloromethane cooled to –78° C. was added N,N-diisopropylethylamine (140 μL, 0.80 mmol) followed by trifluoromethanesulfonic anhydride (80 μL, 0.48 mmol). The resulting reaction mixture was allowed to stir for a period of 3.5 h, when the temperature of the external bath had reached 0° C. Water was added and the organic layer was separated and washed (water and saturated sodium chloride solution), dried ($MgSO_4$) and evaporated under reduced pressure. Chromatography on silica gel using 5% methanol in methylene chloride afforded an oil which was treated with 7:3 (v:v) trifluoroacetic acid:water at room temperature for 2.5 h. The volatiles were evaporated under reduced pressure and the residue coevaporated twice with toluene. The resulting oil was treated with water and methanol. The precipitate obtained was removed by filtration, suspended in hexanes and filtered one more time. After drying for 12 h at 45° C. under high vacuum the resulting off-white solid had a melting point of 153°–155° C.

L. Preparation of 4-N-(4-cyanophenyl)amino-5-iodo-7(5-deoxy-2,3-O-isopropylidene-1-β-D-ribofuranosyl)pyrrolo |2,3-d|pyrimidine (34)

A solution of 400 mg (0.92 mmol) of 4-chloro-5-iodo-7-(1-β-D-2,3-O-isopropylidene 5-deoxyribofuranosyl) pyrrolo[2,3-d]pyrimidine and 4-aminobenzonitrile (1.085 g, 9.18 mmol) in DMF (10 mL) at room temperature under a nitrogen atmosphere was treated with 5.0 mL (5.0 mmol) of a 1M solution of potassium t-butoxide in t-butanol. The resulting dark mixture was stirred at the same temperature for 1 h. The volatiles were removed under reduced pressure and the residue taken to pH 7 using 1N aqueous HCl solution and extracted with ethyl acetate. The organic phase was washed (water, sat NaCl solution), dried ($MgSO_4$) and evaporated under reduced pressure. Chromatography on silica gel using 25% ethyl acetate in hexanes afforded 408 mg of the title compound.

HNMR (200 MHZ, DMSO-$d_6$); 8.76(s, 1H), 8.48 (s, 1H), 7.87 (AB quartet, 4H), 6.20 (d, J=2.6 Hz, 1H), 1.52 (s, 3H), 1.30 (s, 3H), 1.26 (d, J=6.6 Hz, 3H).

M. Preparation of 4-N-(4-cyanophenyl)amino-5-phenyl-7-(5-deoxy-2,3-O-isopropylidene-1-β-D-ribofuranosyl) pyrrolo[2,3-d|pyrimidine (35)

A mixture of 4-N-(4-cyanophenyl)amino-5-iodo-7-(5-deoxy-2,3-O-isopropylidene-1-β-D-ribofuranosyl)pyrrolo [2,3-d]pyrimidine (408 mg, 0.79 mmol), phenyl boric acid (433 mg, 3.55 mmol), palladium tetrakistriphenylphosphine (110 mg, 0.09 mmol) and 5 mL of a saturated solution of sodium carbonate in 25 mL of diglyme was heated to 90° C. for 2 h. After cooling to room temperature and filtering through a celite pad, the solvent was evaporated and the residue chromatographed on silica using 20% ethyl acetate in hexanes as the eluent. Obtained 334 mg of the title compound with Rf=0.30 (20% ethyl acetate in hexanes, silica).

N. Preparation of 4-N-(4-amidoximephenylamino-5-phenyl-7-(5-deoxy-2,3-O-isopropylidene-1-β-D-ribofuranosyl)pyrrolo[2,3-d]pyrimidine (36)

A solution of 4-N-(4-cyanophenyl)amino-5-phenyl-7-(5-deoxy-2,3-O-isopropylidene-5-deoxyribofuranosyl) pyrrolo [2,3-d]pyrimidine (162 mg, 0.35 mmol) in THF (15 mL) was treated with a solution of 250 mg (0.35 mmol) of hydroxylamine hydrochloride and 14 mg (0.35 mmol) of sodium hydroxide in 5 mL of water. The mixture was heated to reflux for 96 h. The THF was removed under reduced pressure and the residue partitioned between ethyl acetate and water. The organic layer was washed (water, saturated sodium chloride solution), dried (MgSO4) and evaporated. Chromatography on silica gel using 5% methanol in dichloromethane afforded 141 mg of product.

O. Preparation of 4-N-(4-amidoximephenyl)amino-5-phenyl-7-(1-β-D-5-deoxyribofuranosyl)pyrrolo|2,3-d| pyrimidine hydrochloride (37)

A solution of 4-N-(4-amidoximephenyl)amino-5-phenyl-7-(5-deoxy-2,3-O-isopropylidene-1-β-D-ribofuranosyl) pyrrolo|2,3-d|pyrimidine (141 mg) in 10 mL of methanol saturated with hydrogen chloride was stirred at room temperature for a period of 1 h. Removal of the volatiles left a foam which was crystallized from methanol-ether. The resulting off white solid had m.p. 173°–178° C.

P. Preparation of 4-N-(4-amidinophenyl)amino-5-phenyl-7-(5-deoxy-1-β-D-ribofuranosyl)pyrrolo|2,3-d|pyrimidine (39)

This compound was synthesized by procedures described in the literature (Alig et al, J.Med.Chem 35, 4393 (1992); Stanek et al J. Med. Chem. 36,2168 (1993); Stanek et al J. Med. Chem. 36, 46 (1993)) as follows: A solution of 150 mg of 4-N-(4-Cyanophenyl)amino-5-phenyl-7-(5-deoxy1-β-D-ribofuranosyl) pyrrolo[2,3-d]pyrimidine in pyridine (10 mL) and triethylamine (1.1 mL) was saturated with hydrogen sulfide and stirred at room temperature for 24 hours, when tic indicated near completion of the reaction. The solvents were evaporated under high vacuum. The residue was dissolved in acetone (10 mL) and treated with iodomethane (0.05 mL). The mixture was stirred overnight and additional amount of iodomethane was added in order to drive the reaction to completion as indicated by disappearance of the starting material by thin layer chromatography. The solvents were evaporated, the residue was taken in methanol (10 mL), treated with ammonium acetate (27 mg) and refluxed for 16 h. The product obtained after evaporation was purified by preparative HPLC [YMC RP-18, 25×250mm, 5 μ; λ=280 nm; 50/50–90/10 $CH_3OH$/(95:5:0.5 $H_2O$: $CH_3OH$:acetic over 30 min at 6.0 mL/min; Rt=9.6 min.]dissolved in dilute aqueous HCl and lyophilized to obtain the title compound as a solid with m.p. 183°–185° C.

R1. Preparation of 4-N-[4-(N-acetylaminosulfonyl)phenyl] amino-5-phenyl-7-(5-deoxy1-β-D-ribofuranosyl)pyrrolo[2, 3-d]pyrimidine (40).

To a solution of 4-N-(4-sulfonamidophenyl)amino-5-phenyl-7-(5-deoxy-2,3-O-isopropylidene1-β-D-ribofuranosyl)pyrrolo[2,3-d]pyrimidine (293 mg, prepared by the methods illustrated in examples 5H-5I) in 15 mL of tetrahydrofuran at room temperature was added 0.61 mL of a 1.0M solution of potassium t-butoxyde in t-butanol. After stirring for 1.5 h at the same temperature, acetic anhydride (0.10 mL) was added and the solution stirred for an additional 10 min. The reaction was treated with 10 mL of 70% trifluoroacetic acid in water and stirred at room temperature for 1 h. Evaporation of the volatiles and chromatography on silica gel (eluting with 5% methanol in dichloromethane) yielded 85 mg of title compound, m.p. 229°–231° C.

R2. Preparation of 4-N-|4-(4-piperazinocarbonylmethyloxy)phenyl|amino-5-phenyl-7-(5-deoxy-1-β-D-ribofuranosyl)pyrrolo(2,3-d)pyrimidine (196)

The title compound was synthesized in two steps as follows.

Step 1: Preparation of 4-N-|4-(4-piperazinocarbonylmethyloxy)phenyl]amino-5-iodo-7-(5- deoxy-2,3-isopropylidene-1-β-D-ribofuranosyl)pyrrolo[2,3-d]pyrimidine (195).

A mixture of 4-chloro-5-iodo-7-(5-deoxy-2,3-isopropylidene-1-β-D-ribofuranosyl)pyrrolo(2,3-d) pyrimidine (435 mg), 4-(1-t-butyloxy-carbonyl4-piperizinocarbonylmethyleneoxy)aniline (1.3 g), sodium acetate (820 mg) in ethanol was refluxed for 16 hours. The completion of the reaction was confirmed by tic ($SiO_2$, 19:1 $CH_2Cl_2$—$CH_3OH$, Rf=0.65). Volatiles were evaporated and the residue was extracted with ethyl acetate (3×30 mL). Organic layers were combined, dried over anhydrous MgSO4, and evaporated. The residue was purified by chromatography to obtain the title compound. Yield 1.22 g. Rf=0.65. ($SiO_2$, 19:1 $CH_2Cl_2$—$CH_3OH$).

Step 2: Preparation of 4-N-[4-(4-piperazinocarbonylmethyloxy)phenyl]-amino-5-phenyl-7-(5-deoxy-1-β-D-ribofuranosyl)pyrrolo[2,3-d]pyrimidine (196).

The product from step 1 was subjected to phenylation by a procedure similar to the one described for 4-N-(4-N-acetylaminophenyl)amino-5-phenyl-7-(5-deoxy-2,3-O-isopropylidene-1-β-D-ribofuranosyl)pyrrolo[2,3-d] pyrimidine using phenyl boronic acid and palladium tetrakis triphenylphosphine as the catalyst. The resulting intermediate was deblocked under acidic condition as described earlier. The final product was purified by chromatography and crystallization. m.p. 148°–150° C., decomp. Rf=0.2 ($SiO_2$, 9:1 $CH_2Cl_2$—$CH_3OH$).

R3. Preparation of 4-N-[4-(2-Ureidoethyl)phenyl]amino-5-phenyl-7-(5-deoxy-1-β-D-ribofuranosyl) pyrrolo[2,3-d] pyrimidine A mixture of 923 mg of 4-N-[4-(2-Aminoethyl )phenyl] amino-5-phenyl-7-(5-deoxy-2,3-O-isopropylidene-1-β-D-ribofuranosyl) pyrrolo[2,3-d]pyrimidine, 1.7476 g of $K_2CO_3(H_2O)_{1.5}$ and 324 mg of aminoiminomethanesulfonic acid in 200 mL of ethanol:water (1:1) was heated to reflux for 90 h and evaporated under reduced pressure. Added an excess of 1M aqueous HCl and and evaporated the solvent, coevaporating with toluene. Dissolved in methanol (75mL) and 5M aqueous HCl (5 mL) and heated to reflux for a period of 1.5 h. Evaporated the volatiles and coevaporated with toluene. The residue was heated in ethanol and the white solid filtered off. The ethanol was evaporated under reduced pressure to afford a yellow foam. Reprecipitation from ethanol-ether gave a pale yellow foam, Rf=0.25 (96:4:1 methanol:acetic acid:water on reverse phase silica gel)

R4. Preparation of 4-N-[4-(2-(1-piperazino)ethyl )phenyl] amino-5-phenyl-7-(1-α-L-lyxofuranosyl)pyrrolo[2,3-d] pyrimidine (12)

A solution of 470 mg of 2,3-O-isopropylidene-5-O-(t-butyldimethyl)silyllyxose and 0.2 mL of $CCl_4$ in 10 mL of toluene was cooled to –25° C. and treated with a solution of 0.34 mL of HMPT in toluene, at a rate such that the internal temperature did not exceed –20° C. After the addition was completed, the reaction mixture was stirred for additional 30 min at –25° to –5° C. Quenched the reaction by the addition of cold water and separated the organic phase, which was dried over $MgSO_4$. This toluene solution was added to a stirring mixture of 500 mg of 4-N-(4-(2-(1-piperazino-4-t-butoxycarbonyl)ethyl)phenyl)amino-5-phenyl-pyrrolo* 2,3-d]pyrimidine, 104 mg of powdered KOH and 0.11 mL of TDA-1. After stirring for 16 h, the reaction mixture was partitioned between ethyl acetate and water. The organic phase was washed with water and saturated sodium chloride solution, dried over $MgSO_4$ and evaporated. Chromatography on silica gel, eluting with 3.5% methanol in methylene chloride afforded 540 mg of an oil. This material was dissolved in methanol (15 mL), treated with 1M aqueous HCl and heated to reflux with frequent addition of further hydrochloric acid in order to drive the reaction to completion as indicated by thin layer chromatography. When the reaction appeared to be complete, evaporated the methanol and purified by preparative HPLC (C18, 50×250 mm, (water/methanol/acetic acid; 95/5/0.5):methanol 50:50 to 10:90 over 30 min), Flow rate:6 mL/minute, λ=280 nm) . The product so obtained was crystallized from a mixture of methanol, ethanol and ether to afford the title compound as a white solid, m.p. 162°–165° C.

S. Preparation of 4-N-(2-pyridylmethylamino)-5-iodo-7-(5-deoxy-1-β-D-ribofuranosyl)pyrrolo[2,3-d]pyrimidine (41)

A mixture of 2.2 mmol of 4-chloro-5-iodo-7-(5-deoxy-2, 3-O-isopropylidene-1-β-D-ribofuranosyl) and 4.0 equivalents of 2-aminomethyl pyridine in 25 mL of ethanol were heated to reflux for a period of 24 hours. The solvent was removed under reduced pressure and the residue partitioned between ethyl acetate and water. The organic layer was washed with water and then with a saturated solution of sodium chloride. Dried over sodium sulfate and evaporated under reduced pressure to obtain 515 mg (83%) of a waxy yellow solid whose HNMR had a diagnostic doublet at 6.14 ppm (J=2.9 Hz). This product was treated with 20 mL of a 7:3 mixture of trifluoroacetic acid and water at room temperature for 90 min. The reaction mixture was evaporated under reduced pressure, dissolved in methanol and stirred for 15 minutes in the presence of an excess of potassium carbonate. The potassium carbonate was filtered, the solvent removed and the residue chromatographed on silica using 5% methanol in methylene chloride to afford a white solid with Rf=0.28 (5% $CH_3OH$ in $CH_2Cl_2$; silica). Crystallized from methanol-ether to obtain 445 mg (43%) of the title compound with melting point 199°–202° C.

T. Preparation of 4-N-(4-fluorophenyl)amino Pyrrolo Pyrimidines

197) Preparation of 4-N-(4-fluorophenyl)amino-5-[4-(N-piperazinomethyl)phenyl]-7-(5-deoxy-β-D-ribofuranosyl)pyrrolo[2,3-d]pyrimidine:

A mixture of 4-N-(4-fluorophenyl)amino-5-(4-hydroxymethylphenyl)-7-(5-deoxy-2,3-O-isopropylidene-1-β-D-ribofuranosyl)pyrrolo[2,3-d]pyrimidine (192) (100 mg) and methyl triphenoxyphosphonium iodide (299 mg) in dichloromethane (4 mL) was stirred overnight at room temperature. The reaction mixture was quenched with methanol (1 mL) and added to a solution of piperazine (900 mg) in dichloromethane (5 mL). After stirring at room temperature for 24 hours, the reaction mixture was poured into a 0.5M solution of sodium thiosulfate and extracted with ethyl acetate. The combined organic extracts were washed with water followed by saturated aqueous sodium chloride solution, dried over sodium sulfate and concentrated under reduced pressure. The residue was purified by chromatography (silica, dichloromethane|methanol). The product was dissolved in 70% aqueous trifluoroacetic acid and stirred at room temperature for 2 hours. The volatiles were evaporated and the residue was coevaporated with water (2×20 mL), ethanol (2×20 mL) and partitioned between ethyl acetate and saturated aqueous sodium bicarbonate. The organic layer was separated and the aqueous layer was extracted twice with ethyl acetate. The combined organic extracts were washed with saturated aqueous sodium chloride and dried over sodium sulfate. Evaporation of the solvent under reduced pressure gave a white powder that was purified by HPLC (C18, 50×250 mm, methanol/water/trifluoroacetic acid 50/50/0.1), 15 mL/minute, λmax=

198) Preparation of 4-N-(4-fluorophenyl)amino-5-[4-(dimethylaminomethyl)phenyl]-7-(5-deoxy-β-D-ribofuranosyl)pyrrolo[2,3-d]pyrimidine.

This compound was prepared by a procedure similar to the one described above except that piperazine was replaced with dimethylamine. The compound was purified by crystallization. m.p. 167°–168° C.

199) Preparation of 4-N-(4-fluorophenyl)amino-5-[4-(N-piperazinocarbonyl)phenyl]-7-(5-deoxy-1-β-D-ribofuranosyl)pyrrolo(2,3-d]pyrimidine hydrochloride salt Triethylamine (0.33 mL) and benzotriazol-1-yloxytripyrrolidinophosphonium hexafluorophosphate (662 mg) were added to a solution of 4-N-(4-fluorophenyl)amino-5-(4-carboxyphenyl)-7-(5-deoxy-2,3-O-isopropylidene-1-β-D-ribofuranosyl)pyrrolo[2,3-d]pyrimidine (191) (300 mg) in dimethylformamide at room temperature. After stirring for one hour, tert-butyl 1-piperazinecarboxylate (240 mg) was added and stirring was carried on for 20 minutes The reaction was diluted with ethyl acetate and washed with saturated aqueous sodium chloride. The organic layer was dried over sodium sulfate and concentrated under reduced pressure. The residue was purified by chromatography (silica, hexanes/ethyl acetate 50/50 to 30/70). Yield 329 mg, 81%, Rf=0.3 (silica, hexanes/ethyl acetate 50/50). The product was dissolved in 70% aqueous trifluoroacetic acid and stirred at room temperature for 1 hour. The volatiles were evaporated and the residue was coevaporated with water (2×20 mL) and ethanol (2×20 mL). The oily residue was stirred with saturated aqueous sodium bicarbonate. The white precipitate that formed was collected by filtration, rinsed with water and purified twice by chromatography (silica, dichloromethane/methanol/28% aqueous ammonium hydroxide 90/10/0 to 50/50/1) followed by a purificatio on a reverse phase chromatography (C18 Bakerbond™, water/methanol/acetic acid 90/10/1 to 50/50/1). The resulting pure product was dissolved in 1N aqueous HCl solution and lyophilized several times to afford the pure product as the hydrochloride salt. Yield 149 mg, 40%, Rf=0.4 (C18, water/methanol/acetic acid 50/50/1). m.p. 190° C.

200) Preparation of 4-N-(4-fluorophenyl)amino-5-[4-(2-N, N-diethylaminoethyleneaminocarbonyl)phenyl]-7-(5-deoxy-1-β-D-ribofuranosyl)pyrrolo[2,3-d]pyrimidine hydrochloride This compound was prepared by a procedure similar to the one described above except that tert-butyl 1-piperazinecarboxylate was replaced with N,N-diethylaminoethyleneamine and purified as follows. After deprotection of the nucleoside and coevaporation with water and ethanol, the oily residue was treated with saturated aqueous sodium bicarbonate. Ethanol was added to the resulting gel and filtered. The filtrate was concentrated under reduced pressure and the residue was chromatographed (silica, dichloromethane/methanol 90/10 to 70/30). Unreacted N,N-diethylethylenediamine was removed by dissolving the contaminated nucleoside in dimethylformamide and treating it with acetic anhydride (1 mL), pyridine (1 mL) and 4-dimethylaminopyridine (catalytic amount). After stirring overnight at room temperature the reaction mixture was diluted with ethyl acetate and washed with saturated aqueous sodium bicarbonate followed by saturated aqueous sodium chloride solution. The organic layer was dried over sodium sulfate and evaporated under reduced pressure. The residue was dissolved in 0.5M sodium methoxide in methanol (3.4 mL). After stirring at 0° C. for one hour the reaction mixture was quenched with acetic acid, diluted with ethyl acetate and washed with saturated aqueous sodium bicarbonate followed by saturated aqueous sodium chloride. The organic layer was dried over sodium sulfate and evaporated under reduced pressure. The residue was purified twice by chromatography (silica, dichloromethane/methanol 90/10 to 70/30) followed by another purification by a reverse phase chromatography (C18 Bakerbond™, water/methanol/acetic acid 90/10/1 to 50/50/1). The resulting product was dissolved in 1N aqueous HCl solution and lyophilized several times to afford the title compound as hydrochloride salt. Yield 215 mg, 38%, Rf=0.4 (C18, water/methanol/acetic acid 50/50/1), m.p. 140° C.

201) Preparation of 4-N-(4-fluorophenyl)amino-5-[4-(2-ethyloxycarbonyl-E-ethenyl)phenyl]-7-(5-deoxy-2,3-O-isopropylidene-1-β-D-ribofuranosyl)pyrrolo[2,3-d]pyrimidine Triethylphosphonoacetate (0.45 mL) was added to a suspension of sodium hydride (60% in oil, 230 mg) in ether (5 mL) at 0° C. After stirring at 0° C. for one hour, a solution of 4-N-(4-fluorophenyl)amino-5-(4-formylphenyl)-7-(5-deoxy-2,3-O-isopropylidene-1-β-D-ribofuranosyl)pyrrolo [2,3-d]pyrimidine (194) (523 mg) in ether (5 mL) was added. The reaction mixture was stirred one hour at room temperature, quenched with a saturated solution of ammonium chloride and diluted with ethyl acetate. The organic layer was washed with saturated aqueous ammonium chloride followed by saturated aqueous sodium chloride solution and dried over sodium sulfate. The solvent was evaporated under reduced pressure and the residue was purified by chromatography (hexanes/ethyl acetate 85/15 to 75/25) to provide the title compound, Rf=0.55 (silica, hexanes/ethyl acetate 70/30); Yield: 543 mg, 90 %.

202) Preparation of 4-N-(4-fluorophenyl)amino-5-[4-(2-carboxy-E-ethenyl)phenyl]-7-(5-deoxy-1-β-D-ribofuranosyl)pyrrolo[2,3-d]pyrimidine A solution of 4-N-(4-fluorophenyl)amino-5-[4-(2-ethyloxycarbonyl-E-ethenyl)phenyl]-7-(5-deoxy-2,3-O-isopropylidene-1-β-D-ribofuranosyl)pyrrolo[2,3-d] pyrimidine (201) (500 mg) in tetrahydrofuran (10 mL) and 1N aqueous sodium hydroxide (5 mL) was refluxed for three hours. The reaction mixture was cooled to 0° C. and acidified to pH 1 with 1N hydrochloric acid. The aqueous layer was extracted three times with ethyl acetate. The combined organic extracts were dried over sodium sulfate and concentrated under reduced pressure. The resulting product was dissolved in 70% aqueous trifluoroacetic acid and stirred at room temperature for 2 hours. The volatiles were evaporated and the residue was coevaporated with water (2×20 mL), ethanol (2×20 mL) and purified by chromatography (silica, dichloromethane/methanol/acetic acid 95/5 to 80/20/1). Recrystallization from water/methanol afforded the pure product (370 mg, 77%) Rf=0.4 (silica, dichloromethane/methanol 90/10). m.p. 208°–210° C.

203) Preparation of 4-N-(4-fluorophenyl)amino-5-[4-(2-methoxycarbonyl-ethyl)phenyl]-7-(5-deoxy-2,3-O-isopropylidene-1-β-D-ribofuranosyl)pyrrolo[2,3-d] pyrimidine Magnesium (225 mg) was added to a solution of 4-N-(4-fluorophenyl)amino-5-[4-(2-ethyloxycarbonyl-E-ethenyl) phenyl]-7-(5-deoxy-2,3-O-isopropylidene-β-D-ribofuranosyl)pyrrolo[2,3-d]pyrimidine (201) (486 mg) in methanol (20 mL) and tetrahydrofuran (20 mL). After stirring at room temperature for 24 hours the reaction mixture was poured into a mixture of 1N hydrochloric acid, ice and ethyl acetate. The layers were separated and the aqueous layer was extracted three times with dichloromethane. The combined organic extracts were dried over sodium sulfate and concentrated under reduced pressure. The residue was purified by chromatography (silica, hexanes/ethyl acetate 75/25 to 65/35); yield 330 mg, 69%; Rf=0.6 (silica, hexanes/ethyl acetate 70/30).

204) Preparation of 4-N-(4-fluorophenyl)amino-5-[4-(2-carboxyethyl)phenyl]-7-(5-deoxy-1-β-D-ribofuranosyl)pyrrolo[2,3-d]pyrimidine.

The title compound was prepared by a procedure similar to the one disclosed for 4-N-(4-fluorophenyl)amino-5-[4-(2-carboxy-E-ethenyl)phenyl]-7-(5-deoxy-1-β-D-ribofuranosyl)pyrrolo[2,3-d]pyrimidine Rf=0.4 (silica, dichloromethane/methanol 90/10). m.p. 168°–170° C.

205) Preparation of 4-N-(4-fluorophenyl)amino-5-(3-aminophenyl)-7-(5-deoxy-1-β-D-ribofuranosyl)pyrrolo[2,3-d]pyrimidine 4-N-(4-fluorophenyl)amino-5-(3-aminophenyl)-7-(5-deoxy-2,3-O-isopropylidene-1-β-D-ribofuranosyl)pyrrolo[2,3-d]pyrimidine (193) was dissolved in 70% aqueous trifluoroacetic acid and stirred at room temperature for 2 hours. The volatiles were evaporated and the residue was coevaporated with water (2×20 mL), ethanol (2×20 mL) and purified by chromatography (silica, dichloromethane/ethanol 97.5/2.5 to 90/10). Recrystallization from ethanol afforded the pure product Rf=0.5 (silica, dichloromethane/methanol 80/20), m.p. 114°–116° C.

206) Preparation of 4-N-(4-fluorophenyl)amino-5-(3-guanidinophenyl)-7-(5-deoxy-1-β-D-ribofuranosyl)pyrrolo[2,3-d]pyrimidine A mixture of 4-N-(4-fluorophenyl)amino-5-(3-aminophenyl)-7-(5-deoxy-1-β-D-ribofuranosyl)pyrrolo[2,3-d]pyrimidine (205) (300 mg) and 1-[N,N'-bis-(tert-butyloxycarbonyl)-carboxamidine]-1H-pyrazole (320 mg) [M. S. Bernatowicz et al. Tetrahedron Lett., 34 (21), 3389 (1993)] in tetrahydrofuran (3 mL) was heated at 60° C. overnight. The reaction mixture was cooled and concentrated under reduced pressure. The residue was purified by chromatography (silica, toluene/ethyl acetate 80/20 to 60/40); yield 240 mg, 51%; Rf=0.7 (silica, hexanes/ethyl acetate 30/70). The product was dissolved in 50/50 dichloromethane/trifluoroacetic acid (10 mL). After stirring at room temperature for 4 hours the reaction mixture was concentrated under reduced pressure and coevaporated four times with ethanol. The residue was purified by HPLC (C18, 50×250 mm, methanol/(water/methanol/acetic acid 951510.5) 45/55,15 mL/minute, λmax=260 nm, Rt=13.6 minutes). The resulting product was dissolved in 1N aqueous HCl and lyophilized several times to afford the pure product as the hydrochloride salt. Yield 82 mg, 42%, Rf=0.35 (C18, water/methanol/acetic acid 30/70/1). m.p.185° C.

U. Preparation of 4-N-[4-(2-Guanidinoethyl)phenyl]amino-5-phenyl-7-(5-deoxy-1-β-D-ribofuranosyl)pyrrolo[2,3-d] pyrimidine hydrochloride (267)

To a solution of 529 mg of 4-N-[4-(2-aminoethyl)phenyl] amino-5-phenyl-7-(5-deoxy-1-β-D-ribofuranosyl)pyrrolo [2,3-d]pyrimidine and 1.09 g of $K_2CO_3^-(H_2O)_{1.5}$ in ethanol (30 mL) and water (60 mL) was added 186 mg of aminoimi-nomethanesulfonic acid (Miller and Bischoff, *Synthesis*, 777 (1986)) and stirred at room temperature for 48 hours. Volatiles were evaporated under reduced pressure and partitioned between dichloromethane and water. The dichloromethane was separated and the aqueous suspension was evaporated to leave a white solid. This solid was heated in ethanol and filtered. The filtrate was evaporated and the resulting hygroscopic solid was dissolved in 1M aqueous hydrochloric acid. This solution was repeatedly lyophilized to afford a white solid, m.p. 153°–157° C.

V. Preparation of 4-N-[2-(Nicotinylaminoethyl)phenyl] amino-5-phenyl-7-(5-deoxy-1-β-D-ribofuranosyl)pyrrolo (2,3-d)pyrimidine (268)

To a solution of 4-N-[2-(aminoethyl)phenyl]amino-5-phenyl-7-(5-deoxy-2,3-isopropylidene-1-β-D-ribofuranosyl)pyrrolo(2,3-d)pyrimidine (1.19 g) (obtained by a procedure described for Ex#22, prior to its removal of the isopropylidene groups), EDCI (0.432 g), 1-hydroxybenzotriazole (0.243 g), acetonitrile (10 mL), diisopropylethylamine (1.3 mL), and nicotinic acid (0.221 g) was stirred at room temperature overnight. Volatiles were evaporated and the residue was chromatographed over $SiO_2$ using dichloromethane-MeOH (19:1) as the eluting solvent. The fractions containing the pure product were pooled and evaporated to obtain a glassy material that was dissolved in methanol (57 mL) containing 1N HCl (4 mL) and refluxed for 1 hr. Methanol was evaporated and the residue was treated with aqueous $NaHCO_3$ solution. The solid that separated was collected by filtration, washed with water and crystallized from aqueous methanol to obtain 380 mg of the title compound, m.p. 218°–220° C. Rf=0.37 ($SiO_2$ 6:1, $Ch_2Cl_2$—MeOH).

W. Preparation of 4-N-(4-Guanidinophenyl)amino-5-phenyl-7-(5-deoxy-1-β-D-ribofuranosyl)pyrrolo[2,3-d] pyrimidine (269)

A mixture of 4-N-(4-aminophenyl)amino-5-phenyl-7-(5-deoxy-2,3-O-isopropylidene-1-β-D-ribofuranosyl)pyrrolo [2,3-d]pyrimidine (235 mg) diisopropyl ethyl amine (0.93 mL) and 1-H-pyrazole-1-carboxamidine monohydrochloride (391 mg ) in THF (19 mL) was heated to reflux for a period of 44 hours. The volatiles were evaporated under reduced pressure. The residue was chromatographed over a silica gel column using 9:1 $CH_2Cl_2$:$CH_3OH$ followed by 1:1 $CH_2Cl_2$:$CH_3OH$ as eluting solve systems. The latter fractions were purified by preparative HPLC [YMC RP-18, 25×250 mm, 5 µ; λ=280 nm; 60/40 $CH_3OH$:1% acetic acid over 30 min at 15 mL/min; Rt=~17 min] to obtained a white foam. HNMR(200 MHz, DMSO-$d_6$): 8.41 (1H, s); 7.71 (1H, s), 7.35–7.64 (m); 7.08 (2H d, J=6 Hz), 6.28 (1H, d, J=3.8 Hz), 5.35(1H, m) 4.75 (1H, m); 4.18 (1H, m), 1.53 (3H, s), 1.29 (3H, s); 1.28 (3H, d, J=5.6 Hz). This material was dissolved in methanol (25 mL) and treated with 1M aqueous HCl solution (1.5 mL). The solution was heated to reflux for 1 hour. The methanol was removed under reduced pressure and the residual aqueous solution neutralized with dilute $NaHCO_3$ solution. The white precipitate thus formed was collected by filtration and dried under vacuum at 60° C. The solid was then heated in ethanol, filtered and the filtrate was concentrated. Water was added to the remaining to obtain a solid that was collected by filtration and dried at 75° C. under vacuum to obtain the title product, m.p. 201°–204° C.

Other compounds prepared by similar procedures:

42) 4-N-(4-pyridylmethylamino)-5-iodo-7-(5-deoxy-1-β-D-ribofuranosyl)pyrrolo[2,34]pyrimidine. Off-white solid. Melting point: 110°–111° C. Rf=0.60 (10% $CH_3OH$ in $CH_2Cl_2$).

43) 4-N-(2-(2-pyridylethyl)amino)-5-iodo-7-(5-deoxy-1-β-D-ribofuranosyl)pyrrolo[2,3-d]pyrimidine. Melting point: 179°–181° C.

44) 4-N-(3-pyridylmethylamino)-5-iodo-7-(5-deoxy-1-β-D-ribofuranosyl)pyrrolo[2,3-d]pyrimidine. White solid. Melting point: 135°–138° C. Rf=0.28 (5% $CH_3OH$ in $CH_2Cl_2$)

45) 4-N-(2-benzimidazolylmethyl)amino-5-iodo-7-(5-deoxy-1-β-D-ribofuranosyl) pyrrolo[(2,3-d)]pyrimidine.

White solid. Melting point: 203°–205° C. Rf=0.49 (10% CH$_3$OH in CH$_2$Cl$_2$).

46) 4-N-(2-pyridylmethyl)amino-5-iodo-7-(a-L-lyxofuranosyl)pyrrolo(2,3-d)pyrimidine. m.p. 214°–216° C.

266) 4-N-[4-(1-Piperidinoethyl)phenyl]amino-5-phenyl-7-(5-deoxy-1-β-D-ribofuranosyl)pyrrolo[2,3-d]pyrimidine. m.p. 150°–152° C.

The intermediates 5-iodo4-(N-phenyl)amino-7-(5-deoxy-2,3-isopropylidene-β-D-ribofuranosyl)pyrrolo[2,3-d]pyrimidine and 5-iodo4-(3-pyridyl)amino-7-(5-deoxy-2,3-isopropylidene-β-D-ribofuranosyl)pyrrolo[2,3-d]pyrimidine can also be prepared in a similar manner.

EXAMPLE 6

Additional Pyrrolo Pyrimidines of the Invention

Preparation of the following additional compounds of the invention is described in this example.

47) 4-N-Phenylamino-5-(3-pyridino)-7-(5-deoxy-1-β-D-ribofuranosyl) pyrrolo[2,3-d]pyrimidine 48) 4-N-(2-pyridylmethyl)amino-5-(3-pyridino)-7-(5-deoxy-1-β-D-ribofuranosyl)pyrrolo[2,3-d]pyrimidine. solid. m.p. 189°–192° C.

49) 4-N-(4-pyridylmethyl)amino-5-phenyl-7-(5-deoxy-1-β-D-ribofuranosyl)-pyrrolo[2,3-d]pyrimidine. m.p. 103°–108° C.

50) 4-N-(3-pyridylmethyl)amino-5-phenyl-7-(5-deoxy-1-β-D-ribofuranosyl)-pyrrolo[2,3-d]pyrimidine. m.p. 211°–212° C.

51) Preparation of 4-N-((methylphosphoryloxy)phenyl)amino-5-phenyl-7-(5-deoxy-1-β-D-ribofuranosyl)pyrrolo[2,3-d]pyrimidine A. Preparation of 4-N-Phenylamino-5-(3-pyridino)-7-(5-deoxy-1-β-D-ribofuranosyl) pyrrolo[2,3-d]pyrimidine (47)

A mixture of 0.35 mmol of 5-iodo4-N-phenyl amino-7-(5-deoxy-2,3-O-isopropylidene 1-β-D-ribofuranosyl) pyrrolo[2,3-d]pyrimidine, 4.4 equivalents of 3-pyridyiboronic acid (Terashima et al., Chem. Pharm. Bull. 31, 4573 (1983)) and 0.16 equivalents of tetrakis triphenylphosphine palladium in a 10 mL of diglyme and 4 mL of ethanol was treated with 2 mL of a saturated sodium carbonate solution and heated to 100° C. for approximately 5 hours. The mixture was allowed to cool to room temperature, an excess of ethyl acetate was added, and the organic layer was washed with diluted sodium bicarbonate solution, water and saturated sodium chloride. The resulting solution was dried over sodium sulfate and evaporated under reduced pressure. The residue was chromatographed on silica using a 3% solution of methanol in methylene chloride to obtain 131 mg of a brown oil with Rf=0.38 (3% CH$_3$OH in CH$_2$Cl$_2$). This oil was stirred at room temperature for 30 min in 70% trifluoroacetic acid:water mixture. The solvent was evaporated under reduced pressure and the residue stirred in methanolic K$_2$CO$_3$ for 5 minutes, filtered through a celite pad and coevaporated with toluene. Filtration through a silica pad using 10% CH$_3$OH in CH$_2$Cl$_2$ as the eluent afforded after evaporation a cream colored solid that was recrystallized from methanol ether. The resulting title compound was an off-white solid with melting point 189–192° C. and Rf=0.27 (5% CH$_3$OH in CH$_2$Cl$_2$).

The following compounds were also prepared in this fashion.

48) 4-N-(2-pyridylmethyl)amino-5-(3-pyridino)-7-(5-deoxy-1-β-D-ribofuranosyl)pyrrolo[2,3-d]pyrimidine. solid. m.p. 189°–192° C.

49) 4-N-(4-pyridylmethyl)amino-5-phenyl-7-(5-deoxy-1-β-D-ribofuranosyl)-pyrrolo[2,3-d]pyrimidine. m.p. 103°–108° C.

50) 4-N-(3-pyridylmethyl)amino-5-phenyl-7-(5-deoxy-1-β-D-ribofuranosyl)-pyrrolo[2,3-d]pyrimidine. m.p. 211°–212° C.

B. Preparation of 4-N-((methylphosphoryloxy)phenyl)amino-5-phenyl-7-(1-β-D-5-deoxyribofuranosyl)pyrrolo[2,3-d]pyrimidine (51)

The compound 4-N-(4-hydroxyphenyl)amino-5-phenyl-7-(5-deoxy-2,3-O-isopyrolidene-1-β-D-ribofuranosyl) pyrrolo[2,3-d]pyrimidine was made by a procedure analogous to Example 5G, by substituting 4-aminophenol for 4-aminoacetanilide. Dimethyl phosphoryl chloridate (1.5 mL) was then added over a 15 minute period to an ice cold solution of this compound (400 mg) in triethyl phosphite (25 mL). After stirring for 5 hours, the reaction mixture was poured over ice (25 g) and stirred. The pH of the solution was adjusted to 7.5 by adding sodium bicarbonate, followed by extraction with ethyl acetate (4×25 mL). Organic layers were combined, dried over anhydrous MgSO$_4$ and evaporated. The residue was chromatographed over silica gel using 9:1 dichloromethane-methanol. The product thus isolated was treated with 70% trifluoroacetic acid for 20 mon. Volatiles were removed under high vacuum and the residue was redissolved in water (20 mL) and passed through a column of Amberlite (400), OH$^-$ form. The column was eluted with water (3×25 ml) and the effluents were discarded. Final elution was done with a solution of 0.5% tert-butylamine in water. Fractions containing the product were collected and evaporated under high vacuum and the residue was redissolved in distilled water (25 mL) and lyophilized until constant weight was attained. The title compound was obtained as a white solid. m.p. 130° C.

Adenosine Kinase Inhibitors Containing Aminoalkyl Carbamoyl and Carboxylic Acid Functions Adenosine kinase inhibitors containing aminoalkyl carbamoyl and carboxylic acid functions (following examples) were synthesized according to the Scheme 4 and Scheme 5 by means of a palladium catalyzed carbonylation of aryl halides that is well known in the literature. (M. Mori, et. al., J. Org. Chem., 43, 1684, (1978).

SCHEME 4
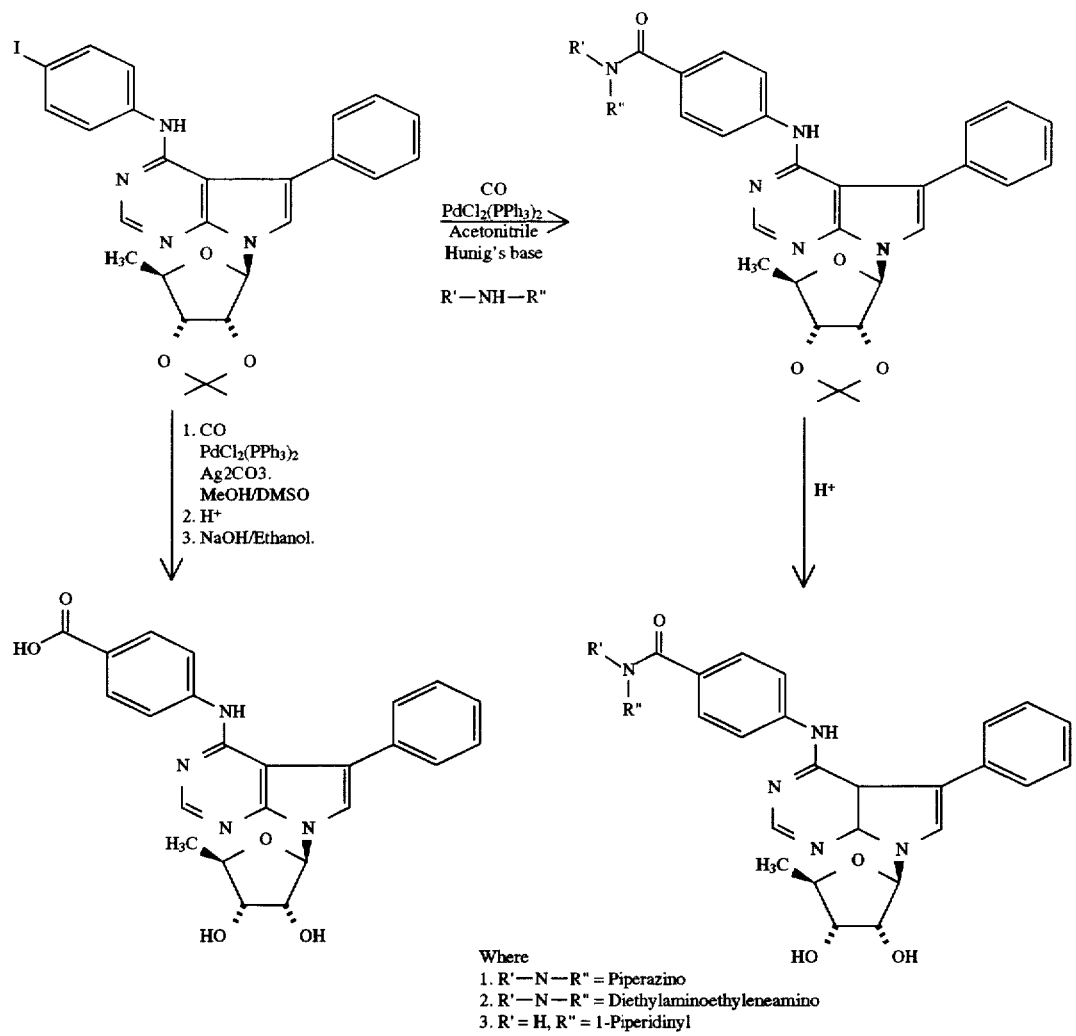
Where
1. R'—N—R" = Piperazino
2. R'—N—R" = Diethylaminoethyleneamino
3. R' = H, R" = 1-Piperidinyl

SCHEME 5

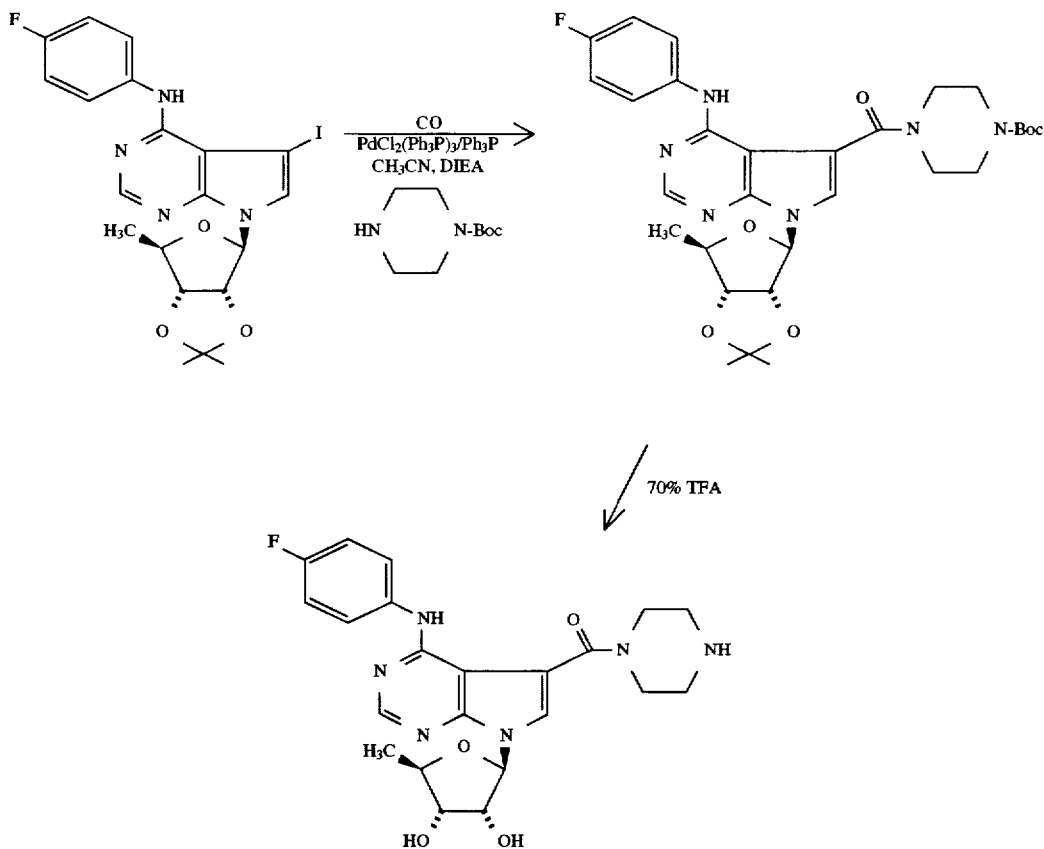

Reaction of 4-N-(4-iodophenyl)amino-5-phenyl-7-(5-deoxy-2,3-isopropylidene-β-D-ribofuranosyl)pyrrolo(2,3-d) pyrimidine with carbon monoxide in presence of a palladium catalyst such as $PdCl_2(PPh_3)_2$ or $Pd(AcO)_2(PPh_3)_2$, an amine nucleophile such as a monoprotected piperazine, and diisopropylethyl amine provide the corresponding carbamoyl intermediates that are deprotected under acidic conditions to provide the final compounds. On the other hand, reaction of the starting iodo compound with carbon monoxide in presence of $Ag_2CO_3$ in methanol-DMSO solvent system using the above mentioned palladium catalysts gives rise to a carboxylic acid methyl ester intermediate. Deprotection of the isopropylidene group under acidic conditions gives the corresponding carboxylic acid.

209) Preparation of 4-N-(4carboxyphenyl)amino-5-phenyl-7-(5-deoxy-1-β-D-ribofuranosyl)pyrrolo[2,3-d] pyrimidine.

The title compound was made by palladium catalyzed carbonylation of 4-N-(4-iodophenyl)amino-5-phenyl-7-(5-deoxy-2,3-isopropylidene-1-β-D-ribofuranosyl)pyrrolo[2,3-d]pyrimidine with carbon monoxide in presence of methanol and subsequent deprotection of sugar moiety, in three steps as follows.

Step 1. Preparation of 4-N-(4-iodophenyl)amino-5-phenylpyrrolo[2,3-d]pyrimidine (207).

This compound was made by a procedure similar to the one described for (6) except that 4-N,N-dimethylaminomethylaniline was replaced with 4-iodoaniline. m.p. 239°–240° C.

Step 2. Preparation of 4-N-(4-iodophenyl)amino-5-phenyl-7-(5-deoxy-2,3-isopropylidene-1-β-D-ribofuranosyl)pyrrolo|2,3-d|pyrimidine (208).

4-N-(4-iodophenyl)amino-5-phenylpyrrolo[2,3-d] pyrimidine was glycosylated with 5-deoxy-2,3-isopropylidene-D-ribofuranose by a procedure similar to the one described for (9). The product was obtained after chromatographic purification as an off white glassy material. Rf=0.55($SiO_2$, 2:1 hexane:ethyl acetate).

Step 3. Preparation of 4-N-(4-carboxyphenyl)amino-5-phenyl-7-(5-deoxy-1-b-D-ribofuranosyl)pyrrolo(2,3-d) pyrimidine (209).

Triethylamine (0.5 mL) was added to a solution of 4-N-(4-Iodophenyl)amino-5-phenyl-7-(5-deoxy-2,3-isopropylidene-1-β-D-ribofuranosyl)pyrrolo[2,3-d] pyrimidine (284 mg.), palladium acetate (40 mg), triphenylphosphine (60, mg), silver carbonate (200 mg), in DMSO (6 mL) and methanol (3 mL) and purged with carbon monoxide thoroughly. The reaction mixture was heated at 60°–70° C. under carbon monoxide atmosphere. After 8.0 hours the reaction mixture was cooled and filtered through a celite filter pad. The filtrate was diluted with water and extracted with methylene chloride (2×20 mL). The organic layers were combined, dried over anhydrous $MgSO_4$, and evaporated. The residue thus obtained was chromatographed over $SiO_2$ using 4:1 hexane: ethyl acetate as the eluting solvent. Fractions containing the desired product were pooled and evaporated to obtain an off white glassy product. Yield, 100 mg. of 4-N-(4-methoxycarbonylphenyl)amino-5-phenyl-7-(5-deoxy-2,3-isopropylidene-1-β-D-ribofuranosyl)pyrrolo(2,3-d)pyrimidine. Rf=0.7 ($SiO_{2,\ 2:1}$ hexane:ethyl acetate). This product was dissolved in methanol (10 mL) containing 0.5 mL of 1N HCl and refluxed gently for one hour. The volatiles were evaporated, the residue was treated with saturated NaHCO₃ solution and extracted with ethyl acetate (2×20 mL). The organic layer was dried over anhydrous sodium sulfate and evaporated under reduced pressure. The residue was suspended in 1N aqueous NaOH solution and methanol (5 mL), and refluxed gently until the tlc showed complete conversion of the starting material to a polar product. The reaction mixture was cooled and neutralized with 1N HCl solution. The precipitate was collected by filtration, washed with water and dried in air. Crystallization from hot ethyl acetate gave the title product as an off white solid. Yield, 35 mg. m.p. 203°–204° C.(decomp). Rf=0.2. (SiO₂, 9:1 CH₂Cl₂: methanol).

210) Preparation of 4-N-[4-(4-piperazinocarbonylphenyl)] amino-5-phenyl-7-(5-deoxy-1-β-D-ribofuranosyl)pyrrolo [2,3-d]pyrimidine.

A solution of 4-N-(4-iodophenyl)amino-5-phenyl-7-(5-deoxy-2,3-isopropylidene-1-β-D-ribofuranosyl)pyrrolo[2,3-d]pyrimidine (284 mg), 1-t-butyloxycarbonylpiperazine (140 mg) and diisopropylethylamine (0.5 mL) in dry acetonitrile was first purged with N₂ followed by carbon monoxide. To the reaction mixture PdCl₂(PPh₃)₂(140 mg) was added and heated to 80° C. for 5 hours under carbon monoxide atmosphere. Tlc (SiO₂, 3:1 ethyl acetate:hexane) indicated complete conversion of the starting material. The reaction mixture was cooled and filtered through a celite pad followed by washing with acetonitrile (2×5 mL). The combined filtrate and the washings were evaporated to dryness and the residue was chromatographed over silica gel using 1:1 hexane:ethyl acetate as the eluting solvent. Fractions containing the desired product were pooled and evaporated to obtain 4-N-[4-(4-Piperazinocarbonylphenyl)amino-5-phenyl-7-(5-deoxy-2,3-isopropylidene-5-deoxy-2,3-O-isopropylidene-1-β-D-ribofuranosyl)pyrrolo[2,3-d] pyrimidine as an off-white foam. Yield 220 mg. Rf=0.3 (SiO₂, 3:1 ethyl acetate:hexane). This material was further dissolved in methanol (25 mL) containing 15 mL of 1N HCl and gently refluxed for 90 minutes. Methanol was evaporated and pH of the solution was adjusted to ~7.6 with aqueous NaHCO₃ solution. The solid thus formed was collected by filtration, washed with water and chromatographed over silica gel using 4:1 dichloromethane-methanol. Fractions containing the product were pooled and evaporated to obtain an off white solid that was further crystallized from boiling ethanol. Yield 230 mg. m.p. 172° C. Rf=0.4 (SiO₂, 4:1 CH₂Cl₂—methanol).

211) Preparation of 4-N-[4-(N,N-diethylaminoethyleneaminocarbonylphenyl)amino-5-phenyl-7-(5-deoxy-1-β-D-ribofuranosyl)pyrrolo[2,3-d] pyrimidine.

This compound was made by a procedure similar to the one mentioned for 4-N-[4-(4-piperazinocarbonylphenyl) amino-5-phenyl-7-(5-deoxy-1-β-D-ribofuranosyl)pyrrolo (2,3-d)pyrimidine except that the 1-t-butyloxycarbonylpiperazine was replaced with N,N-Diethylaminoethylamine. m.p. 128° C. Rf=0.3. (SiO₂, 9:1 CH₂Cl₂:methanol).

212) Preparation of 4-N-[4-(piperidine-N-aminocarbonylphenyl)amino-5-phenyl-7-(5-deoxy-1-β-D-ribofuranosyl)pyrrolo(2,3-d)pyrimidine.

This compound made by a procedure similar to the one mentioned for 4-N-[4-(4-piperazinocarbonylphenylamino-5-phenyl-7-(5-deoxy-1-β-D-ribofuranosyl)pyrrolo[2,3-d] pyrimidine except that the 1-t-butyloxycarbonypiperizine was replaced with N,N-Diethylaminoethylamine. m.p. 128° C. Rf=0.4. (SiO₂, 9:1 CH₂Cl₂:methanol).

213) Preparation of 4-N-(4-fluorophenyl)amino-5-(4-piperazino-carbonyl)-7-(5-deoxy-1-β-D-ribofuranosyl) pyrrolo[2,3-d]pyrimidine A solution of 4-N-(4-flurophenyl)amino-5-iodo-7-(5-deoxy-2,3-O-isopropylidene-1-β-D-ribofuranosyl)pyrrolo |2,3-d|pyrimidine (382 mg), 1-t-butyloxycarbonylpiperazine (210 mg) and diisopropylethylamine (0.75 mL) in dry acetonitrile (5 mL) was first purged with N₂ followed by carbon monoxide. To the reaction mixture PdCl₂(PPh₃)₂ (140 mg) was added and heated to 80° C. for 20 hours under carbon monoxide atmosphere. Tlc (SiO₂, 3:1 ethyl acetate:hexane) indicated complete conversion of the starting material. The reaction mixture was cooled and filtered through a celite pad followed by washing with acetonitrile (2×5 mL). The combined filtrate and the washings were evaporated to dryness and the residue was chromatographed over silica gel using 1:1 hexane:ethyl acetate as the eluting solvent. Fractions containing the desired product were pooled and evaporated to obtain 4-N-[4-(4-fluorophenyl)amino-5-[4-(1-tert-butyloxycarbonyl)piperazinocarbonyl)-7-(5-deoxy-2,3-O-isopropylidene-1-β-D-ribofuranosyl)pyrrolo[2,3-d] pyrimidine as an off-white foam. Yield 310 mg. Rf=0.3 (SiO₂, 3:1 ethyl acetate:hexane). This material was further dissolved in 70% trifluoroacetic acid solution and gently refluxed for 90 minutes. Volatiles were evaporated and the residue was treated with aqueous NaHCO₃ solution. The resulting mixture was extracted with ethyl acetate (2×20 mL) and the organic layers were combined, dried over anhydrous sodium sulfate and evaporated to obtain an off white solid. It was further crystallized from boiling ethanol. Yield 150 mg. m.p. 158°–159° C. Rf=0.6(SiO₂, 6:1 CH₂Cl₂:methanol).

Synthesis of 5-Sudstituted Pyrrolo[2,3-d] Pyrimidines

Pyrrolo[2,3-d]pyrimidine analogs substituted at the 5-position with an alkyl, alkenyl or alkynyl group are considered to fall within the scope of the present invention. These alkyl, alkenyl or alkynyl groups may contain one or more heteroatoms and may be either in the open chain or the cyclic form. The synthesis of 4-N-arylamino-5-substituted pyrrolo[2,3-d]pyrimidines can be achieved by application of the methods illustrated by Friesen and Sturino (J. Org. Chem. 55, 2572 (1990)), from a suitably functionalized 4-N-arylamino-5-iodo-pyrrolo[2,3-d]pyrimidine and an unsaturated trialkyl stannane in the presence of a palladium catalyst. The 5-alkenyl derivative so obtained can by hydrogenated in order to prepare the corresponding alkyl analog. Alternatively, the reaction of a functionalized 4-N-arylamino-5-iodo-pyrrolo[2,3-d]pyrimidine with an olefin under Heck arylation conditions (Heck et al. J. Org. Chem. 43, 2454 (1978), J. Org. Chem. 43, 2954 (1990)) could also give rise to a 5-alkenyl derivative which in turn can be hydrogenated to give the corresponding 5-alkyl analogs.

The preparation of 5-alkynyl derivatives can be accomplished by reaction of a suitably functionalized 4-N-arylamino-5-iodo-pyrrolo[2,3-d]pyrimidine and an alkyne in the presence of a palladium catalyst as is well known in the literature (R. C. Larock, "Comprehensive Organic Transformations: A Guide to Functional Group Preparations", VCH Publishers, Inc. 1989 pg. 302). The preparation of 5-dioxolane derivatives of pyrrolo|2,3-d|pyrimidines can be achieved by reaction of a suitably functionalized 4-N-arylamino-5-iodo-pyrrolo[2,3-d]pyrimidine with carbon monoxide under palladium catalized conditions as described in the literature (R. C. Larock, "Comprehensive Organic Transformations: A Guide to Functional Group Preparations", VCH Publishers, Inc. 1989 pg. 678) to afford a 5-formylpyrrolo|2,3-d|pyrimidine which can be later reacted with a diol under acidic conditions as described, for example, by Astles et al (*J. Med. Chem.* 39, 1423 (1996)) to generate the target dioxolane.

Synthesis of Pyrazolo Pyrimidines

Still another aspect of this invention is the preparation of 5'-substituted pyrazolo[3,4-d]pyrimidine ribosides. Accordingly, a substituted pyrazolo[3,4-d]pyrimidine is ribosylated with an esterified 5-hydroxy, 5-azido or 5-deoxyribofuranoside in the presence of a Lewis acid such as boron trifluoride. Browne et al., Ser. No. 08/812,916; Cottam, et al., *J. Med. Chem.*, 27:1120 (1984).

EXAMPLE 7

Preparation of Pyrazolo Pyrimidines

The 5-substituted ribofuranoside is prepared by esterification of the deblocked sugar. Suitable esters include the acetate, benzoate, toluate, anisoate and the like. The substituted pyrazolo[3,4-d]pyrimidine base may be prepared by a variety of known procedures which are apparent to practitioners.

One route comprises coupling an esterified ribose prepared as described above with a 3-substituted pyrazolo[3,4-d]pyrimidone-4-one. After ribosylation the pyrimidine riboside may be activated by chlorination with thionyl chloride/dimethyl-formamide or similar reagents and then reacted with ammonia or an amine to provide a variety of 5'-modified N4-substitutedamino-pyrazolo[3,4-d] pyrimidine nucleosides. Another route for preparation of substituted pyrazolo[3,4-d]pyrimidine nucleosides comprises coupling the esterified ribose with various substituted 4-amino or 4-substituted aminopyrazolo[3,4-d]pyrimidines. The resulting products are then further modified or deblocked to afford the desired compounds. For example, 3-phenyl4-phenylaminopyrazolo[3,4-d]pyrimidine 5'-modified ribosides are prepared from 3-phenyl4-phenylaminopyrazolo[3,4-d]pyrimidine and various 5-modified sugars.

In another aspect of the present invention, 3-halogenated pyrazolo[3,4-d]pyrimidine ribosides can be arylated using arylboronic acids and palladium catalysts as described for the pyrrolo[2,3-d]pyrimidines. Thus, 3-iodopyrazolo[3,4-d] pyrimidone nucleosides are prepared by nonaqueous diazotization-iodination of the 3-amino compounds using a nitrite ester such as isoamyl nitrite and methylene iodide. Alternatively, 4-chloro or 4-amino pyrazolo(3,4-d) pyrimidine may be iodonated using N-iodosuccinide in a solvent such as DMF and the resulting 5-iodo heterocycle is coupled to the sugar to obtain the desired 4-iodonated pyrazolo(3,4-d)pyrimidine nucleoside.

Further modifications include reduction of the 5'-azido moiety to afford the 5'-amino compounds or the 5'-amides and urethanes as described above. Ester prodrugs ($C_1$ and $C_2$) of various 5'-amino nucleosides are prepared by reduction of the 5'-azide esters using previously described reagents.

EXAMPLE 8

Preferred Preparation of Pyrazolo Compounds

The general route for the synthesis of various 3-aryl4-arylaminopyrazolo(3,4-d)pyrimidine nucleosides is delineated in Scheme 6. Various 3-aryl substituted 5-aminopyrazole-4-carbonitriles (17) are synthesized by a procedure analogous to the one reported in Kobayashi, *Chem. Pharm. Bull.* (Japan) 21, 941 (1973). These intermediates are further converted by a three step procedure to provide the heterocycles (18) used for synthesis of final compounds. Cheng, C. C., Robins, R. K., *J. Org. Chem.*, 21, 1240 (1966).

The carbohydrate moieties used in the current invention, e.g. 5-azido-5-deoxy-1,2,3-tri-O-acetyl-ribofuranose (22), where $B=CH_2N_3$ is synthesized as shown in Scheme 6. Treatment of (20) (Snyder et al., *Carbohydrate Research*, 163: 169 (1987)) with sodium azide in dry DMF at elevated temperatures provided the corresponding 5-azido ribofuranoside (21) which is subjected to removal of the protecting groups under acidic conditions and the resulting 5-azido-5-deoxy-ribose is acetylated with acetic anhydride and pyridine to provide (22).

5-Deoxy-1,2,3-tri-O-acetyl-D-ribofuranose used in the current invention is synthesized by subjecting (23) to LAH reduction to provide methyl 5-deoxy-2,3-isopropylidene-D-ribofuranose (20) (Scheme 6). It was subjected to same protecting group manipulations as above to obtain (23) (where $B=CH_2H$). See, e.g. Formula 1 and Snyder et al., *Carbohydrate Research*, 163: 169 (1987).

The intermediate 1-O-acetyl-2,3,5-tri-O-benzoyl-L-lyxofuranoside used to synthesize the lyxose derivative of the invention can be made by treating L-lyxose (commercially available) with methanolic HCl at room temperature to provide 1-O-methyl-L-lyxofuranoside. This intermediate is then treated with benzoic anhydride in pyridine to provide methyl 2,3,5-O-tri-O-benzoyl-L-lyxofuranoside, which can be treated with acetic anhydride in an acetic acid/sulfuric acid mixture at 0° C. to provide the desired sugar.

SCHEME 6

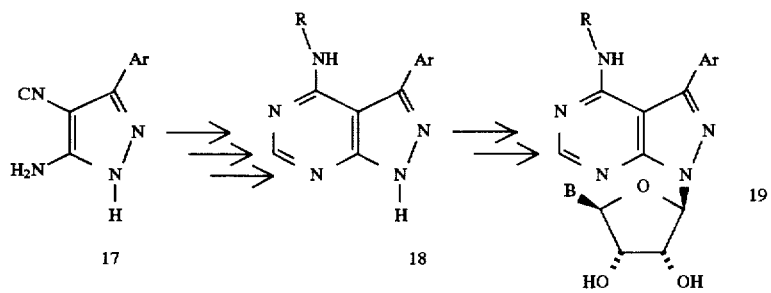

-continued
SCHEME 6

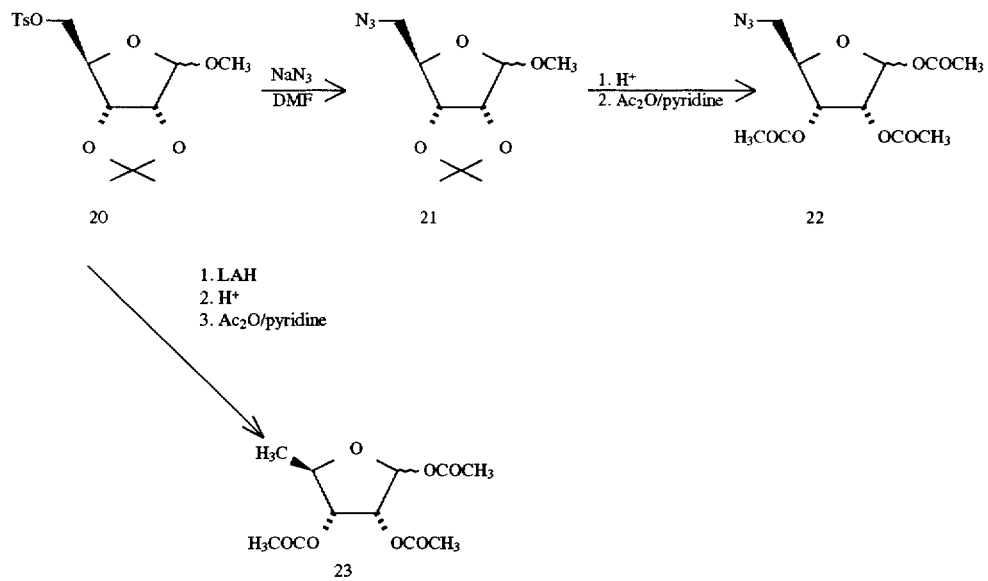

Coupling of heterocycles with the above ribofuranose (or lyxofuranose) 5 moieties can be conducted in boiling nitromethane using $BF_3$-etherate as a catalyst to obtain blocked nucleosides which upon deblocking with sodium methoxide in methanol provides the desired 5'-modified 3-aryl-4-arylaminopyrazolo(3,4-d)pyrimidine nucleosides of general structure (19).

The following examples can be synthesized by same procedure.

52) 3-(4-N,N-Dimethylaminoethylphenyl)-4-N-(4-fluoropheny)amino-1-(5-deoxy-β-D-ribofuranosyl)pyrazolo(3,4-d)pyrimidine.
53) 3-(4-N,N-Diethylaminomethylphenyl)-4-N-(4-fluorophenyl)amino-1-(5-deoxy-β-D-ribofuranosyl)pyrazolo(3,4-d)pyrimidine.
54) 3-(4-N,N-Dimethylaminoethylphenyl)-4-N-(4-fluorophenyl)amino-1-(5-deoxy-β-D-ribofuranosyl)pyrazolo(3,4-d)pyrimidine.
55) 3-(4-Morpholinomethylphenyl)-4-N-(4-fluorophenyl)amino-1-(5-deoxy-β-D-ribofuranosyl)pyrazolo(3,4-d)pyrimidine.
56) 3-(4-Morpholinoethylphenyl)-4-N-(4-fluorophenyl)amino-1-(5-deoxy-β-D-ribofuranosyl)pyrazolo(3,4-d)pyrimidine.
57) 3-(1-Piperidinomethylphenyl)-4-N-(4-fluorophenyl)amino-1-(5-deoxy-β-D-ribofuranosyl)pyrazolo(3,4-d)pyrimidine.
58) 3-(1-Piperidinoethylphenyl)-4-N-(4-fluorophenyl)amino-1-(5-deoxy-β-D-ribofuranosyl)pyrazolo(3,4-d)pyrimidine.
59) 4-N-(1-Piperizinomethylphenyl)amino-3-phenyl-1-(5-deoxy-β-D-ribofuranosyl)pyrazolo(3,4-d)pyrimidine.
60) 3-(1-Piperizinoethylphenyl)-4-N-(4-fluorophenyl)amino-1-(5-deoxy-β-D-ribofuranosyl)pyrazolo(3,4-d)pyrimidine.
61) 3-(4-Trifluoroacetamidophenyl)-4-N-(4-fluorophenyl)amino-1-(5-deoxy-β-D-ribofuranosyl)pyrazolo(3,4-d)pyrimidine.
62) 3-(4-Trifluoroacetylaminosulfonylphenyl)-4-N-(4-fluorophenyl)amino-1-(5-deoxy-β-D-ribofuranosyl)pyrazolo(3,4-d)pyrimidine.
63) 3-(4-N-Guanidinophenyl)-4-N-(4-fluorophenyl)amino-1-(5-deoxy-β-D-ribofuranosyl)pyrazolo(3,4-d)pyrimidine.
64) 3-(4-C-Amidinophenyl)-4-N-(4-fluorophenyl)amino-1-(5-deoxy-β-D-ribofuranosyl)pyrazolo(3,4-d)pyrimidine.
65) 3-(4-Carboxyphenyl)-4-N-(4-fluorophenyl)amino-1-(5-deoxy-β-D-ribofuranosyl)pyrazolo(3,4-d)pyrimidine.

Lyxose analogs can also be prepared, for example:

66) 3-(4-N,N-Dimethyaminomethylphenyl)-4-N-(4-fluorophenyl)amino-1-(1-α-L-lyxofuranosyl)pyrazolo(3,4-d)pyrimidine.
67) 3-(4-N,N-Dimethyaminoethylphenyl)-4-N-(4-fluoropheny)amino-1-(1-α-L-lyxofyranosyl)pyrazolo(3,4-d)pyrimidine.
68) 3-(4-N,N-Diethylaminomethylphenyl)-4-N-(4-fluorophenyl)amino-1-(1-α-L-lyxofyranosyl)pyrazolo(3,4-d)pyrimidine.
69) 3-(4-N,N-Dimethyaminoethylphenyl)-4-N-(4-fluorophenyl)amino-1-(1-α-L-lyxofyranosyl)pyrazolo(3,4-d)pyrimidine.
70) 3-(4-Morpholinomethylphenyl)-4-N-(4-fluorophenyl)amino-1-(1-α-L-lyxofyranosyl)pyrazolo(3,4-d)pyrimidine.
71) 3-(4-Morpholinoethylphenyl)-4-N-(4-fluorophenyl)amino-1-(1-α-L-lyxofyranosyl)pyrazolo(3,4-d)pyrimidine.
72) 3-(1-Piperidinomethylphenyl)-4-N-(4-fluorophenyl)amino-1-(1-α-L-lyxofyranosyl)pyrazolo(3,4-d)pyrimidine.
73) 3-(1-Piperidinoethylphenyl)-4-N-(4-fluorophenyl)amino-1-(1-α-L-lyxofyranosyl)pyrazolo(3,4-d)pyrimidine.
74) 4-N-(1-Piperizinomethylphenyl)amino-3-phenyl-1-(1-α-L-lyxofyranosyl)pyrazolo(3,4-d)pyrimidine.
75) 3-(1-Piperizinoethylphenyl)-4-N-(4-fluorophenyl)amino-1-(1-α-L-lyxofyranosyl)pyrazolo(3,4-d)pyrimidine.
76) 3-(4-Trifluoroacetamidophenyl)-4-N-(4-fluorophenyl)amino-1-(1-α-L-lyxofyranosyl)pyrazolo(3,4-d)pyrimidine.
77) 3-(4-Trifluoroacetylaminosulfonylphenyl)-4-N-(4-fluorophenyl)amino-1-(1-α-L-lyxofyranosyl)pyrazolo(3,4-d)pyrimidine.

78) 3-(4-N-Guanidinophenyl)-4-N-(4-fluorophenyl)amino-1-(1-α-L-lyxofyranosyl)pyrazolo(3,4-d)pyrimidine.
79) 3-(4—C-Amidinophenyl)-4-N-(4-fluorophenyl)amino-1-(1-α-L-lyxofyranosyl)pyrazolo(3,4-d)pyrimidine.
80) 3-(4-Carboxyphenyl)-4-N-(4-fluorophenyl)amino-1-(1-α-L-lyxofyranosyl)pyrazolo(3,4-d)pyrimidine.

EXAMPLE 9

Synthesis of Heterocycles

Heterocycles made according to this example were used in the previous example (Scheme 4). The following heterocycles, used as starting materials in this example, were made by procedures analogous to those in Kobayashi, Chem. Pharm. Bull. (Japan), (1973), 21, 941 (1973) and Cheng, et al. J. Org. Chem., 21, 1240 (1966).

Pyrazolo(3 4-d)pyrimidine heterocycles synthesized by the above procedure 1. 4-N-(N,N-Dimethylaminomethylphenyl)amino-3-phenylpyrazolo(3,4-d)pyrimidine
2. 4-N-(N,N-Diethylaminomethylphenyl)amino-3-phenylpyrazolo(3,4-d)pyrimidine
3. 4-N-(N,N-Diethylaminoethylphenyl)amino-3-phenylpyrazolo(3,4-d)pyrimidine
4. 4-N-(N,N-Dimethylaminoethylphenyl)amino-3-phenylpyrazolo(3,4-d)pyrimidine
5. 4-N-(N,N-Diethylaminoethyleneaminophenyl)amino-3-phenylpyrazolo(3,4-d)pyrimidine
6. 4-N-(2-(1-piperazino)ethylphenyl)amino-3-phenylpyrazolo(3,4-d)pyrimidine
7. 4-N-(2-(1-Piperidino)ethylphenyl)amino-3-phenylpyrazolo(3,4-d)pyrimidine
8. 4-N-(2-(4-Morpholino)ethylphenyl)amino-3-phenylpyrazolo(3,4-d)pyrimidine
9. 4-N-(4-Cyanophenyl)amino-3-phenylpyrazolo(3,4-d) pyrimidine
10. 3-(N,N-Dimethylaminomethylphenyl)-4-N(4-fluorophenyl)aminopyrazolo(3,4-d)pyrimidine
11. 3-(N,N-Diethylaminomethylphenyl)-4-N-(4-fluorophenyl)aminopyrazolo(3,4-d)pyrimidine
12. 3-N-(N,N-Diethylaminoethylphenyl)-4-N-(4-fluorophenyl)aminopyrazolo(3,4-d)pyrimidine
13. 3-(N,N-Dimethylaminoethylphenyl)-4-N-(4-fluorophenyl)aminopyrazolo(3,4-d)pyrimidine
14. 3-(N,N-Diethylaminoethyleneaminophenyl)-4-N-4-fluorophenyl)aminopyrazolo(3,4-d)pyrimidine
15. 3-(2-(1-piperazino)ethylphenyl)-4-N-(4-fluorophenyl) aminopyrazolo(3,4-d)pyrimidine.

A. Preparation of 5-Azido-5-deoxy-1-O-methyl-2,3-O-(1-methylethylidene)-D-ribofuranoside (21).

A mixture of 1-O-methyl-2,3-O-(1-methylethylidene)-5-O-(4-methylbenzenesulfonyl)-D-ribofuranoside (20) (8.0 g), dry DMF (40 mL) and NaN$_3$ (4.0 g) was heated at 80° C. for 12 hours. The solvent was evaporated and the residue was chromatographed over silica gel using CH$_2$Cl$_2$. The fractions containing the faster moving product were pooled and evaporated to obtain 4.8 g (94% yield) of a syrupy product.

B. Preparation of 5-azido-5-deoxy-1,2,3-O-Triacetyl-D-ribofuranoside (22)

A solution of 5-azido-5-deoxy-1-O-methyl-2,3-O-(1-methylethylidene)-D-ribofuranoside (21), 4.6 g, 20 mmol in 0.1% H$_2$SO$_4$ (300 mL) was refluxed for 3 hours. The acid was neutralized (pH ~5) with Amberlite 400 (OH⁻form) and the resin filtered and washed with ethanol (2×20 mL). The filtrate was evaporated to dryness under high vacuum to give the title compound as a syrupy residue; $^1$H and $^{13}$C NMR confirmed the identity of the product as a mixture of α and β anomers. This product(3.1 g, 0.017 mole) was dissolved in 10 ml of pyridine and was treated with acetic anhydride (18 ml). The mixture stirred for 24 hours and concentrated under vacuum. The residue was dissolved in CH$_2$Cl$_2$ and the solution washed with 5% NaHCO$_3$. The organic layer was then washed with 0.5N H$_2$SO$_4$, dried (Na$_2$SO$_4$) and evaporated. The residue was filtered through a plug of silica gel (CH$_2$Cl$_2$) and the filtrate concentrated to afford the title compound, 4.5 g (98% yield) as a semisolid mixture of α and β isomers.

C. Preparation of 5-deoxy-1,2,3-tri-O-acetyl-D-ribofuranoside (23)

This compound was prepared as described in Snyder, J.; Serianni, A.; Carbohydrate Research, 163:169 (1987).

D. Synthesis of 3-aryl4-arylaminopyrazolo(3,4-d) pyrimidine nucleosides (19)

To a slurry of the heterocycle (18) (5.0 mmol) in nitromethane under argon, was added acyl protected ribofuranose(5-7 mmol). The mixture was heated approximately to 80° C. and treated with BF$_3$-etherate(7.0 mmol). The reaction mixture was refluxed gently for 90 minutes, then cooled and evaporated under vacuum The residue was treated with triethyl amine and water and extracted with methylene chloride. The organic layer was dried over sodium sulfate and evaporated. The residue was chromatographed over silica gel using gradient of ethyl acetate and hexane as eluting system. The product thus obtained was dissolved in methanol and treated with freshly prepared sodium methoxide solution to adjust the pH to ~10. After stirring the reaction for 2 hours the pH of the solution was adjusted to 4 by adding strongly acidic resin Dowex-120 H⁺ type. The resin was filtered off, washed with methanol and the filtrate was evaporated under reduced pressure. The residue was crystallized from appropriate solvent. It will be readily apparent that many compounds, including those in Formula 1 above, and in the appended claims, can be made by these various exemplary methods.

EXAMPLE 10

Representative Preferred Pyrrolo[2,3-d]Pyrimidines

Representative, preferred pyrrolo[2,3-d]pyrimidine compounds of the invention, which are not limiting, are identified below. Generally, the most preferred compounds have two aryl groups (e.g. phenyl or substituted phenyl) at positions D and W of the formula below (W corresponds to (CH$_2$)$_p$X of Formula 1). Particularly preferred are compounds where D is phenyl. A$_1$, A$_2$, G and E of Formula 1 are all hydrogen, and B of Formula 1 is methyl. B may also be CH$_2$OH, and in that case a particularly preferred compound is 81) 4-N-(4-N,N-dimethylaminomethylphenyl)amino-5-phenyl-7-(1-β-D-ribofuranosyl)pyrrolo[2,3-d] pyrimidine.

Thus, particularly preferred pyrrolo pyrimidines of the invention can be represented by the following formula:

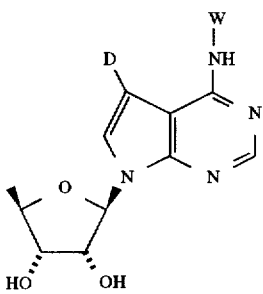

where D is most preferably (a) phenyl, or is preferably (b) 3-pyridyl, (c) 4-(1-morpholinomethyl)phenyl, (d) 4-(1-piperidinoethyl)phenyl, (e) 4-(1-piperizinoethyl)phenyl, (f) 4-(2-aminoethyl)phenyl, (g) 4-(N,N-dimethylaminomethyl)phenyl, (h) 4-(N,N-diethylaminomethyl)phenyl, or (I) 4-(N,N-diethylaminoethyl)phenyl.

When D is phenyl, preferred compounds are those where W is:

82) 4-((Methylphosphoryl)oxy)phenyl
83) phenyl
84) (4-(2-Aminoethyl)phenyl
85) 4-(1-morpholino-2-ethylphenyl)
86) 4-(N-Acetylaminosulfonyl)phenyl
87) 4-(1-piperazinoethyl)phenyl
88) 4-N,N-Dimethylaminomethylphenyl
89) 4-(diethylaminoethyleneaminoethyl)phenyl
90) 4-(2-diethylaminoethyl)phenyl)
91) 4-(2-dimethylaminoethyl)phenyl
92) 4-N-Trifluoromethanesulfonylaminophenyl
93) (4-amidoxime)phenyl
94) 4-phosphatephenyl
95) 4-N-aminoamidinophenyl
96) 4-N-aminoguanidinophenyl
97) 4-carboxymethyloxyphenyl
98) 4-(2-aminoethyl)carboxamidophenyl
99) 4-(2-N,N-diethylaminoethyl)carboxamidophenyl
100) 4-(morpholinoethyl)carboxamidophenyl
101) 4-(1-pyperazinoethyl)carboxamidophenyl
102) 4-(pyperidinoethyl)carboxamidophenyl
103) 4-(N-ethylaminomethyl)phenyl
104) 4-(N-methylaminomethyl)phenyl
105) 3-(N,N-dimethylaminomethyl)phenyl
106) 4-(N,N-dimethylaminomethyl)phenyl
107) 3-(N,N-diethylaminomethyl)phenyl
108) 4-(N,N-diethylaminomethyl)phenyl
109) 3-(N,N-dimethylaminoethyl)phenyl
110) 3-(N,N-diethylaminoethyl)phenyl
111) 4-(N,N-diethylaminoethyl)phenyl
112) 3-(N,N-diethylaminopropyl)phenyl
113) 4-hydroxypropylphenyl
114) 4-(3-aminopropyl)phenyl
115) 4-(N,N-diethylaminopropyl)phenyl
116) 3-(1-piperidinomethyl)phenyl
117) 4-(N-trifluoromethanesulfonamido)phenyl
118) 4-N-fluorosulfonylaminophenyl When D is 3-pyridyl, preferred compound are those where W is:

119) phenyl
120) 4-fluorophenyl
121) 2-pyridinomethyl; or
122) 4-dimethylaminomethylphenyl.

When D is any of the groups (c)–(I) immediately above, then W is preferably fluorophenyl (Examples 124–130, respectively).

Other preferred pyrrolo pyrimidine compounds of the invention are those where D is iodo, and especially preferred compounds of this kind are those where W is 41) 2-pyridylmethyl (see also #46)
42) 4-pyridylmethyl
43) 2-pyridylethyl
44) 3-pyridylmethyl
45) 2-benzimidazolylmethyl
131) 2-thiophenylmethyl If desired, the compounds of the invention can be provided as salts, e.g. hydrochloride salts, such as 4-(2-pyridylmethylamino)-5-iodo-7-(5-deoxy-1-β-D-ribofuranosyl)pyrrolo[2,3-d]pyrimidine hydrochloride (Examples 41 and 46). Compounds having a lyxose sugar moiety, in place of ribose, can also be provided. As one example, the following compounds, corresponding to Examples 41 and 42 are within the scope of the invention:

132) 4-N-(2-pyridylmethylamino)-5-iodo-7-(1-α-L-lyxofuranosyl)pyrrolo[2,3-d]pyrimidine; and
133) 4-N-(4-pyridylmethylamino)-5-iodo-7-(1-α-L-lyxofuranosyl)pyrrolo[2,3-d]pyrimidine.

The following compounds fall within the scope of this application and can be synthesized by the methods disclosed:

215) 4-N-(4-(2-N-(1,2-Dioxo-3-hydroxy-3-cyclobuten-4-yl)aminoethyl)phenyl)amino-5-phenyl-7-(5-deoxy-1-β-D-ribofuranosyl) pyrrolo[2,3-d]pyrimidine
216) 4-N-(4-Fluorophenyl)amino-5-(2-N-(1,2-Dioxo-3-hydroxy-3-cyclobuten-4-yl)aminoethyl)phenyl-7-(5-deoxy-1-β-D-ribofuranosyl) pyrrolo[2,3-d]pyrimidine
217) 4-N-(4-(2-N-(1,2-Dioxo-3-hydroxy-3-cyclobuten-4-yl)amino)phenyl)amino-5-phenyl-7-(5-deoxy-1-β-D-ribofuranosyl) pyrrolo[2,3-d]pyrimidine
218) 4-N-(4-(2-N-(1,3-diaza-1-cyclohexen-2-yl)aminoethyl)phenyl)amino-5-phenyl-7-(5-deoxy-1-β-D-ribofuranosyl) pyrrolo[2,3-d]pyrimidine
219) 4-N-(4-Fluorophenyl)amino-5-(4-(2-N-(1,3-diaza-1-cyclohexen-2-yl)aminoethyl))phenyl-7-(5-deoxy-1-β-D-ribofuranosyl) pyrrolo[2,3-d]pyrimidine
220) 4-N-(4-(2-N-(1,3-diaza-1-cyclopenten-2-yl)aminoethyl)phenyl)amino-5-phenyl-7-(5-deoxy-1-β-D-ribofuranosyl) pyrrolo[2,3-d]pyrimidine
221) 4-N-(4-Fluorophenyl)amino-5-(4-(2-N-(1,3-diaza-1-cyclopenten-2-yl)aminoethyl))phenyl-7-(5-deoxy-1-β-D-ribofuranosyl) pyrrolo[2,3-d]pyrimidine
222) 4-N-(4-(2-N-(1,3-diaza-1-cyclohexen-2-yl)amino)phenyl)amino-5-phenyl-7-(5-deoxy-1-β-D-ribofuranosyl) pyrrolo[2,3-d]pyrimidine
223) 4-N-(4-Fluorophenyl)amino-5-(4-(2-N-(1,3-diaza-1-cyclohexen-2-yl)amino))phenyl-7-(5-deoxy-1-β-D-ribofuranosyl) pyrrolo[2,3-d]pyrimidine
224) 4-N-(4-(2-N-(1,3-diaza-1-cyclopenten-2-yl)amino)phenyl)amino-5-phenyl-7-(5-deoxy-1-β-D-ribofuranosyl) pyrrolo[2,3-d]pyrimidine
225) 4-N-(4-Fluorophenyl)amino-5-(4-(2-N-(1,3-diaza-1-cyclopenten-2-yl)amino))phenyl-7-(5-deoxy1-β-D-ribofuranosyl) pyrrolo[2,3-d]pyrimidine
226) 4-N-(4-Fluorophenyl)amino-5-(3-(2-N-(1,3-diaza-1-cyclopenten-2-yl)amino))phenyl-7-(5-deoxy-1-β-D-ribofuranosyl) pyrrolo[2,3-d]pyrimidine

47

227) 4-N-(4-Fluorophenyl)amino-5-(4-(2-(1-piperidinoethyl)))phenyl-7-(5-deoxyl-β-D-ribofuranosyl) pyrrolo|2,3-d|pyrimidine
228) 4-N-(4-(1,3-Diaza-1-cyclopenten-2-yl)methylphenyl)amino-5-phenyl-7-(5-deoxy-1-β-D-ribofuranosyl) pyrrolo|2,3-d|pyrimidine
229) 4-N-(4-(1,3-diaza-1-cyclohexen-2-yl)methylphenyl)amino-5-phenyl-7-(5-deoxyl-β-D-ribofuranosyl) pyrrolo|2,3-d|pyrimidine
230) 4-N-(4-(1,3-Diaza-1-cyclopenten-2-yl)phenyl)amino-5-phenyl-7-(5-deoxy-1-β-D-ribofuranosyl) pyrrolo|2,3-d|pyrimidine
231) 4-N-(4-(1,3-Diaza-1-cyclohexen-2-yl)phenyl)amino-5-phenyl-7-(5-deoxy-1-β-D-ribofuranosyl) pyrrolo|2,3-d|pyrimidine
232) 4-N-(4-Fluorophenyl)amino-5-(4-(1,3-diaza-1-cyclopenten-2-yl)methyl)phenyl-7-(5-deoxy-1-β-D-ribofuranosyl) pyrrolo|2,3-d|pyrimidine
233) 4-N-(4-Fluorophenyl)amino-5-(4-(1,3-diaza-1-cyclohexen-2-yl)methyl)phenyl-7-(5-deoxy-1-β-D-ribofuranosyl) pyrrolo|2,3-d|pyrimidine
234) 4-N-(4-Fluorophenyl)amino-5-(4-(1,3-diaza-1-cyclopenten-2-yl))phenyl-7-(5-deoxy-1-β-D-ribofuranosyl) pyrrolo|2,3-d|pyrimidine
235) 4-N-(4-Fluorophenyl)amino-5-(4-(1,3-diaza-1-cyclohexen-2-yl)phenyl)phenyl-7-(5-deoxy-1-β-D-ribofuranosyl) pyrrolo|2,3-d|pyrimidine
236) 4-N-(4-(2-(1-Imidazolyl)ethyl)phenyl)amino-5-phenyl-7-(5-deoxy-1-β-D-ribofuranosyl)pyrrolo[2,3-d]pyrimidine
237) 4-N-(4-Fluorophenyl)amino-5-(4-(2-(1-Imidazolyl)ethyl))phenyl-7-(5-deoxy-1-β-D-ribofuranosyl)pyrrolo|2,3-d|pyrimidine
238) 4-N-(4-(2-(1-tetrazolyl)ethyl)phenyl)amino-5-phenyl-7-(5-deoxy-1-β-D-ribofuranosyl)pyrrolo[2,3-d]pyrimidine
239) 4-N-(4-Fluorophenyl)amino-5-(4-(2-(1-tetrazolyl)ethyl))phenyl-7-(5-deoxy-1-β-D-ribofuranosyl)pyrrolo[2,3-d]pyrimidine
240) 4-N-(4-(2-(2-Tetrazolyl)ethyl)phenyl)amino-5-phenyl-7-(5-deoxy-1-β-D-ribofuranosyl)pyrrolo[2,3-d]pyrimidine
241) 4-N-(4-Fluorophenyl)amino-5-(4-(2-(2-tetrazolyl)ethyl))phenyl-7-(5-deoxy-1-β-D-ribofuranosyl)pyrrolo[2,3-d]pyrimidine
242) 4-N-(4-(2-(5-Tetrazolyl)ethyl)phenyl)amino-5-phenyl-7-(5-deoxy-1-β-D-ribofuranosyl)pyrrolo[2,3-d]pyrimidine
243) 4-N-(4-Fluorophenyl)amino-5-(4-(2-(5-tetrazolyl)ethyl))phenyl-7-(5-deoxy-1-β-D-ribofuranosyl)pyrrolo[2,3-d]pyrimidine
244) 4-N-(3,4-Methylenedioxyphenyl)amino-5-phenyl-7-(5-amino5-deoxy-1-β-D-ribofuranosyl)pyrrolo(2,3-d)pyrimidine.
245) 4-N-(3,4-Ethylenedioxyphenyl)amino-5-phenyl-7-(5-amino-5-deoxy-1-β-D-ribofuranosyl)pyrrolo(2,3-d)pyrimidine.
246) 4-N-Phenylamino-5-(3,4-Methylenedixyphenyl)-7-(5-amino-5-deoxy-1-β-D-ribofuranosyl)pyrrolo(2,3-d)pyrimidine.
247) 4-N-(3,4-dimethoxyphenyl)amino-5-phenyl-7-(5-amino-5-deoxy-1-β-D-ribofuranosyl)pyrrolo(2,3-d)pyrimidine.
248) 4-N-(3,4-Diethoxyphenyl)amino-5-phenyl-7-(5-amino-5-deoxy-1-β-D-ribofuranosyl)pyrrolo(2,3-d)pyrimidine.
249) 4-N-[2-(4-Morpholinoethyl)phenyl]amino-5-(3,4-Methylenedixyphenyl)-7-(5-deoxy-1-β-D-ribofuranosyl) pyrrolo(2,3-d)pyrimidine.

48

250) 4-N-|2-(1-Piperazinonoethyl)phenyl|amino-5-(3,4-Methylenedixyphenyl)-7-(5-deoxy-1-β-D-ribofuranosyl) pyrrolo(2,3-d)pyrimidine.
251) 4-N-|2-(4-Morpholinoethyl)phenyl|amino-5-(4-methoxyphenyl)-7-(5-deoxy-1-β-D-ribofuranosyl) pyrrolo(2,3-d)pyrimidine.
252) 4-N-|2-(Piperidinoethyl)phenyl|amino-5-(4-methoxyphenyl)-7-(5-deoxy-1-β-D-ribofuranosyl) pyrrolo(2,3-d)pyrimidine.
253) 4-N-|2-(N,N-Diethylaminoethyl)phenyl|amino-5-(4-methoxyphenyl)-7-(5-deoxyl-β-D-ribofuranosyl)pyrrolo(2,3-d)pyrimidine.
254) 4-N-|4-(1-Pyrrolidino)phenyl|amino-5-(4-methoxyphenyl)-7-(5-deoxy-1-β-D-ribofuranosyl) pyrrolo(2,3-d)pyrimidine.
255) 4-N-|4-(1-Piperidino)phenyl|amino-5-(4-methoxyphenyl)-7-(5-deoxy-1-β-D-ribofuranosyl) pyrrolo(2,3-d)pyrimidine.
256) 4-N-|4-(1-Piperazino)phenyl|amino-5-(4-methoxyphenyl)-7-(5-deoxy-1-β-D-ribofuranosyl) pyrrolo(2,3-d)pyrimidine.
257) 4-N-|4-(4-Morpholino)phenyl|amino-5-(4-methoxyphenyl)-7-(5-deoxy-1-β-D-ribofuranosyl) pyrrolo(2,3-d)pyrimidine.
258) 4-N-[4-(3-Oxo-1-piperazino)phenyl|amino-5-phenyl-7-(5-deoxy-1-β-D-ribofuranosyl)pyrrolo(2,3-d) pyrimidine.
259) 4-N-|4-(3-5-Dioxo-1-piperazino)phenyl|amino-5-phenyl-7-(5-deoxy-1-β-D-ribofuranosyl)pyrrolo(2,3-d) pyrimidine.
260) 4-N-(4-Guanidinocarbonylphenyl)amino-5-phenyl-7-(5-deoxy-1-β-D-ribofuranosyl)pyrrolo(2,3-d)pyrimidine.
261) 4-N-[4-(N-Hydroxyguanidinocarbonyl)phenyl]amino-5-phenyl-7-(5-deoxy-1-β-D-ribofuranosyl)pyrrolo(2,3-d) pyrimidine.
262) 4-N-[4-(2-Amino-1,2,4-oxadiazol-5-yl)phenyl]amino-5-phenyl-7-(5-deoxy-1-β-D-ribofuranosyl)pyrrolo(2,3-d) pyrimidine.
263) 4-N-(4-Guanidinoaminocarbonylphenyl)amino-5-phenyl-7-(5-deoxy-1-β-D-ribofuranosyl)pyrrolo(2,3-d) pyrimidine.
264) 4-N-[4-N-(2-Imidazolyl)aminocarbonylphenyl|amino-5-phenyl-7-(5-deoxy-1-β-D-ribofuranosyl)pyrrolo(2,3-d) pyrimidine.

EXAMPLE 11

Preferred Pyrazolo|3,4-d|Pyrimidines

Representative, preferred pyrazolo[3,4-d]pyrimidine compounds of the invention, which are not limiting, are identified below. Generally, the most preferred compounds have two aryl groups (e.g. phenyl or substituted phenyl) at positions D and W of the formula below (W corresponds to $(CH_2)_pX$ of Formula 1). Particularly preferred are compounds where D is phenyl. $A_1$, $A_2$, and G of Formula 1 are all hydrogen, and B of is methyl. B may also be $CH_2OH$, and in that case a preferred compound is 134) 1-(1-β-D-ribofuranosyl)-3-phenyl-4-N-(4-N,N-dimethylaminomethyl)phenylaminopyazolo|3,4-d| pyrimidine.

Thus, preferred pyrazolo pyrimidines can be represented by the formula:

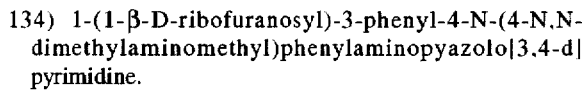

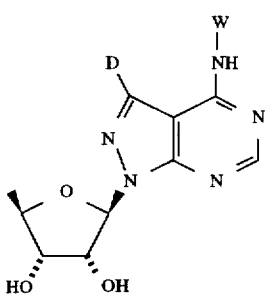

where D is most preferably (a) phenyl, or is preferably (b) 3-pyridyl, (c) 4-(1-morpholinomethyl)phenyl, (d) 4-(1-piperidinoethyl)phenyl, (e) 4-(1-piperizinoethyl)phenyl, (f) 4-(2-aminoethyl)phenyl, (g) 4-(N,N-dimethylaminomethyl)phenyl, (h) 4-(N,N-diethylaminomethyl)phenyl, or (I) 4-(N,N-diethylaminoethyl)phenyl.

When D is phenyl, preferred compounds are those where W is:

135) 4-((Methylphosphoryl)oxy)phenyl
136) [4-(2-Aminoethyl)phenyl
137) 4-(1-morpholino-2-ethylphenyl)
138) (4-(N-Acetylaminosulfonyl)phenyl
139) 4-(1-piperazinoethyl)phenyl
140) 4-(N,N-dimethylaminomethylphenyl
141) 4-(N,N-diethylaminoethyleneaminoethyl)phenyl
142) 4-(2-diethylaminoethyl)phenyl
143) 4-(2-dimethylaminoethyl)phenyl
144) 4-N-Trifluoromethanesulfonylaminophenyl
145) (4-amidoxime)phenyl
146) 4-(N,N-dimethylaminomethyl)phenyl
147) 4-phosphatephenyl
148) 4-N-aminoamidinophenyl
149) 4-N-aminoguanidinophenyl
150) 4-carboxymethyloxyphenyl
151) 4-(2-aminoethyl)carboxamidophenyl
152) 4-(2-N,N-diethylaminoethyl)carboxamidophenyl
153) 4-(morpholinoethyl)carboxamidophenyl
154) 4-(1-pyperazinoethyl)carboxamidophenyl
155) 4-(pyperidinoethyl)carboxamidophenyl
156) 4-N-ethylaminomethyl)phenyl
157) 4-(N-methyl-N-aminomethyl)phenyl
159) 4-(N,N-dimethylaminomethyl)phenyl
160) 3-(N,N-diethylaminomethyl)phenyl
161) 4-(N,N-diethylaminoethyl)phenyl
162) 4-(3-aminopropyl)phenyl
163) 4-(N,N-diethylaminopropyl)phenyl
164) 3-(1-piperidinomethyl)phenyl
165) 4-(N-trifluoromethanesulfonamido)phenyl
166) 4-N-fluorosulfonylaminophenyl When D is 3-pyridyl, preferred compound are those where W is:

167) phenyl
168) 4-fluorophenyl
169) 2-pyridinomethyl; or
170) 4-N,N-dimethylaminomethylphenyl.

When D is any of the groups (c)–(I) immediately above, then W is preferably fluorophenyl (Examples 177–183, respectively).

If desired, these compounds can be provided as salts, e.g. hydrochloride salts, or in lyxose form, as described in Example 10.

Utility

The adenosine kinase inhibitors of the present invention may be used in the treatment of a variety of clinical situations where increasing local levels of adenosine are beneficial. The compounds of the invention act as potent inhibitors of adenosine kinase in vitro, and may be readily administered intravenously.

Adenosine has been proposed to serve as a natural anticonvulsant. Compounds of the present invention which enhance adenosine levels are useful in seizure disorders, as shown in animal models of seizures detailed below. Adenosine kinase inhibitors may be used in the treatment of patients with seizures or epilepsy or patients who might have chronic low or insufficient adenosine levels or might benefit from increased adenosine such as those suffering from autism, cerebral palsy, insomnia or other neuropsychiatric symptoms.

Adenosine kinase inhibitors of the invention find further utility in the treatment of acute pain, including but not limited to peri-operative, post-surgical, and end-stage cancer pain. Compounds of the invention are also useful in controlling chronic pain, including but not limited to pain caused by arthritis, cancer, trigeminal neuralgia, multiple sclerosis, neuropathies such as those arising from diabetes and AIDS and in addition, lower back pain and phantom limb pain. Treatment of acute and chronic pain can be treated by administration of the compounds of the invention in a systemic or oral fashion, as illustrated by animal models detailed below.

Adenosine has been reported to be an endogenous modulator of inflammation by virtue of its effects on stimulated neutrophil function and on macrophage, lymphocyte and platelet function. The compounds of this invention may therefore be used in treating conditions in which inflammatory processes are prevalent such as arthritis, reperfusion injury, and other inflammatory disorders.

The compounds of the invention are also useful in the treatment of chronic neurodegenerative disease, such as Alzheimer's disease, Parkinson's deisease, ALS, Huntington's disease, and AIDS dimentia.

Stroke and central nervous system ("CNS") trauma are conditions where tissue injury results from reduced blood supply to the CNS and are thus amenable to an intervention that provides increased levels of adenosine to the compromised tissue. It is reported that a significant component of the neurodegeneration resulting from stroke or CNS trauma is caused by increased excitatory amino. acid release and sensitivity, which results in neurons being stimulated to death. In addition to vasodilatory properties, adenosine has been reported to inhibit release of excitatory amino acids (Burke and Nadler *J. Neurochem.*, 51:1541(1988)) and responsiveness of neurons to excitation. The compounds of this invention, which increase adenosine levels, may also be used in the treatment of conditions where release of or sensitivity to excitatory amino acids is implicated.

To assist in understanding the present inventions and especially their properties and utilities, the results of a series of experiments are also included. These experiments demonstrated that a number of compounds of the present invention were potent inhibitors of a purified cardiac adenosine kinase. Certain adenosine kinase inhibitors were found to inhibit seizures in a well-established animal model, and exemplary compounds inhibited pain in two other animal models. Results are set forth in Tables 1–3.

AK Inhibition

Adenosine kinase activity was measured essentially as described by Yamada et al. *Biochim. Biophys. Acta* 660, 36–43 (1988) with a few minor modifications. Assay mixtures contained 50 mM TRIS-maleate buffer, pH 7.0, 0.1% BSA, 1 mM ATP 1 mM $MgCl_2$, 0.5 µM [U-$^{14}$C] adenosine (400–600 mCi/mmol) and varying duplicate concentrations of inhibitor. The reactions were initiated by addition of approximately 0.1 µU partially purified pig heart adenosine kinase or recombinant human adenosine kinase (Spychala et al., *Proc.Nat.Acad.Sci. USA* 93, 1232 (1996) where one unit is defined as that amount of enzyme required to phosphorylate 1 µmol adenosine per minute. The reactions were incubated for 20 minutes at 37° C. The assay was quenched upon spotting 30 µL aliquots onto 2 $cm^2$ pieces of Whatman DE81 anion exchange paper. The paper squares were washed for 3 minutes in 6 L distilled/deionized water to remove the unreacted adenosine. The washed squares were rinsed in 95% ethanol and dried in an oven at 100° C. for 10 minutes. The amount of $^{14}$C-AMP was quantified by scintillation counting. The concentration of inhibitor required to inhibit 50% of the adenosine kinase activity ($IC_{50}$) was determined graphically. The results for representative compounds of the invention are shown in Table 1.

Anticonvulsant Activity

The anticonvulsant activity of the tested compounds was evaluated in male SA rats (100–150g, Simonsen) using the maximal electroshock (MES) model described in Swinyard et al., *Antiepileptic Drugs*, 3d Ed. at 85–102 (Levy, et al., eds.), NY: Raven Press (1989). The rats were maintained on a 12/12 light/dark cycle in temperature controlled facilities with free access to food and water. For p.o. administration, the animals are fasted overnight, prior to the experiment. One to two hours prior to seizure testing, the animals were injected interperitoneally (ip) or orally (per os, po) with one of various doses of test compound dissolved in DMSO or PEG 400.

Maximal electroshock seizures (MES) were induced by administering a 150 mA, 60 Hz current for 0.2 seconds via corneal electrodes using a Wahlquist Model H stimulator. The endpoint measurement was suppression of hind limb tonic extension (HTE), which was judged to occur when any hind leg extension did not exceed a 90 degree angle with the plane of the body. HTE suppression of this kind indicates that the test compound has the ability to inhibit seizures, in theory by inhibiting seizure propagation and spread, if not by raising the seizure threshold (Le. preventing seizure potential). This endpoint was expressed as the percentage of animals in which the response was inhibited. Typically, compounds were screened initially at one hour following a dose of 5 mg/kg ip. In some cases, the effective dose at which 50% of the rats were protected ($ED_{50}$) was calculated from a dose response curve. The results for exemplary compounds of the invention are set forth in Table 1, expressed as $ED_{50}$ values. For compounds where the $ED_{50}$ was not calculated, the result is listed as >5 if HTE was inhibited in fewer than 50% of the animals in the initial screen, or <5 if HTE was inhibited in more than 50% of the animals in the initial screen. >>or < signs are used to indicate that either no activity or maximal activity, respectively, were observed at the stated dose. Results are shown in Table 1.

TABLE 1

UTILITY OF REPRESENTATIVE AK INHIBITORS

| # | AK Inhibition ($IC_{50}$) nmol. | Anticonvulsant $ED_{50}$(MES) mg/kg ip | po |
|---|---|---|---|
| 1 | 4 | >5 | >20 |
| 22 | 2 | >5 | |
| 3 | 2 | <5 | >10 |
| 4 | 1 | >5 | |
| 6 | 1 | >>5 | |
| 5 | 1 | 5 | >10 |
| 7 | 1 | >5 | |
| 8 | 50 | >>5 | |
| 40 | 3000 | | |
| 42 | 75 | 2.0 | |
| 49 | 67 | 10.9 | >>40 |
| 50 | 5 | 5 | |
| 41 | 70 | 0.5 | |
| 43 | 10,000* | 1.0 | |
| 44 | 120 | <5.0 | |
| 48 | 300 | | |
| 47 | 55 | | |
| 45 | 500 | | |
| 46 | 220 | >>5.0 | |
| 37 | 5 | >>5.0 | |
| 16 | 1 | | |
| 2 | 1 | 5 | |
| 29 | 0.5 | | |
| 39 | 1 | >>5.0 | |
| 209 | 80 | >>5.0 | |
| 210 | 2 | >5.0 | |
| 211 | 0.5 | >>5.0 | |
| 267 | 1 | <5.0 | |
| 200 | 200 | | |
| 199 | 550 | | |
| 198 | 120 | | |
| 196 | 0.35 | >>5.0 | |
| 266 | 0.3 | >5.0 | |
| 269 | 6 | 5.0 | |
| 265 | 2 | >5.0 | |
| 212 | 2 | >5.0 | |
| 189 | 1 | | |
| 206 | 7 | | |
| 186 | 80 | | |
| 268 | 1 | | |
| 202 | 20 | | |
| 204 | 45 | | |
| 197 | 9 | | |
| 12 | 0.3 | | |

*This compound is a weak AK inhibitor in vitro, but has been shown by HPLC analysis of plasma to undergo metabolism in mice after oral administration (10 mg/kg) to generate a potent AK inhibitor.

Analgesic Activity

Analgesic activity of representative compounds of the invention was evaluated in male SA rats (100–150 g, Simonsen) using the hot plate and tail flick models of pain, similar to those described in Sosnowski et al., *J. Pharmacol. Exper. Ther.*, 250:3, 915–922 (1989). See also, *Life Sciences* 51:171–76 (1992). These models measure pain avoidance and tolerance in response to a regulated stimulus, and compare the response of animals before and after they are given test compound.

The tail flick response is evoked by placing the tail of a rat over a focused beam of light. The latency or response time to flick the tail away from the incident heat source was recorded electronically by an appropriate measuring device, for example an apparatus manufactured by Ugo Basile. Longer times indicate greater tolerance to the thermally induced pain stimulus. The maximum exposure time is limited to avoid tissue damage (8 seconds), in the event a rat does not respond to the stimulus within a predetermined period. In this experiment, the rats were accommodated to the hand restraint of the testing to prevent spurious movements from causing false responses. A mark was made on the dorsal surface of each tail approximately 3–5 cm from the tip to ensure testing at the same location on the tail.

Figure 2:
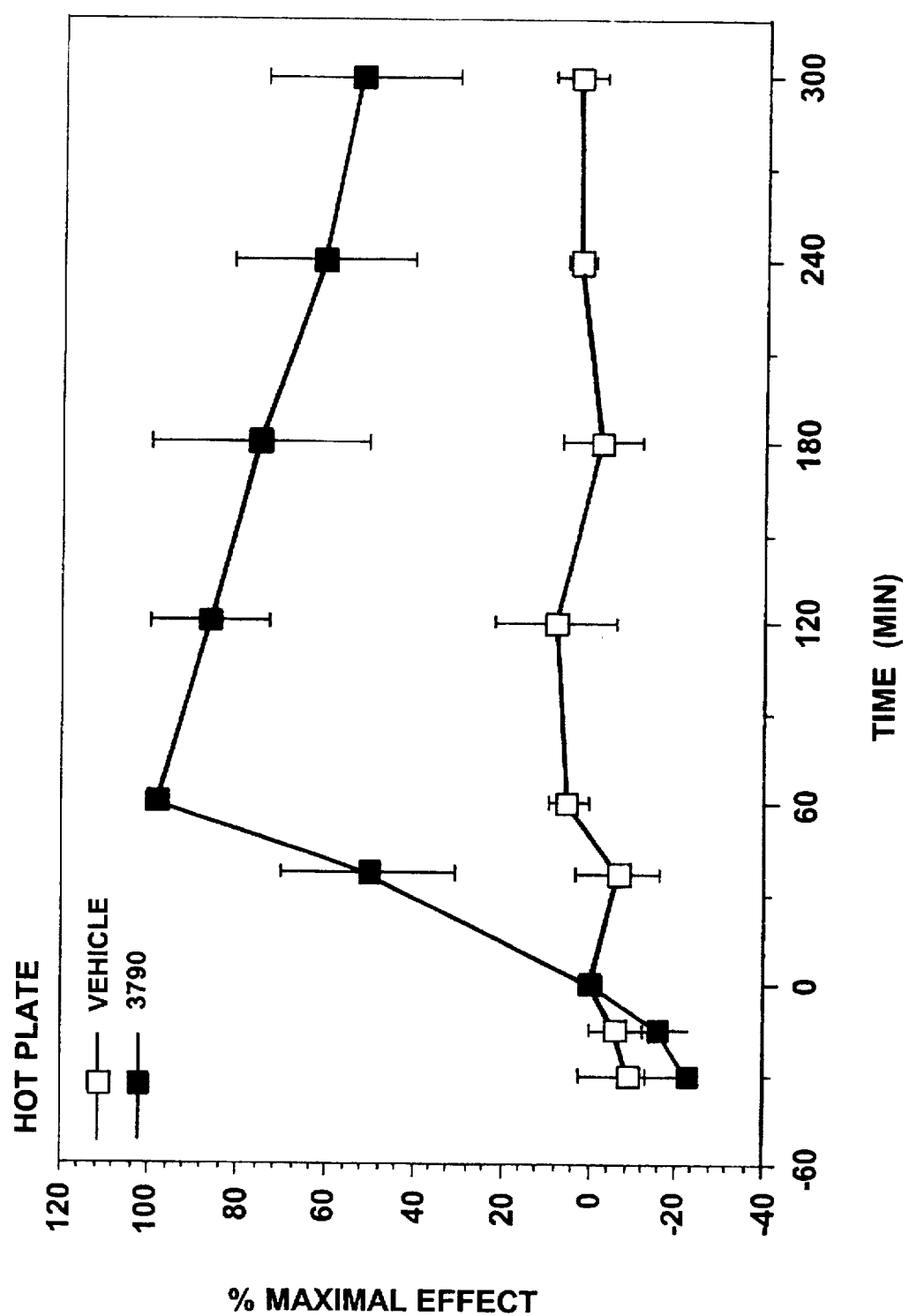
FIG. 2 shows the effects of administering compound #3 to test animals on the animals' responses to the hot plate test.

In the hot plate model, a rat is placed on a heated metal plate (typically 50° C.). The endpoint of this evaluation is the time required for the rat to lick its hind paw. A predetermined cutoff time (60 seconds) is used to protect the animals from injury, in the event there is no response. Three hot plate and tail flick tests were performed 15 minutes apart prior to dosing; these tests serve as the baseline for each animal. Rats were administered one of various doses intraperitoneally (ip) and the tail flick and hot plate responses were monitored at various times (e.g. 30, 60, 120, 240, and 300 minutes after administration). In addition, Example 3 was tested following a single dose administered intravenously (iv) by means of a chronic catheter previously implanted in the jugular vein. The results (%MPE) are shown in FIG. 1 (tail flick) and FIG. 2 (hot plate).

Dose response curves for each compound in the tail flick and hot plate tests are made by plotting the dose against the normalized peak response, or percent maximum possible effect (%MPE). The %MPE is calculated as $$\frac{(\text{test latency} - \text{baseline latency})}{(\text{cutoff latency} - \text{baseline latency})} \times 100\%$$

The effective dose at which 50% of the rats were protected ($ED_{50}$) was calculated from the dose response curve using linear regression analysis. Results for representative compounds according to the invention are set forth in Table 2.

Formalin Paw Assay

In this assay, injection of formalin, an irritant, into the hindpaw of rats typically evokes a biphasic response of pain-related behaviors. Phase 1 of the response which is brief, lasting approximately 0–5 min post-injection, is followed by a more prolonged phase 2, lasting approximately 10–80 min post-injection. Phase 1 behavior is thought to be a direct effect of the irritant on nociceptors at the injection site while phase 2 behavior is thought to include a hyperalgesic component mediated by sensitization of neuronal elements within the spinal cord. Studies from other laboratories have found the first portion of Phase 2 (sometimes referred to as Phase 2a) to be most responsive to pharmacological manipulation.

Rats (male, Simonsen) weighing between 100–200 g, are used in the present experiments. For screening purposes drugs are administered orally 90 min prior to initiation of formalin test. At designated intervals the animals in groups of 4 are placed individually in a small animal restrainer with the right hindpaw accessible through a hole in the bottom of the restrainer. The formalin paw assay is initiated by the injection using a 30G needle of 50 ul of a 5% formalin solution in saline into the right plantar surface of each hindpaw. The rat is then immediately placed in a separate plexiglass box and scoring (described below) of the animal's behavior is begun at 1.7 min after formalin injection. The instantaneous behavior of each animal in a group of 4 was observed and assigned a score once in each 20 second interval. This sequence is repeated over a 30 min period. The scoring protocol is an adaptation of the method published by Dubuisson and Dennis (Pain 4:161–174, 1977) which assigns a score from 0–3 as follows:

0—no discernible favoring of injected paw, weight evenly distributed

1—injected paw is favored, rests lightly on floor

2—injected paw is elevated

3—injected paw is vigorously licked, bitten, or shaken

Scores are continuously recorded directly onto an Excel spreadsheet. For comparative examination of drug effects the data is reported two different ways: 1) the scores are summed for Phase 1 (1.7–5 min post-formalin) and for Phase 2 (10.3–30 min post-formalin) and the mean values of the sums are determined from 6 different animals with results expressed as % inhibition compared to vehicle control; 2) the total number of incidences specifically of licking/biting behavior is summed over Phase 2 and mean values determined from 6 different animals with results expressed as % inhibition compared to vehicle control. Phase 2 composite score results for compound 3 was 31 percent inhibition. Phase 2 composite score results for compound 266 was 47 percent.

Anti-Inflammatory Activity

Carrageenan (Type λ) was suspended in sterile PBS at 1% (w/v), autoclaved for 30 minutes, and stored at room temperature. Rats were pretreated with vehicle or AK inhibitor (10 mg/kg) by oral gavage or i.p. administration and the volume of the left hind paw was measured using a water displacement plethysmometer (Stoelting Co., Wood Dale, Ill.). One hour after oral treatment or 30 minutes after i.p. treatment, the rats were briefly anesthetized, and 0.1 ml of the carrageenan solution was injected subcutaneously into the planar surface of the left hind paw. The ensuing paw swelling was measured by plethysmometry after 3 hours. The paw volume in millileters was subtracted from the pre-injection paw volume. Data are presented in Table 2 as the percent inhibition of paw swelling in AK inhibitor treated animals, compared to vehicle treated control animals. Rosengren et al., *J. Immunology* 154: 5444–51 (1995).

TABLE 2

ANALGESIC/ANTI-INFLAMMATORY UTILITY

| | Analgesic $ED_{50}$ (mg/kg) | | | | Carrageenan Paw (% inhibition) | |
|---|---|---|---|---|---|---|
| | Hot Plate | | Tail Flick | | | |
| # | ip | po | ip | po | ip | po |
| 1 | 15.2 | | 15.2 | | 26.0 | 19.2 |
| 22 | | | | | 31.6 | 12.4 |
| 3 | | | | | 19.5 | 9.8 |
| 4 | | | | | 39.9 | 2.5 |
| 6 | | | | | 81.5 | 42.6 |
| 5 | | | | | 0.0 | 4.1 |
| 7 | | | | | 19.0 | 7.7 |
| 41 | 1.2 | | <1.0 | | 84.8 | 90.6 |
| 43 | | | | | 58.6 | 69.7 |
| 47 | | | | | 0.0 | 9.8 |
| 16 | | | | | 31.6 | 12.4 |
| 2 | | | | | 13.2 | 1.9 |
| 29 | | | | | 26.1 | 14.9 |
| 37 | | | | | 17.9 | 23.3 |
| 210 | | | | | 23.8 | 0.0 |
| 209 | | | | | 22.0 | 0.0 |
| 267 | | | | | 52.3 | 15.4 |
| 196 | | | | | 11.8 | 0.0 |
| 266 | | | | | 71.9 | 56.0 |
| 265 | | | | | 10.0 | 6.2 |
| 212 | | | | | 1.8 | 0.0 |
| 189 | | | | | 30.1 | 12.1 |

TABLE 2-continued

ANALGESIC/ANTI-INFLAMMATORY UTILITY

| # | Analgesic ED$_{50}$ (mg/kg) | | | | Carrageenan Paw (% inhibition) | |
|---|---|---|---|---|---|---|
| | Hot Plate | | Tail Flick | | | |
| | ip | po | ip | po | ip | po |
| 206 | | | | | 10.1 | 23.5 |
| 268 | | | | | 0.0 | 7.1 |
| 202 | | | | | 3.4 | 3.9 |
| 12 | | | | | 58.8 | 51.0 |

Water Solubility

Water solubility was estimated by taking a sample of the compound to be tested (usually between 1 and 2 mg) and adding 1.0 ml of deionized water or an aqueous buffer solution. The sample was sonicated for a period of up to 20 minutes. If a solution was not obtained, further solvent was added and the process was repeated until a clear solution was obtained, and the results were recorded. Solutions used were 50 mM potassium biphthalate (pH 4); 100 mM glycine (pH 9); 25 mM sodium carbonate and 25 mM sodium bicarbonate (pH 10); or deionized water (DI). The solubilities for representative compounds of the invention are shown in Table 3.

TABLE 3

WATER SOLUBILITY

| # | Water Solubility | |
|---|---|---|
| | mg/ml | pH |
| 1 | >5 | DI |
| 22 | >1 | 4 |
| 3 | >1 | 4 |
| 4 | >1 | 4 |
| 6 | >1 | 4 |
| 5 | >5 | DI |
| 7 | >1 | 4 |
| 8 | >1 | 10 |
| 40 | >1 | 9 |

For comparison, a representative compound without the water solubilizing groups of the invention, 5-phenyl-4-N-phenylamino-7-(5-deoxy-1-β-D-ribofuranosyl)pyrrolo[2,3-d]pyrimidine, has a water solubility of less than 20 μg/ml at a suitable pH for i.v. administration (e.g. pH 4 to 10).

Liver Toxicity Assay

Female SA rats (150–200 g) are anesthetized with halothane and cannulated via the internal jugular vein. The animals are allowed to recover for 3 days. At this time, 37.5 μmole/kg of an AK inhibitor is dissolved in 50% PEG400 and infused through the jugular catheter over 20 minutes. Twelve hours later, an additional 37.5 μmole/kg is infused over 20 minutes (total dose =75 μmole/kg). Twelve hours after the second dose, the animals are anesthetized with halothane and exsanguinated through the inferior vena cava. Liver enzymes (serum glutamic-oxaloacetic transaminase (SGOT), serum glutamic-pyruvic transaminase (SGPT), alkaline phosphatase) and total bilirubin in the serum samples are determined by a commercial laboratory.

TABLE 4

LIVER TOXICITY

| # | Total Bilirubin (mg/dL) | | SGOT (IU/L) | | SGPT (IU/L) | | Alkaline (IU/L) Phosphatase | |
|---|---|---|---|---|---|---|---|---|
| Vehicle | 0.10 | ±0.04 | 59 | ±3 | 42 | ±0 | 140 | ±50 |
| REF.A | 0.76 | | 508 | | 76 | | 163 | |
| REF.B | 0.30 | | 100 | | 41 | | 113 | |
| 1 | 0.13 | | 75 | | 44 | | 131 | |
| 22 | 0.13 | | 68 | | 42 | | 105 | |
| 4 | 0.12 | | 84 | | 41 | | 147 | |
| 6 | 0.43 | | 306 | | 110 | | 104 | |
| 266 | 0.62 | | 230 | | 88 | | 72 | |
| 12 | 0.41 | | 211 | | 76 | | 106 | |

REF A. 4-amino-5-iodo-7-(5-deoxy-1-β-D-ribofuranosylpyrrolo[2,3-d]pyrimidine
REF B. 4-amino-1-(5-amino-5-deoxy-1-β-D-ribofuranosyl)-3-bromopyrazolo[3,4-d]pyrimidine HCL

Prodrugs

Prodrugs of the described compounds are within the scope of the invention, and can be prepared by esterification of the hydroxyl groups on the ribofuranose ring. Specially preferred will be the ester derivatives that improve the water solubility properties of the resulting prodrug in order to facilitate their administration via iv route. Examples of prodrugs within the scope of the invention are illustrated below.

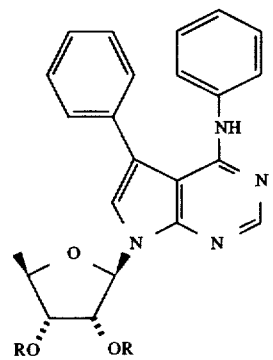

where R is selected from the group consisting of:

- an ester of an alkanoic acid, such as an acetate, propionate, or any other alkyl carboxylate;
- an ester of an aminoacid such as a valine, glycine; a carbonate, such as a cyclic 2',3'-carbonate or a dicarbonate;
- a phosphate ester, including but not limited to cyclic 2',3'-phosphate;
- an ester of a functionalized alkanoic acid where the substituent on the alkyl chain is a substituted amine having the formula

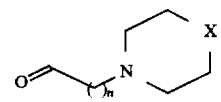

where n is 3 to 5 and X=O, NH, NHCH$_3$, NHCH$_2$CH$_3$;

- an ester of a functionalized alkanoic acids where the substituent on the alkyl chain is a substituted amide of the formula

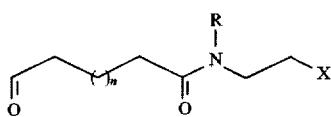

where n=2-4; R=CH$_3$, CH$_2$CH$_3$; X=SO$_3$Na, PO(ONa)$_2$, NR$^1$R$^2$, with R$^1$ and R$^2$=alkyl or aminoalkyl groups;

benzoate esters substituted with solubilizing groups at the 3- or 4-position of the aromatic ring as illustrated below:

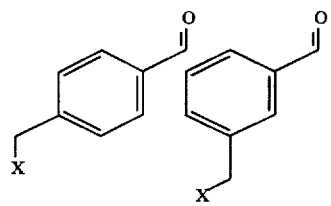

where X=NR$^1$R$^2$, with R$^1$ and R$^2$=methyl, ethyl or propyl X=4-morpholino, 1-piperazino, 4-methyl-1-piperazino, 1-piperidino;

an ester of a heteroaromatic carboxylic acid such as 2-pyridinocarboxylic acid, 3-pyridino carboxylic acid, 4- pyridino carboxylic acid, N-substituted 2- or 3-pyrrolocarboxylic acid; or an ester of ionized carboxylic acid, e.g. N-methyl pyridinium-3-carboxylic acid.

Formulations

Compounds of the invention are administered to the affected tissue at the rate of from 0.1 to 200 nmol/min/kg, preferably from 1 to 50 nmol/min/kg. Such rates are easily maintained when soluble compounds are intravenously administered as discussed below. When other methods are used (e.g., oral administration), use of time-release preparations to control the rate of release of the active ingredient may be preferred. These compounds are administered in a dose of about 0.01 mg/kg/day to about 100 mg/kg/day, preferably from about 0.1 mg/kg/day to about 10 mg/kg/day.

For the purposes of this invention, the compounds of the invention may be administered by a variety of means including orally, parenterally, by inhalation spray, topically, or rectally in formulations containing conventional non-toxic pharmaceutically acceptable carriers, adjuvants and vehicles. The term parenteral as used herein includes subcutaneous, intravenous, intramuscular, and intraarterial injections with a variety of infusion techniques. Intraarterial and intravenous injection as used herein includes administration through catheters. Preferred for certain indications are methods of administration which allow rapid access to the tissue or organ being treated, such as intravenous injections for the treatment of myocardial infarction. When an organ outside a body is being treated, perfusion is preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including those from the group consisting of sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium carbonate, sodium carbonate, lactose, calcium phosphate or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules wherein the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylmethylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadeaethyleneoxycetanol), a condensation product of ethylene oxide with a partial ester derived from a fatty acid and a hexitol anhydride (e.g., polyoxyethylene sorbitan mono-oleate). The aqueous suspension may also contain one or more preservative such as ethyl of n-propyl p-hydroxybenzoate, one or more coloring agent, one or more flavoring agent and one or more sweetening agent, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these.

Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 20 to 1000 µmoles of active material compounded with an appropriate and convenient amount of carrier material which may vary from about 5 to about 95% of the total compositions. It is preferred that pharmaceutical composition be prepared which provides easily measurable amounts for administration. For example, an aqueous solution intended for intravenous infusion should contain from about 0.1 to about 15 µmoles of the active ingredient per milliliter of solution in order that infusion of a suitable volume at a rate of about 30 mL/hr can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach. This is particularly advantageous with the compounds of formula (I) as such compounds are susceptible to acid hydrolysis.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier. Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the ddPN ingredient such carriers as are known in the art to be appropriate.

Formations suitable for parenteral administration include aqueous and non-aqueous isotonic sterile injection solutions which may contain anti-oxidants, buffers, bacteriostats and solutes which render the formation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be sorted in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, or an appropriate fraction thereof, of an adenosine kinase inhibitor compound. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Capsules comprising adenosine kinase inhibitors suitable for oral administration according to the methods of the present invention may be prepared as follows: (1) for a 10,000 capsule preparation: 1500 g of adenosine kinase inhibitor is blended with other ingredients (as described above) and filled into capsules which are suitable for administration depending on dose, from about 4 capsules per day (1 per 6 hours) to about 8 capsules per day (2 capsules per 6 hours), to an adult human.

The compounds of this invention and their preparation and use can be understood further by the representative examples above, which illustrate the various aspects of the invention without limiting its scope.

We claim:

1. A compound of the formula

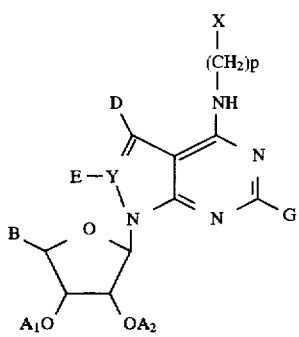

wherein:

$A_1$ and $A_2$ are each hydrogen or acyl, or together form a cyclic carbonate;

B is alkenyl, or $(CH_2)_n$—B', where n is from 1 to 4 and B' is hydrogen, hydroxy, alkyl, alkoxy, amino, azido, halogen, or alkenyl;

D is alkyl or alkenyl;

X is a carbocyclic or heterocyclic aryl ring substituted with a water solubilizing group $(CH_2)_rT$, where r is from 0 to 3 and T is one of an alkyl or an alkenyl chain of 1 to 16 carbons containing a carboxylic acid and optionally containing one or more nitrogen or oxygen atoms, a 5- or 6-membered nitrogen-containing heterocyclic aryl group, sulfonate, mono- or disubstituted squaric acid group, 5-tetrazolyl, N-sulfonylated amino, amidoximo, N-aminoguanidino, amidino, guanidino, a cyclic amidine, a cyclic guanidine, acylated sulfonamide, acylated guanidino, a 5 or 6 membered alicyclic ring containing nitrogen and optionally containing oxygen, the group $CONR^1R^2$, where $R^1$ and $R^2$ are independently an alkyl chain containing one or more basic nitrogen atoms, and optionally containing oxygen, or $R^1$ and $R^2$ together form a 5 or 6-membered ring containing at least one basic nitrogen;

Y is carbon or nitrogen;

E is nothing when Y is nitrogen, and is hydrogen or halogen when Y is carbon;

G is hydrogen or halogen;

p is from 0 to 3;

and pharmaceutically acceptable salts thereof.

2. A compound of claim 1, where Y is carbon.

3. A compound of claim 1, where Y is nitrogen.

4. A compound of claim 1, where G and each A are hydrogen.

5. A compound of claim 1, where E, G, and each A are hydrogen.

6. A compound of claim 1, where G and each A are hydrogen.

7. A compound of claim 2, where G and each A are hydrogen.

8. A compound of the formula

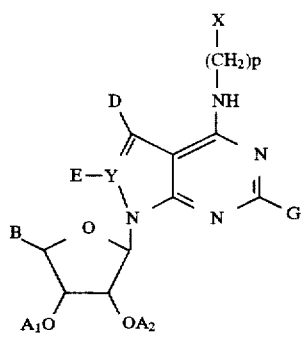

wherein:

$A_1$ and $A_2$ are each hydrogen or acyl, or together form a cyclic carbonate;

B is alkenyl, or $(CH_2)_n$—B', where n is from 1 to 4 and B' is hydrogen, hydroxy, alkyl, alkoxy, amino, azido, halogen, or alkenyl;

D is halogen, alkyl, alkenyl, alkynyl, haloalkyl, cyano, carboxamido, or $(CH_2)_qX$, where q is 0–3;

each X is independently a carbocyclic or heterocyclic aryl optionally substituted at any position by halogen, alkyl, alkoxy, substituted per halo lower alkyl, sulfonamide, cyano, CONRR' where R and R' are independently hydrogen or lower alkyl, or a water solubilizing group $(CH_2)_rT$, where r is from 0 to 3 and T is one of sulfonate, mono- or disubstituted squaric acid group, 5-tetrazolyl, an alkyl or an alkenyl chain of 1 to 16 carbons containing a carboxylic acid and optionally containing one or more nitrogen or oxygen atoms; or a 5- or 6-membered nitrogen-containing heterocyclic aryl group;

Y is carbon or nitrogen;

E is nothing when Y is nitrogen, and is hydrogen or halogen when Y is carbon;

G is hydrogen or halogen;

p is from 0 to 3;

and pharmaceutically acceptable salts thereof;

provided at least one X includes a water solubilizing group as defined above.

9. A compound of claim 8 where Y is carbon.

10. A compound of claim 8 where Y is nitrogen.

11. A compound of claim 8, where D is $(CH_2)_qX$.

12. A compound of claim 8, where G and each A are hydrogen.

13. A compound of claim 9, where E, G, and each A are hydrogen.

14. A compound of claim 10, where G and each A are hydrogen.

15. A compound of claim 11, where G and each A are hydrogen.

16. A compound of claim 9, where D is $(CH_2)_qX$, and E, G and each A are hydrogen.

17. A compound of claim 11, where Y is carbon.

18. A compound of claim 11, where Y is nitrogen.

19. A compound of the formula

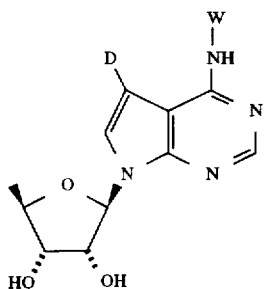

wherein D is selected from the group consisting of phenyl, 3-pyridyl, 4-(4-morpholinomethyl)phenyl, 4-(1-piperidinoethyl)phenyl, 4-(2-(1-piperazino)ethyl)phenyl, 4-(2-aminoethyl)phenyl, 4-(N,N-dimethylaminomethyl)phenyl, 4-(N,N-diethylaminomethyl)phenyl, 3-guanidinophenyl, and 4-(N,N-diethylaminoethyl)phenyl;

wherein W is a phenyl ring containing a water solubilizing group $(CH_2)_rT$, where r is from 0 to 3 and T is selected from the group consisting of acylated guanidino, carboxylic acid, or a 5- or 6-membered nitrogen-containing heterocyclic aryl group.

20. A compound of claim 3 wherein D is phenyl.

21. A compound of the formula

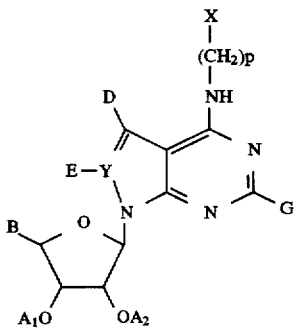

wherein:

$A_1$ and $A_2$ are each hydrogen or acyl, or together form a cyclic carbonate;

B is alkenyl, or $(CH_2)_n$—B', where n is from 1 to 4 and B' is hydrogen, hydroxy, alkyl, alkoxy, amino, azido, halogen, or alkenyl;

D is halogen, alkyl, alkenyl, alkynyl, haloalkyl, cyano, carboxamido, or $(CH_2)_qX$, where q is 0–3;

each X is independently a carbocyclic or heterocyclic aryl optionally substituted at any position by halogen, alkyl, alkoxy, substituted perhalo lower alkyl, sulfonamide, cyano, CONRR' where R and R' are independently hydrogen or lower alkyl, or a water solubilizing group $(CH_2)_rT$, where r is from 0 to 3 and T is one of an alkyl or an alkenyl chain of 1 to 16 carbons containing a carboxylic acid and optionally containing one or more nitrogen or oxygen atoms, a 5- or 6-membered nitrogen-containing heterocyclic aryl group, sulfonate, mono- or disubstituted squaric acid group, 5-tetrazolyl, N-sulfonylated amino, amidoximo, N-aminoguanidino, amidino, guanidino, a cyclic amidine, a cyclic guanidine, acylated sulfonamide, acylated guanidino, a 5 or 6 membered alicyclic ring containing nitrogen and optionally containing oxygen, or the group $CONR^1R^2$, where $R^1$ and $R^2$ are independently an alkyl chain containing one or more basic nitrogen atoms, and optionally containing oxygen, or $R^1$ and $R^2$ together form a 5 or 6-membered ring containing at least one basic nitrogen;

Y is carbon or nitrogen;

E is nothing when Y is nitrogen, and is hydrogen or halogen when Y is carbon;

G is hydrogen or halogen;

p is from 0 to 3;

and pharmaceutically acceptable salts thereof;

provided at least one X includes a water solubilizing group as defined above.

* * * * *

UNITED STATES PATENT AND TRADEMARK OFFICE
CERTIFICATE OF CORRECTION

PATENT NO. : 5,795,977
DATED : Aug. 18, 1998
INVENTOR(S) : Ugarkar et al.

It is certified that error appears in the above-identified patent and that said Letters Patent is hereby corrected as shown below:

On the title page, item [*] Notice, after "Pat. No." delete "5,726,308" and insert --5,726,302--.

Signed and Sealed this

Sixteenth Day of February, 1999

*Attest:*

*Attesting Officer*

*Acting Commissioner of Patents and Trademarks*